US011021709B2

(12) United States Patent
Sliz et al.

(10) Patent No.: US 11,021,709 B2
(45) Date of Patent: Jun. 1, 2021

(54) LIN28/LET-7 CRYSTAL STRUCTURES, PURIFICATION PROTOCOLS, AND MOLECULAR PROBES SUITABLE FOR SCREENING ASSAYS AND THERAPEUTICS

(71) Applicant: PRESIDENT AND FELLOWS OF HARVARD COLLEGE, Cambridge, MA (US)

(72) Inventors: Piotr Sliz, Canton, MA (US); Yunsun Nam, Dallas, TX (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/887,632

(22) Filed: May 29, 2020

(65) Prior Publication Data

US 2020/0362350 A1 Nov. 19, 2020

Related U.S. Application Data

(63) Continuation of application No. 15/984,109, filed on May 18, 2018, now Pat. No. 10,704,049, which is a continuation of application No. 15/420,571, filed on Jan. 31, 2017, now Pat. No. 10,000,756, which is a continuation of application No. 14/357,020, filed as application No. PCT/US2012/064412 on Nov. 9, 2012, now Pat. No. 9,593,141.

(60) Provisional application No. 61/557,655, filed on Nov. 9, 2011.

(51) Int. Cl.

| | |
|---|---|
| ***C12N 15/113*** | (2010.01) |
| ***A61K 45/06*** | (2006.01) |
| ***C07K 14/47*** | (2006.01) |
| ***A61K 47/60*** | (2017.01) |
| ***A61K 47/64*** | (2017.01) |
| ***C07H 21/02*** | (2006.01) |
| ***A61K 48/00*** | (2006.01) |
| ***A61K 31/7105*** | (2006.01) |
| ***A61K 31/7115*** | (2006.01) |
| ***A61K 31/712*** | (2006.01) |
| ***A61K 31/713*** | (2006.01) |

(52) U.S. Cl.

CPC ........ *C12N 15/1135* (2013.01); *A61K 31/712* (2013.01); *A61K 31/713* (2013.01); *A61K 31/7105* (2013.01); *A61K 31/7115* (2013.01); *A61K 45/06* (2013.01); *A61K 47/60* (2017.08); *A61K 47/645* (2017.08); *C07H 21/02* (2013.01); *C07K 14/47* (2013.01); *C07K 14/4702* (2013.01); *A61K 48/00* (2013.01); *C12N 2310/11* (2013.01); *C12N 2310/141* (2013.01); *C12N 2310/531* (2013.01)

(58) Field of Classification Search

None

See application file for complete search history.

(56) References Cited

U.S. PATENT DOCUMENTS

| | | | |
|---|---|---|---|
| 2010/0069471 | A1 | 3/2010 | Manoharan |
| 2010/0221266 | A1 | 9/2010 | Gregory |

OTHER PUBLICATIONS

Heo et al., "TUT4 in concert with Lin28 suppresses microRNA biogenesis through pre-microRNA uridylation", Cell 138(4) 696-708 (2009).

Newman et al., "Lin-28 interaction with the Let-7 precursor loop mediates regulated microRNA processing", RNA 14(8) 1539-1549 (2008).

Chang et al., "Lin-28B transactivation is necessary for Myc-mediated let-7 repression and proliferation", Proc Natl Acad Sci USA 106(9) 3384-3389 (2009).

Nam et al., "Molecular basis for interaction of let-7 microRNAs with Lin28", Cell 147(5) 1080-1091 (2011).

Bussing et al., "let-7 microRNAs in development, stem cells and cancer", Trends Mol Med 14(9) 400-409 (2008).

Davis-Dusenbery et al., "Mechanisms of control of microRNA biogenesis", J Biochem 148(4) 381-392 (2010).

De Guzman et al., "Structure of the HIV-1 nucleocapsid protein bound to the SL3 psi-RNA recognition element", Science 279(5349) 384-388 (1998).

Guo et al., "Identification and characterization of lin-28 homolog B (LIN28B) in human hepatocellular carcinoma", Gene 384: 51-61 (2006).

Hagan et al., "Lin28 recruits the TUTase Zcchc11 to inhibit let-7 maturation in mouse embryonic stem cells", Nat Struct Mol Biol 16(10) 1021-1025 (2009).

Han et al., "Molecular basis for the recognition of primary microRNAs by the Drosha-DGCR8 complex", Cell 125(5) 887-901 (2006).

Heo et al., "Lin28 mediates the terminal uridylation of let-7 precursor MicroRNA", Mol Cell 32(2) 276-284 (2008).

Iliopoulos et al., "An epigenetic switch involving NF-kappaB, Lin28, Let-7 MicroRNA, and IL6 links inflammation to cell transformation", Cell 139(4) 693-706 (2009).

Jin et al., "Evidence that Lin28 stimulates translation by recruiting RNA helicase A to polysomes", Nucelic Acids Res 39(9) 3724-3734 (2011).

Kim et al., "Biogenesis of small RNAs in animals", Nat Rev Mol Cell Biol 10(2) 126-139 (2009).

King et al., "LIN28B promotes colon cancer progression and metastasis", Cancer Res 71(12) 4260-4268 (2011).

Klein et al., "The kink-turn: a new RNA secondary structure motif", EMBO J 20(15) 4214-4221 (2001).

Krol et al., "The widespread regulation of microRNA biogenesis, function and decay", Nat Rev Genet 11(9) 597-610 (2010).

(Continued)

*Primary Examiner* — Suzanne M Noakes

(74) *Attorney, Agent, or Firm* — Nixon Peabody LLP

(57) ABSTRACT

The invention provides compositions and methods for regulating microRNA (miRNA) biogenesis. The invention also relates to compositions and methods for treating or preventing cancer in a subject in need thereof.

20 Claims, 14 Drawing Sheets

Specification includes a Sequence Listing.

(56) References Cited

OTHER PUBLICATIONS

Lehrbach et al., "LIN-28 and the poly(U) polymerase PUP-2 regulate let-7 microRNA processing in Caenorhabditis elegans", Nat Struct Mol Biol 16(10) 1016-1020 (2009).
Lettre et al., "Identification of ten loci associated with height highlights new biological pathways in human growth", Nat Genet 40(5) 584-591 (2008).
Lu et al., "Pluripotent factor lin-28 and its homologue lin-28b in epithelial ovarian cancer and their associations with disease outcomes and expression of let-7a and IGF-II", Eur J Cancer 45(12) 2212-2218 (2009).
Macrae et al., "Structural basis for double-stranded RNA processing by Dicer", Science 311(5758) 195-198 (2006).
Michlewski et al., "Posttranscriptional regulation of miRNAs harboring conserved terminal loops", Mol Cell 32(3) 383-393 (2008).
Michlewski Et al., "Antagonistic role of hnRNP A1 and KSRP in the regulation of let-7a biogenesis", Nat Struct Mol Biol 17(8) 1011-1018 (2010).
Moss et al., "The cold shock domain protein LIN-28 controls developmental timing in C. elegans and is regulated by the lin-4 RNA", Cell 88(5) 637-646 (1997).
Ong et al., "Genetic variation in LIN28B is associated with the timing of puberty", Nat Genet 41(6) 729-733 (2009).
Peng et al., "Pluripotency factors Lin28 and Oct4 identify a sub-population of stem cell-like cells in ovarian cancer", Oncogene 29(14) 2153-2159 (2010).
Peng et al., "Genome-wide studies reveal that Lin28 enhances the translation of genes important for growth and survival of human embryonic stem cells", Stem Cells 29(3) 496-504 (2011).
Permuth-Wey et al., "LIN28B polymorphisms influence susceptibility to epithelial ovarian cancer", Cancer Res 71(11) 3896-3903 (2011).
Piskounova et al., "Determinants of microRNA processing inhibition by the developmentally regulated RNA-binding protein Lin28", J Biol Cehm 283(31) 21310-21314 (2008).
Qiu et al., "Lin28-mediated post-transcriptional regulation of Oct4 expression in human embryonic stem cells", Nucelic Acids Res 38(4) 1240-1248 (2010).
Rybak et al., "A feedback loop comprising lin-28 and let-7 controls pre-let-7 maturation during neural stem-cell commitment", Nat Cell Biol 10(8) 987-993 (2008).
Siomi et al., "Posttranscriptional regulation of microRNA biogenesis in animals", Mol Cell 38(3) 323-332 (2010).
Viswanathan et al., "Posttranscriptional regulation of microRNA biogenesis in animals", Science 320(5872) 97-100 (2008).
Viswanathan et al., "Lin28 promotes transformation and is associated with advanced human malignancies", Nat Genet 41(7) 843-848 (2009).
Viswanathan et al., "Lin28: A microRNA regulator with a macro role", Cell 140(4) 445-449 (2010).
Yang et al., "Temporally regulated expression of Lin-28 in diverse tissues of the developing mouse", Gene Expr Patterns 3(6) 719-726 (2003).
Yu et al., "let-7 regulates self renewal and tumorigenicity of breast cancer cells", Cell 131(6) 1109-1123 (2007).
Zeng et al., "Sequence requirements for micro RNA processing and function in human cells", RNA 9(1) 112-123 (2003).
Zeng et al., "Recognition and cleavage of primary microRNA precursors by the nuclear processing enzyme Drosha", EMBO J 24(1) 138-148 (2005).
Zeng et al., "Efficient processing of primary microRNA hairpins by Drosha requires flanking nonstructured RNA sequences", J Biol Chem 280(30) 27595-27603 (2005).
Zhang et al., "The terminal loop region controls microRNA processing by Drosha and Dicer", Nucleic Acids Res 38(21) 7689-7697 (2010).
Zhu et al., "Lin28a transgenic mice manifest size and puberty phenotypes identified in human genetic association studies", Nat Genet 42(7) 626-630 (2010).

SEQ ID NOS: 72-79, 16, and 80-83, respectively, in order of appearance

Figure 3

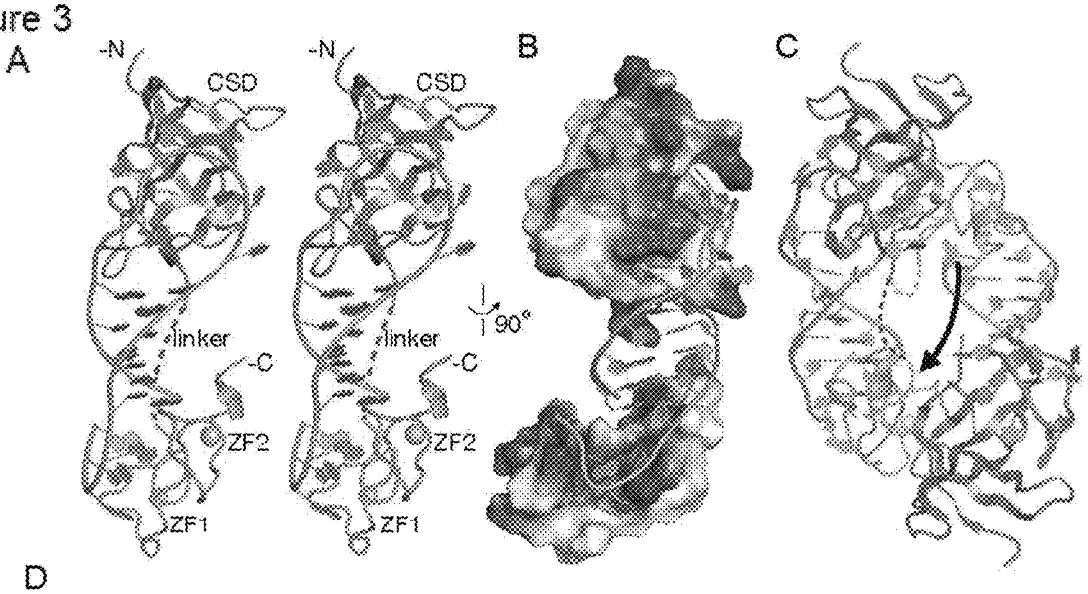

D

| | Lin28:preE$_M$-let-**7d** Native | Lin28:preE$_M$-let-**7d** Zn-SAD | Lin28:preE$_M$-let-**7f-1** Native | Lin28:preE$_M$-let-**7g** Native |
|---|---|---|---|---|
| Data collection[a] | | | | |
| Beamline | NSLS x25 | NSLS x25 | NSLS x25 | APS 24-ID-C |
| Resolution (Å) | 66.6-2.9 (2.910-2.900) | 70.0-3.22 (3.230-3.220) | 73-2.76 (2.772- 2.763) | 25.8-2.01 (2.014-2.007) |
| Space Group | $P4_32_12$ | $P4_32_12$ | $P4_12_12$ | $C222_1$ |
| Wavelength (Å) | 1.0000 | 1.2549 | 0.9795 | 0.9795 |
| Unit cell (Å) | a=b=143.8, c=177.7 | a=b=144.0, c=179.0 | a=b=139.9, c=85.6 | a=46.0, b=109.2, c=182.9 |
| $R_{symm}$[b] | 0.071 (0.586) | 0.109 (0.622) | 0.06 (0.629) | 0.046 (0.433) |
| I / σ(I) | 21.4 (3.2) | 21.3 (4.4) | 28.2 (3.3) | 18.9 (2.1) |
| Completeness (%) | 98.5 (99.8) | 99.9 (100)* | 100 (100) | 98.3 (92.5) |
| Redundancy | 5.6 (5.5) | 4.6 (4.6)* | 8 (8.3) | 3.2 (2.4) |
| Mosaicity (°) | 0.145 | 0.187 | 0.103 | 0.164 |
| Phasing | | | | |
| Mean FOM, initial | | 0.32 | | |
| Mean FOM, after NCS and DM[c] | | 0.65 | | |
| Refinement | | | | |
| $R_{work}/R_{free}$ (%)[d] | 17.93/20.80 | | 19.30/21.45 | 18.95/21.73 |
| Test Size | 2086 (5.06%) | | 1148 (5.15%) | 1550 (5%) |
| Number of complexes in ASU | 6 | | 2 | 2 |
| Average B /Wilson (Å$^2$) | 70.3 / 83.2 | | 74.8 / 78.1 | 49.6 / 40.3 |
| Ramachandran (%)[e] | 88.1 / 11.9 / 0 / 0 | | 88.2 / 11.8 / 0 / 0 | 93.2 / 6.8 / 0 / 0 |
| Rmsd Bond Length (Å) | 0.01 | | 0.01 | 0.01 |
| Rmsd Bond Angles (°) | 1.42 | | 1.36 | 1.25 |
| Peptide Omega Torsion (°) | 3.35 | | 3.4 | 3.60 |
| Other Torsion (°) | 24.89 | | 22.23 | 19.58 |
| solvent content | 0.681 | | 0.759 | 0.559 |

[a]Data for the outermost shell are given in parentheses, and asterisks reflect anomalous.

[b]$R_{symm} = 100 \sum |Ih - \langle Ih \rangle| / \sum Ih$, where <Ih> is the average intensity over symmetry equivalents.

[c]Figure of merit after non-crystallographic symmetry averaging over six copies and density modification in AutoSol/RESOLVE.

[d]$R_{work\ or\ free} = 100 \sum |F_o - F_c| / \sum |F_o|$. $R_{work}$ and $R_{free}$ were calculated from the working and test sets, respectively.

[e]Ramachandran (%) is given for each 1:1 complex, favorable/allowed/generously allowed/disallowed regions, respectively.

Figure 4

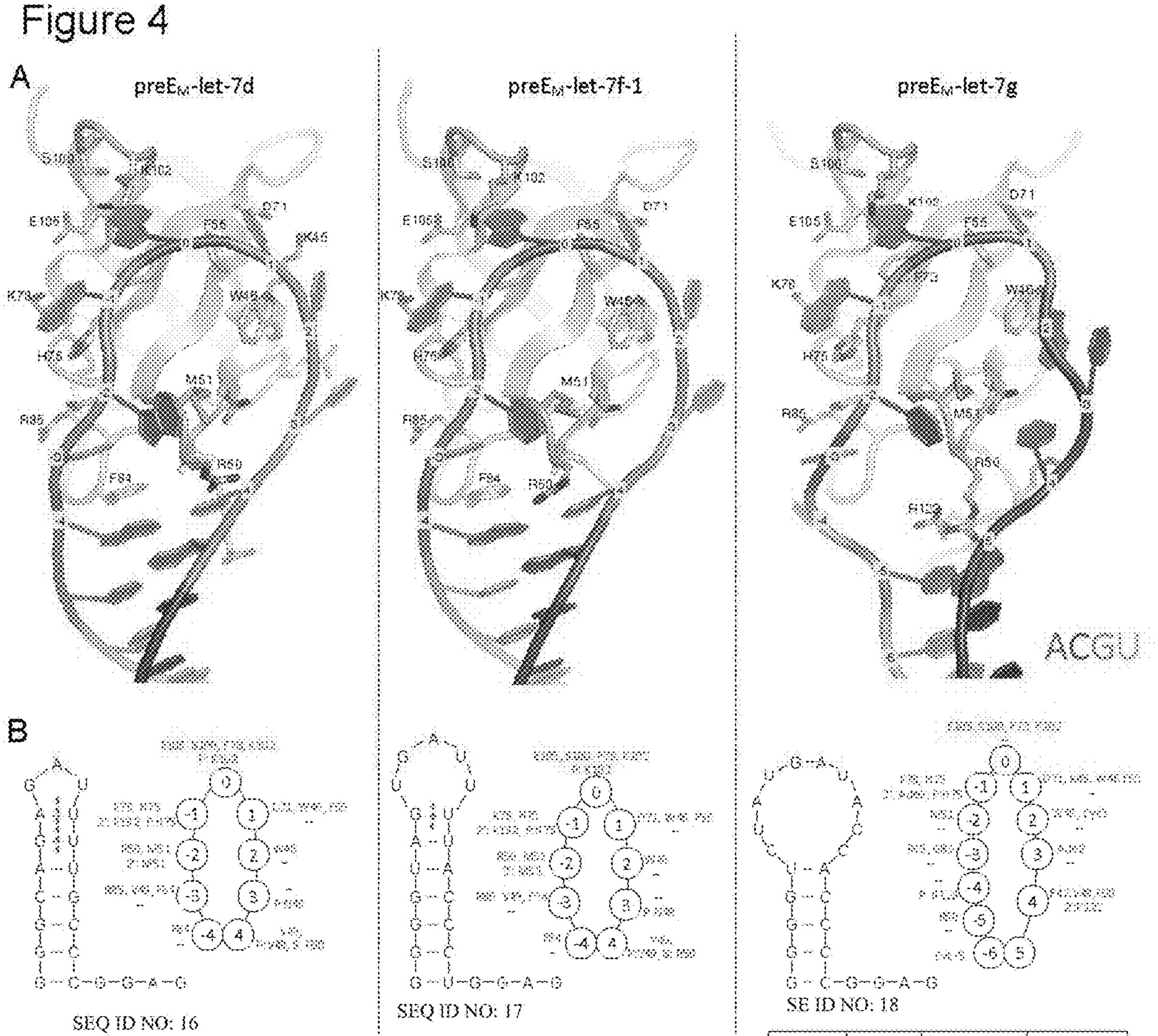

C

| preE | position | mutation | score |
|---|---|---|---|
| d | | WT | ++++ |
| d | -3 | G to A | + |
| d | -1 | G to A | + |
| d | 0 | A to G | +++ |
| d | 1 | U to A | + |

| preE | position | mutation | score |
|---|---|---|---|
| f-1 | | WT | ++++ |
| f-1 | -3 | G to A | + |
| f-1 | -1 | G to A | ++ |
| f-1 | 0 | A to G | +++ |
| f-1 | 0 | A to U | ++ |
| f-1 | 1 | U to A | + |
| f-1 | 1 | U to C | +++ |

| preE | position | mutation | score |
|---|---|---|---|
| g | | WT | ++++ |
| g | -3 | A to G | ++++ |
| g | -1 | G to A | +++ |
| g | 0 | A to G | +++ |
| g | 1 | U to G | + |

```
position   432101234
d          GGGCAGAGAUUUUGCCC GGAG
f-1        GGGGUAGUGAUUUUACCCUGGAG
g          GGGGUCUAUGAUACCACCCCGGAG
```

SEQ ID NOS 16-18, respectively, in order of appearance

| RNA mutation | origin | position | score |
|---|---|---|---|
| WT | pre-let-7g | | ++++ |
| G to C | pre-let-7g | -1 | ++++ |
| U to A | pre-let-7g | 1 | +++ |
| GAU to CAA | pre-let-7g | -1, 1 | ++ |
| GAU to CUA | pre-let-7g | -1, 0, 1 | ++ |
| deletion (Δ3) | pre-let-7g | -1, 0, 1 | + |
| GGAG to UGAG | pre-let-7g | GGAG | +++ |
| GGAG to GGAU | pre-let-7g | GGAG | + |
| deletion (ΔGGAG) | pre-let-7g | GGAG | + |
| WT | pre-miR-21 | | - |

B

| Protein mutation | position | score |
|---|---|---|
| WT | | ++++ |
| D71G | CSD | +++ |
| F73A | CSD | ++ |
| W46A | CSD | - |
| M51A | CSD | ++++ |
| Y140A | CCHCx2 | +++ |

C

| RNA mutation (pre-let-7g) | Protein mutation | score |
|---|---|---|
| WT | D71G | +++ |
| U to A | D71G | +++ |
| WT | F73A | ++ |
| Δ3 | F73A | + |
| GGAG to GGAU | F73A | - |
| ΔGGAG | F73A | - |
| WT | Y140A | +++ |
| Δ3 | Y140A | - |
| GGAU | Y140A | + |
| ΔGGAG | Y140A | ++ |
| WT | CSD only | **** |
| Δ3 | CSD only | - |
| GGAG to GGAU | CSD only | *** |
| ΔGGAG | CSD only | **** |
| WT | CCHCx2 only | **** |
| Δ3 | CCHCx2 only | **** |
| GGAG to GGAU | CCHCx2 only | - |
| ΔGGAG | CCHCx2 only | - |

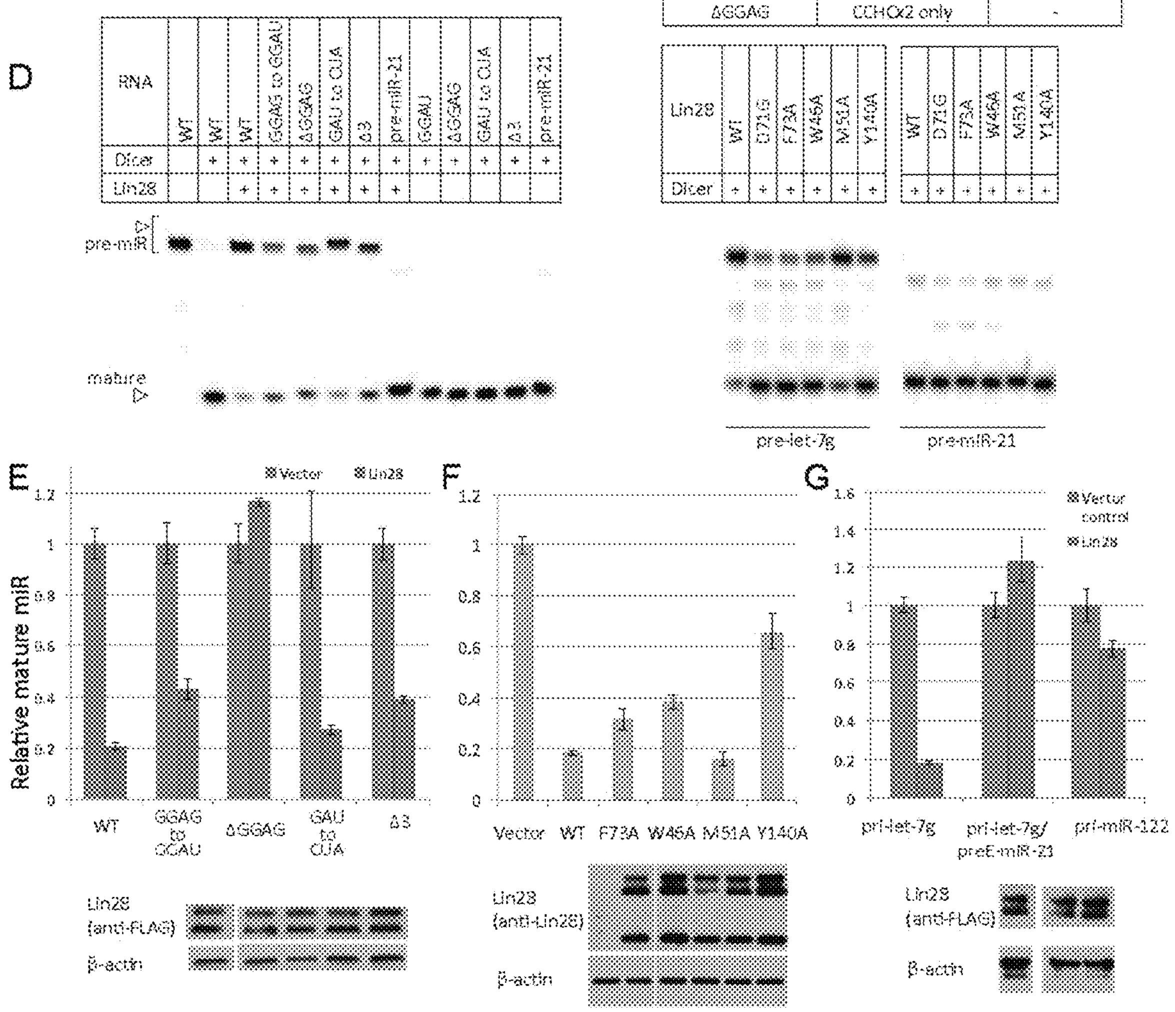

SEQ ID NOS 88-104, respectively in order of appearance

SEQ ID NOS 72-79,16, and 80-83, respectively in order of appearance

E

| Protein | RNA | partial specific volume (mL/g) | Calculated molecular weight for 1:1 complex (kDa) | Measured molecular weight (kDa) | Oligomeric state |
|---|---|---|---|---|---|
| Wildtype linker (Lin28 16-184) | Full-length preE-let-7d | 0.6789 | 28.3 | 30.5 ± 0.4 | monomeric |
| Lin28ΔΔ | Full-length preE-let-7d | 0.6744 | 25.9 | 27.2 ± 0.5 | monomeric |
| Lin28ΔΔ | preE$_M$-let-7d | 0.6872 | 23.1 | 25.4 ± 0.6 | monomeric |

| | RNA mutation | origin | position | score |
|---|---|---|---|---|
| 1 | WT | pre-let-7g | | ++++ |
| 2 | G to C | pre-let-7g | -1 | ++++ |
| 3 | U to A | pre-let-7g | 1 | +++ |
| 4 | GAU to CAA | pre-let-7g | -1, 1 | ++ |
| 5 | GAU to CUA | pre-let-7g | -1, 0, 1 | ++ |
| 6 | deletion (Δ3) | pre-let-7g | -1, 0, 1 | + |
| 7 | GGAG to UGAG | pre-let-7g | GGAG | +++ |
| 8 | GGAG to GGAU | pre-let-7g | GGAG | + |
| 9 | deletion (ΔGGAG) | pre-let-7g | GGAG | + |
| 10 | WT | pre-miR-21 | | - |

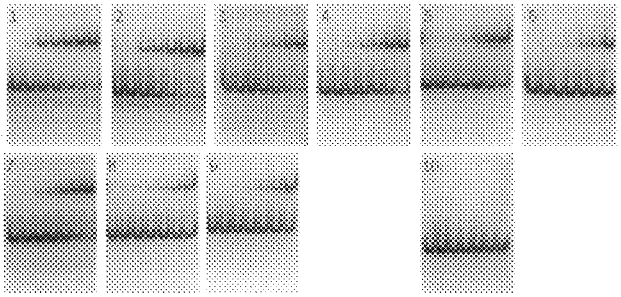

B

| | Protein mutation | position | score |
|---|---|---|---|
| 11 | WT | | ++++ |
| 12 | D71G | CSD | +++ |
| 13 | F73A | CSD | ++ |
| 14 | W46A | CSD | - |
| 15 | M51A | CSD | ++++ |
| 16 | Y140A | CCHCx2 | +++ |

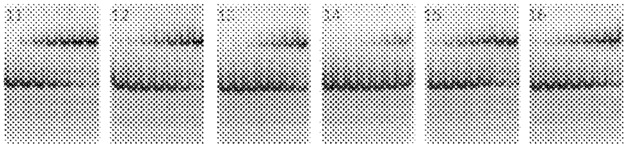

C

| | RNA mutation (pre-let-7g) | Protein mutation | score |
|---|---|---|---|
| 17 | WT | D71G | +++ |
| 18 | U to A | D71G | +++ |
| 19 | WT | F73A | ++ |
| 20 | Δ3 | F73A | + |
| 21 | GGAG to GGAU | F73A | - |
| 22 | ΔGGAG | F73A | - |
| 23 | WT | Y140A | +++ |
| 24 | Δ3 | Y140A | - |
| 25 | GGAU | Y140A | + |
| 26 | ΔGGAG | Y140A | ++ |
| 27 | WT | CSD | **** |
| 28 | Δ3 | CSD | - |
| 29 | GGAG to GGAU | CSD | *** |
| 30 | ΔGGAG | CSD | **** |
| 31 | WT | CCHCx2 | **** |
| 32 | Δ3 | CCHCx2 | **** |
| 33 | GGAG to GGAU | CCHCx2 | - |
| 34 | ΔGGAG | CCHCx2 | |

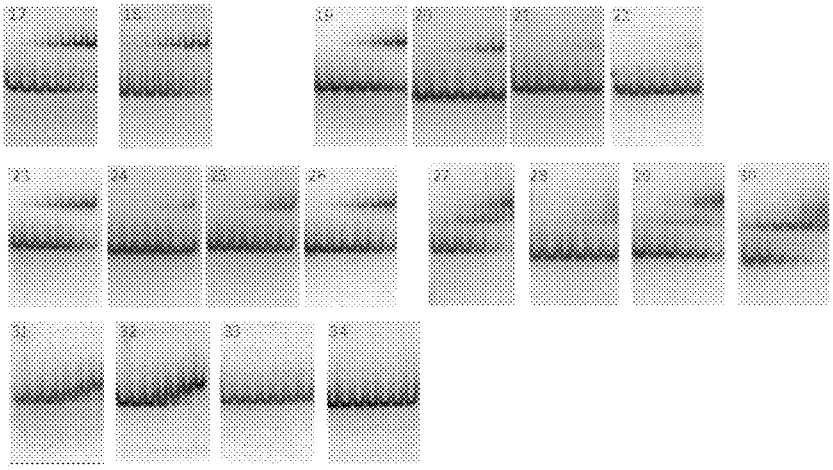

D

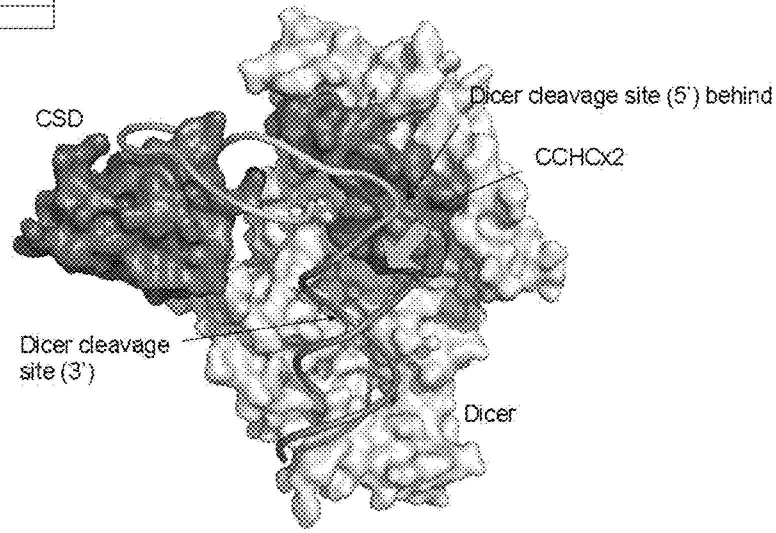

LIN28/LET-7 CRYSTAL STRUCTURES, PURIFICATION PROTOCOLS, AND MOLECULAR PROBES SUITABLE FOR SCREENING ASSAYS AND THERAPEUTICS

CROSS REFERENCE TO RELATED APPLICATIONS

This application is a Continuation Application of U.S. Ser. No. 15/984,109, filed May 18, 2018, which is a Continuation of U.S. Ser. No. 15/420,571 filed Jan. 31, 2017, now a U.S. Pat. No. 10,000,756 issued Jun. 19, 2018, which is a Continuation Application of U.S. Ser. No. 14/357,020 filed May 8, 2014, now U.S. Pat. No. 9,593,141 issued Mar. 14, 2017, which is a 35 U.S.C. § 371 National Phase Entry Application of International Application No. PCT/US2012/064412 filed Nov. 9, 2012, which designates the U.S., and which claims benefit under 35 U.S.C. § 119(e) of the U.S. Provisional Application No. 61/557,655, filed Nov. 9, 2011, the contents of which are incorporated herein by reference in their entireties.

GOVERNMENT SUPPORT

This invention was made with government support under grant no. 5U54GM094608 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 27, 2017, is named 28672131.txt and is 69,026 bytes in size.

FIELD OF THE INVENTION

The invention relates generally to compositions and methods to regulate microRNA (miRNA) biogenesis. The invention also relates to compositions and methods for treating or preventing cancer in a subject in need thereof.

REFERENCES TO TABLES

This application includes as part of the originally filed subject matter three (3) compact discs, labeled "Copy 1" "Copy 2" and "Copy 3" containing three (3) text files for three (3) separate lengthy tables, which are named "002806072131_TABLE_Uxt" (1,484 KB, created Nov. 9, 2012), "002806072131_TABLE2._txt" (541 KB, created Nov. 9, 2012), and "002806072131_TABLE_3.txt" (573 KB, created Nov. 9, 2012). The machine format of the compact discs ("Copy 1" "Copy 2" and "Copy 3") is IBM-PC and the operating system of the compact disc is MS-Windows. The content of the compact disc labeled "Copy 1" "Copy 2" and "Copy 3" is hereby incorporated by reference herein in its entirety. The information recorded on Copy 1 is identical to the information recorded on Copy 2 and Copy 3.

LENGTHY TABLES

The specification includes three (3) lengthy Tables; Table 1, Table 2, and Table 3. Lengthy Table 1 is the coordinates and structure factors for the structures of Lin28:preE$_M$-let-7 and is provided herein in an electronic format on a CD, as file "002806072131_TABLE_1.txt". Table 1 discloses SEQ ID NOS 118, 119, 111, 119, 111, 119, 111, 119, 111, 119, 111, 119, 111, 112, 112, 112, 112, 112, 112, 113, 113, 113, 113, 113, 113, 118, 118, 118, 118, 118, 118, 120, 121, 120, 121, 120, 121, 120, 121, 120, 121, 120, 121, 118, 118, 118, 118, 118, and 118, respectively, in order of appearance. Lengthy Table 2 is the coordinates and structure factors for the structures of Lin28:preE$_M$-let-7f-1 and is provided herein in an electronic format on a CD, as file "002806072131_TABLE_2.txt". Table 2 discloses SEQ ID NOS 17, 111, 111, 112, 112, 113, 113, 17, 17, 117, 115, 117, 115, 17, and 17, respectively, in order of appearance. Lengthy Table 3 is the coordinates and structure factors for the structures of Lin28:preE$_M$-let-7g and is provided herein in an electronic format on a CD, as file "002806072131_TABLE_3.txt". Table 3 discloses SEQ ID NOS 18, 111, 111, 112, 112, 113, 113, 18, 18, 114, 115, 116, 115, 18, and 18, respectively, in order of appearance. Table 1, Table 2, and Table 3 provided herein in an electronic format on a CD, as files "002806072131_TABLE_1.txt"; "002806072131_TABLE_2.txt"; and "002806072131_TABLE_3.txt" respectively are incorporated herein by reference in their entirety. Please refer to the end of the specification for access instructions.

BACKGROUND

Since the discovery of the first human microRNAs (miRNAs) about a decade ago, examples of miRNA regulation have been found for virtually every cellular process (Kim et al., 2009, Krol et al., 2010). Precursors of miRNAs undergo a series of processing steps after transcription to generate an active product. In this canonical pathway, a newly transcribed primary miRNA (pri-miRNA) with at least one hairpin structure is cleaved within the nucleus by an RNAseIII enzyme, Drosha, that acts in complex with DGCR8. The resulting pre-miRNA is exported to the cytoplasm, where another RNAseIII, Dicer, removes the "terminal loop region", or pre-element (preE), to yield the mature miRNA (FIG. 1A). Mechanisms of transcriptional control have been analyzed for many miRNAs, but the recent identification of post-transcriptional regulators of miRNA biogenesis now provides a way to investigate the molecular details of miRNA maturation and regulation (Davis-Dusenbery and Hata, 2010,Siomi and Siomi, 2010).

The let-7 family of miRNAs regulates many factors that control cell fate decisions, including oncogenes (c-Myc, Ras, HMGA-2) and cell cycle factors (CyclinD1, D2) (Bussing et al., 2008, Viswanathan and Daley, 2010). Deregulation of let-7 influences tumorigenicity of breast cancer stem cells (Yu et al., 2007a). Moreover, IL-6 is a target of let-7, thereby bridging the inflammation and cell-transformation signaling pathways (Iliopoulos et al., 2009). There are several let-7 family members in mammals, with similar mature regions but divergent sequences in the preE removed by Dicer (FIG. 1A). The preEs comprise low sequence identity and thus a minimum motif, i.e., minimal structural elements (stem, bulge, and loop), that are important for regulation of pre-miRNAs are not known (FIG. 1B).

Lin28, originally discovered as a heterochronic gene regulating developmental timing in worms (Moss et al., 1997), blocks let-7 biogenesis (Heo et al., 2008, Lehrbach et al., 2009, Newman et al., 2008, Rybak et al., 2008, Viswanathan et al., 2008). Its effects on gene expression are profound enough to make Lin28 one of the four factors sufficient to reprogram human somatic cells into induced pluripotent stem (iPS) cells (Yu et al., 2007b). Lin28 is activated in many human tumors (~15%) and appears to be associated with less differentiated cancers (Viswanathan et al., 2009). Studies with patient samples show correlation between over-expression or mutation of Lin28 with ovarian cancer (Peng et al., 2010, Permuth-Wey et al., 2011) and colon cancer (King et al., 2011). Variations in Lin28 have also been linked to developmental traits such as height and timing of puberty onset in humans and mice (Lettre et al., 2008, Lu et al., 2009, Ong et al., 2009, Perry et al., 2009, Sulem et al., 2009, Zhu et al., 2010).

Because it is one of few specific inhibitors of miRNA maturation to be discovered thus far, understanding Lin28 activity provides an avenue for investigating the mechanisms of miRNA biogenesis and regulation. Lin28 contains two well-known nucleic acid interaction domains—a cold shock domain (CSD) and two tandem Cys-Cys-His-Cys (CCHC)-type zinc-binding motifs (CCHCx2). Mammals have two paralogs, Lin28a and Lin28b, with different physiological expression patterns but similar behavior in vitro (Guo et al., 2006, Heo et al., 2008, Viswanathan et al., 2008, Yang and Moss, 2003). Lin28 binds precursor forms of let-7 miRNAs and can inhibit both pri-let-7 processing by Drosha (Newman et al., 2008, Viswanathan et al., 2008) and pre-let-7 processing by Dicer (Heo et al., 2008, Lehrbach et al., 2009, Rybak et al., 2008). Furthermore, Lin28 can recruit a terminal uridylyl transferase (TUTase) that adds uridine to the 3' end of pre-miRNA to increase decay (Hagan et al., 2009, Heo et al., 2009, Lehrbach et al., 2009). Although parts of the preE segment are dispensable for pri-miRNA processing by Drosha (Han et al., 2006), point mutations in the preE can disrupt interactions with Lin28 (Heo et al., 2009, Lehrbach et al., 2009, Newman et al., 2008, Piskounova et al., 2008), thereby de-repressing Drosha-mediated processing (Newman et al., 2008). Sequence variability among preEs in let-7 (FIG. 8A) has hindered interpretation of these results and extension of the conclusions to other let-7s, highlighting the need for an atomic-level view of divergent Lin28:let-7 complexes.

Accordingly, there is need in the art for inhibitors of Lin28 polypeptide activity.

SUMMARY

In one aspect, the invention provides a RNA oligonucleotide or analog, derivative, or pharmaceutically acceptable salt thereof, the oligonucleotide: (a) a nucleotide sequence of formula 5'-$N^1N^2N^3N^4N^5N^6N^7N^8N^9$-3', wherein $N^2$, $N^4$, and $N^5$ are independently a purine; $N^6$ is a pyrimidine; $N^1$, $N^3$, $N^7$, $N^8$, and $N^9$ are independently any nucleotide; and (b) a nucleotide sequence of 5'-GGAG-3', wherein the sequence 5'-GGAG-3' is linked to the 3' of the sequence of formula 5'-$N^1N^2N^3N^4N^5N^6N^7N^8N^9$-3', wherein there are from 0 to 100 nucleotides between the 3' end of 5'-$N^1N^2N^3N^4N^5N^6N^7N^8N^9$-3' and 5' end of the sequence 5'-GGAG-3', and the sequence 5'-GGAG-3' is single-stranded.

In some embodiments, there are 0-10 (e.g., 0, 1, 2, 3, 4, 5, 6, 7, 8, 9, or 10) nucleotides between the 3' end of 5'-$N^1N^2N^3N^4N^5N^6N^7N^8N^9$-3' and 5' end of the sequence 5'-GGAG-3', and the sequence 5'-GGAG-3' is single-stranded.

In some embodiments, the oligonucleotide comprises a hairpin structure comprising a hairpin loop and wherein $N^4$, $N^5$, and $N^6$ are in the loop region of the hairpin.

In another aspect, the invention provides a method for promoting miRNA processing of pri-miRNA to mature miRNA in a cell by contacting a cell with an oligonucleotide described herein.

In yet another aspect, the invention provides a method for treating or preventing a cancer by administering a therapeutically effective amount to a subject in need thereof.

In still yet another aspect, the invention provides an isolated polypeptide comprising amino acids 31-187 of full length Lin28A or Lin28B polypeptide, wherein the isolated polypeptide is less than 200 amino acids in length. The isolated polypeptide is also referred to as Lin28 fragment herein. Lin28 is functional in the presence of two zinc atoms which stabilize the two zinc finger domains (CCHCx2) in the Lin28. Accordingly, in some embodiments, two $Zn^{2+}$ atoms are bound with the isolated Lin28 or Lin28B polypeptide.

The invention also provides a crystalline molecule or molecular complex comprising a binding pocket of Lin28, wherein the Lin28 binding pocket is defined by structure coordinates binding pocket of Table 1, 2, or 3 and said Table 1, 2, or 3 being optionally varied by a rmsd of less than 1.5 Å or selected coordinates thereof.

Also provided herein is a screening assay for determining inhibitors of Lin28 activity by contacting a test compound with Lin28 fragment described herein and selecting the compound that increases level of mature let-7 miRNA relative to a control or inhibits the activity of Lin28 fragment relative to a control.

Provided herein are also method for purification of Lin28 and Lin28/Let-7 complexes.

BRIEF DESCRIPTION OF THE DRAWINGS

FIG. 3. Structure of Lin28:preE$_M$-let-7d complex. Cartoon representations were colored by domain: blue, CSD; green, CCHCx2; grey, zinc; orange, RNA. (A) Stereo representation of the monomeric complex. Interdomain linker is represented by a purple dotted line. (B) Same complex in (A) represented with surface colored by electrostatic potential, and rotated. (C) Domain-swapped dimer. Arrow pointing from the domain-swapped to the biologically relevant CCHCx2 domain. Linker connecting swapped domains marked in green, dotted line. Linker connecting unswapped domains marked in purple, dotted line. See also FIG. 10. (D) X-ray data collection and refinement statistics.

FIG. 4. CSD:RNA interactions. See also FIG. 11. (A) Close-up view of CSD (backbone as grey cartoon; key residues also shown with sticks and labels) interacting with the preE$_M$-loops as labeled, shown in the same orientation. RNA is colored by base identity (Azure, Ade; Crimson, Cyt; Green, Gua; Umber, Ura), and marked by position number on backbone as defined in text. (B) Schematic drawing of predicted structures of preE$_M$ sequences (SEQ ID NOS 16-18, respectively, in order of appearance) used for crystallization. Some of the predicted base pairs are broken (blue vertical dotted line) in the complex structures. Rings of circles show the protein:RNA interactions at each nucleotide position, marked with interacting residues (green, hydrophobic or π-stacking; red, H-bond). Top line is for base contacts and bottom line is for sugar or phosphate interactions at each position. (C) Comparison of Lin28 affinity for various preE$_M$-let-7 mutants, described by the parent let-7, position of the mutation, and the base identity. Accompanying gels are shown in FIG. 11. FIG. 4C discloses SEQ ID NOS 16-18, respectively, in order of appearance.

FIG. 6. Structure validation with full-length molecules (A-C) Results of EMSA with various RNA mutants (full-length pre-miRNA background) combined with protein mutants (full-length Lin28, except for the isolated-domain experiments, designated "CSD or CCHCx2 only"). Affinity indicated by Kd ranges: ++++, 0.13-0.26 μM; +++, 0.26-0.52 μM; ++, 0.52-1 μM; +,1-2 μM; –, >2 μM. For isolated domains, scores relative to wildtype are given by asterisks, as protein concentrations are higher than with full-length Lin28. See also FIG. S6. (D) In vitro Dicer processing assay with different pre-miR and protein combinations. (E-G) In vivo processing assay as described in FIG. 2D. Full-length Lin28 was co-transfected with pri-let-7g with indicated mutations (E), or with the entire preE region swapped with preE of an unrelated miR-21 (G) (Piskounova et al., 2008), or pri-miR-122 (G). Wildtype pri-let-7g was co-transfected with full-length Lin28 constructs with indicated mutations in (F). Error bars indicate standard deviation calculated from triplicate measurements. Immunoblots are shown to compare expression levels of Lin28 in each panel.

FIG. 13. Interactions of full-length Lin28 with full-length pre-let-7, related to FIG. 6. (A-C) EMSA using full-length molecules. Gels to accompany the tables shown in main FIG. 6 are shown here, ordered left to right and top to bottom, according to the order in each table. (D) Model of the Lin28:pre-let-7 complex binding to Dicer. Dicer and dsRNA substrate complex was modeled as referenced in text. The composite model with Lin28:preE-let-7 was generated by connecting the preE structure to an ideal dsRNA helix, connected by a flexible pink linker. Due to the limited number of bases on the 5' region of preE (hidden behind CCHCx2), Lin28:preE-let-7 crystal structure portion cannot be peeled away from Dicer more without melting much of the mature region (grey loops). The direction of CCHCx2 to wedge into the dsRNA is shown with a green arrow. Both CCHCx2 protein volume and unmodeled linker between CSD and CCHCx2 would clash with Dicer, as shown with a red arrow. (Blue, CSD; Green, CCHCx2; Orange and Yellow, preE-let-7f-1 included in crystal structure, orange is for direct contacts with Lin28; Pink, preE-let-7f-1 not included in the structure; Grey loop, portion of mature region of pre-let-7; Grey surface, dsRBD and RNAseIIIb dimer from mouse Dicer).

DETAILED DESCRIPTION

Figure 1:
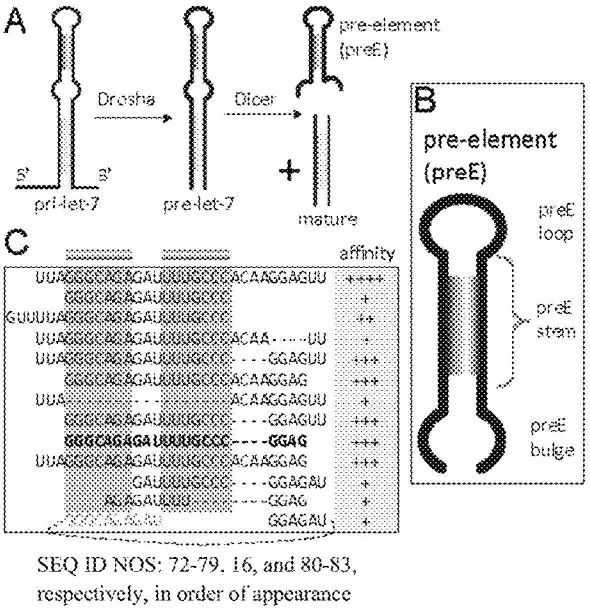
FIG. 1. Mapping of Lin28 binding sites on pre-let-7. (A) Processing steps in canonical miRNA biogenesis. Sequences shown are SEQ ID NOS: 72-79, 16, and 80-83, respectively, in order of appearance. (B) Architecture of pre-elements (preEs). (C) Fragments of preE-let-7d (SEQ ID NOS 72-79, 16, and 80-83, respectively, in order of appearance) tested on EMSA for association with Lin28. Affinity is indicated by Kd ranges: ++++, 0.2-1.5 μM; +++, 1.5-3 μM; ++, 3-15 μM; +, >15 μM. Predicted stem is highlighted in blue. Minimal fragment (preEM) identified is bolded. See also FIG. 8.

The inventors have discovered inter alia that neither the terminal nor the linker regions outside of the folded domains of Lin28 polypeptide are essential for blocking let-7 in vivo. The inventors have also discovered that a Lin28 polypeptide fragment comprising truncated N- and C-terminals and deletion in the linker is sufficient for binding to preE-let-7 in vitro. Accordingly, in one aspect, provided herein is an isolated Lin28 polypeptide fragment comprising, consisting or consisting essentially of amino acids 31-187 of a full length Lin28 polypeptide. A Lin28 fragment described herein also includes analogs, derivatives, and functional conservatives of said Lin28 fragment. As used herein, a Lin28 polypeptide encompasses both Lin28A and Lin28B polypeptides.

A Lin28 fragment described herein does not comprise the full length Lin28 polypeptide sequence. Accordingly, length of a Lin28 fragment described herein is at least one (e.g., 1, 2, 3, 4, 5, 6, 7, 8, 9, 10, 11, 12, 13, 14, 15, 16, 17, 18, 19, 20, 21, 22, 23, 24, 25, or more) amino acid less than the full length of Lin28A or Lin28B polypeptide. Generally, a Lin28 fragment described herein has a deletion of from 1 to 30 amino acids from the N-terminal or from 1 to 22 amino acids from the C-terminal of a full length Lin28 polypeptide.

In some embodiments, a Lin28 fragment described herein is less than 200 amino acids in length. In some embodiments, the Lin28 fragment is less than 175 amino acids in length.

In some embodiments, the Lin28 polypeptide fragment further comprises a deletion in the linker region of a full length Lin28 polypeptide. As used herein, the linker region of the Lin28 polypeptide refers to the amino acid sequence connecting the CSD and the first CCHC domain in the full length Lin28 polypeptide. Generally, the linker region is located between amino acid positions 121 to 138 of the full length Lin28 polypeptide. In some embodiments, the Lin28 polypeptide fragment comprises a deletion of 5, 6, 7, 8, 9, 10, 11, 12, 13, 14, 15, 16, 17, or 18 amino acids from the linker region. In some embodiments, Lin28 polypeptide fragment comprises deletion of amino acids 127 to 135 of the full length of a Lin28 polypeptide. In some embodiments, Lin28 polypeptide fragment comprises deletion of amino acids 121 to 135 of the full length of a Lin28 polypeptide.

In some embodiments, the Lin28 fragment comprises at least one (e.g., 1, 2, 3, 4, 5, 6, 7, 8, 9, 10, 11, 12, 13, 14, 15, 16, 17, 18, 19, 20, or more) amino acid residue selected from the group consisting of homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, desamino-Tyr, aminovaleric acid, pyroglutaminic acid, alpha-aminoisobutyric acid, gamma-aminobutyric acid, alpha-aminobutyric acid, alpha,gamma-aminobutyric acid, pyridylalanine, α-napthyalanine, β-napthyalanine, Ac-β-napthyalanine, $N^{\varepsilon}$-picoloyl-lysine, 4-halo-Phenyl, 4-pyrolidylalanine, isonipecotic carboxylic acid, and any combinations thereof.

In some embodiments, the Lin28 fragment comprises at least one (e.g., 1, 2, 3, 4, 5, 6, 7, 8, 9, 10, 11, 12, 13, 14, 15, 16, 17, 18, 19, 20, or more) D-amino acid. Without limitations, the D-amino acid can be present at any position in the Lin28 fragment. When more than one D-amino acids are present, they can be positioned next to or not next to each other. When three or more D-amino acids are present some of the D-amino acids can be present next to another D-amino acid while some of the D-amino acids are not next to another D-amino acid In some embodiments, the Lin28 fragment comprises a chemically modified amino acid. Such a chemically modified amino acid can be present at any position in the Lin 28 fragment. Additionally, when more than one chemically modified amino acids are present, they can be positioned next to or not next to each other. When three or more chemically modified amino acids are present some of the chemically modified amino acids can be present next to each other while some of the chemically modified amino are not next to another chemically modified amino acid. As used herein, the term "chemically modified amino acid" refers to an amino acid that has been treated with one or more reagents.

In some embodiments, the Lin28 fragment comprises at least one (e.g., 1, 2, 3, 4, 5, 6, 7, 8, 9, 10, 11, 12, 13, 14, 15, 16, 17, 18, 19, 20, or more) beta-amino acid. The beta-amino acid can be present at any position in the Lin28 fragment. Further, when more than one beta-amino acids are present, they can be positioned next to or not next to each other. When three or more beta-amino acids are present some of the beta-amino acids can be present next to another beta-amino acid while some of the beta-amino are not next to another beta-amino acid.

Exemplary beta-amino acids include, but are not limited to, L-β-Homoproline hydrochloride; (±)-3-(Boc-amino)-4-(4-biphenylyl)butyric acid; (±)-3-(Fmoc-amino)-2-phenylpropionic acid; (1S,3R)-(+)-3-(Boc-amino)cyclopentanecarboxylic acid; (2R,3R)-3-(Boc-amino)-2-hydroxy-4-phenylbutyric acid; (2S,3R)-3-(Boc-amino)-2-hydroxy-4-phenylbutyric acid; (R)-2-[(Boc-amino)methyl]-3-phenylpropionic acid; (R)-3-(Boc-amino)-2-methylpropionic acid; (R)-3-(Boc-amino)-2-phenylpropionic acid; (R)-3-(Boc-amino)-4-(2-naphthyl)butyric acid; (R)-3-(Boc-amino)-5-phenylpentanoic acid; (R)-3-(Fmoc-amino)-4-(2-naphthyl)butyric acid; (R)-(−)-Pyrrolidine-3-carboxylic acid; (R)-Boc-3,4-dimethoxy-β-Phe-OH; (R)-Boc-3-(3-pyridyl)-β-Ala-OH; (R)-Boc-3-(trifluoromethyl)-β-Phe-OH; (R)-Boc-3-cyano-β-Phe-OH; (R)-Boc-3-methoxy-β-Phe-OH; (R)-Boc-3-methyl-β-Phe-OH; (R)-Boc-4-(4-pyridyl)-β-Homoala-OH; (R)-Boc-4-(trifluoromethyl)-β-Homophe-OH; (R)-Boc-4-(trifluoromethyl)-β-Phe-OH; (R)-Boc-4-bromo-β-Phe-OH; (R)-Boc-4-chloro-β-Homophe-OH; (R)-Boc-4-chloro-β-Phe-OH; (R)-Boc-4-cyano-β-Homophe-OH; (R)-Boc-4-cyano-β-Phe-OH; (R)-Boc-4-fluoro-β-Phe-OH; (R)-Boc-4-methoxy-β-Phe-OH; (R)-Boc-4-methyl-β-Phe-OH; (R)-Boc-β-Tyr-OH; (R)-Fmoc-4-(3-pyridyl)-β-Homoala-OH; (R)-Fmoc-4-fluoro-β-Homophe-OH; (S)-(+)-Pyrrolidine-3-carboxylic acid; (S)-3-(Boc-amino)-2-methylpropionic acid; (S)-3-(Boc-amino)-4-(2-naphthyl)butyric acid; (S)-3-(Boc-amino)-5-phenylpentanoic acid; (S)-3-(Fmoc-amino)-2-methylpropionic acid; (S)-3-(Fmoc-amino)-4-(2-naphthyl)butyric acid; (S)-3-(Fmoc-amino)-5-hexenoic acid; (S)-3-(Fmoc-amino)-5-phenyl-pentanoic acid; (S)-3-(Fmoc-amino)-6-phenyl-5-hexenoic acid; (S)-Boc-2-(trifluoromethyl)-β-Homophe-OH; (S)-Boc-2-(trifluoromethyl)-β-Homophe-OH; (S)-Boc-2-(trifluoromethyl)-β-Phe-OH; (S)-Boc-2-cyano-β-Homophe-OH; (S)-Boc-2-methyl-β-Phe-OH; (S)-Boc-3,4-dimethoxy-β-Phe-OH; (S)-Boc-3-(trifluoromethyl)-β-Homophe-OH; (S)-Boc-3-(trifluoromethyl)-β-Phe-OH; (S)-Boc-3-methoxy-β-Phe-OH; (S)-Boc-3-methyl-β-Phe-OH; (S)-Boc-4-(4-pyridyl)-β-Homoala-OH; (S)-Boc-4-(trifluoromethyl)-β-Phe-OH; (S)-Boc-4-bromo-β-Phe-OH; (S)-Boc-4-chloro-β-Homophe-OH; (S)-Boc-4-chloro-β-Phe-OH; (S)-Boc-4-cyano-β-Homophe-OH; (S)-Boc-4-cyano-β-Phe-OH; (S)-Boc-4-fluoro-β-Phe-OH; (S)-Boc-4-iodo-β-Homophe-OH; (S)-Boc-4-methyl-β-Homophe-OH; (S)-Boc-4-methyl-β-Phe-OH; (S)-Boc-β-Tyr-OH; (S)-Boc-γ,γ-diphenyl-β-Homoala-OH; (S)-Fmoc-2-methyl-β-Homophe-OH; (S)-Fmoc-3,4-difluoro-β-Homophe-OH; (S)-Fmoc-3-(trifluoromethyl)-β-Homophe-OH; (S)-Fmoc-3-cyano-β-Homophe-OH; (S)-Fmoc-3-methyl-β-Homophe-OH; (S)-Fmoc-γ,γ-diphenyl-β-Homoala-OH; 2-(Boc-aminomethyl)phenylacetic acid; 3-Amino-3-(3-bromophenyl)propionic acid; 3-Amino-4,4,4-trifluorobutyric acid; 3-Aminobutanoic acid; DL-3-Aminoisobutyric acid; DL-β-Aminoisobutyric acid puriss; DL-β-Homoleucine; DL-β-Homomethionine; DL-β-Homophenylalanine; DL-β-Leucine; DL-β-Phenylalanine; L-β-Homoalanine hydrochloride; L-β-Homoglutamic acid hydrochloride; L-β-Homoglutamine hydrochloride; L-β-Homohydroxyproline hydrochloride; L-β-Homoisoleucine hydrochloride; L-β-Homoleucine hydrochloride; L-β-Homolysine dihydrochloride; L-β-Homomethionine hydrochloride; L-β-Homophenylalanine allyl ester hydrochloride; L-β-Homophenylalanine hydrochloride; L-β-Homoserine; L-β-Homothreonine; L-β-Homotryptophan hydrochloride; L-β-Homotyrosine hydrochloride; L-β-Leucine hydrochloride; Boc-D-β-Leu-OH; Boc-D-β-Phe-OH; Boc-$\beta^3$-Homopro-OH; Boc-β-Glu (OBzl)-OH; Boc-β-Homoarg(Tos)-OH; Boc-β-Homoglu (OBzl)-OH; Boc-β-Homohyp(Bzl)-OH (dicyclohexylammonium) salt technical; Boc-β-Homolys(Z)-OH; Boc-β-Homoser(Bzl)-OH; Boc-13-Homothr(Bzl)-OH; Boc-β-Homotyr(Bzl)-OH; Boc-β-Ala-OH; Boc-β-Gln-OH; Boc-β-Homoala-OAll; Boc-β-Homoala-OH; Boc-β-Homogln-OH; Boc-β-Homoile-OH; Boc-β-Homoleu-OH; Boc-β-Homomet-OH; Boc-β-Homophe-OH; Boc-β-Homotrp-OH; Boc-β-Homotrp-OMe; Boc-β-Leu-OH; Boc-β-Lys(Z)-OH (dicyclohexylammonium) salt; Boc-β-Phe-OH; Ethyl 3-(benzylamino)propionate; Fmoc-D-β-Homophe-OH; Fmoc-L-$\beta^3$-homoproline; Fmoc-β-D-Phe-OH; Fmoc-β-Gln (Trt)-OH; Fmoc-β-Glu(OtBu)-OH; Fmoc-β-Homoarg (Pmc)-OH; Fmoc-β-Homogln(Trt)-OH; Fmoc-β-Homoglu (OtBu)-OH; Fmoc-β-Homohyp(tBu)-OH; Fmoc-β-Homolys(Boc)-OH; Fmoc-β-Homoser(tBu)-OH; Fmoc-β-Homothr(tBu)-OH; Fmoc-β-Homotyr(tBu)-OH; Fmoc-β-Ala-OH; Fmoc-β-Gln-OH; Fmoc-β-Homoala-OH; Fmoc-β-Homogln-OH; Fmoc-β-Homoile-OH; Fmoc-β-Homoleu-OH; Fmoc-β-Homomet-OH; Fmoc-β-Homophe-OH; Fmoc-β-Homotrp-OH; Fmoc-β-Leu-OH; Fmoc-β-Phe-OH; N-Acetyl-DL-β-phenylalanine; Z-D-β-Dab(Boc)-OH; Z-D-β-Dab(Fmoc)-OH purum; Z-DL-β-Homoalanine; Z-β-D-Homoala-OH; Z-β-Glu(OtBu)-OH technical; Z-β-Homotrp (Boc)-OH; Z-β-Ala-OH purum; Z-β-Dab(Boc)-OH; Z-β-Dab(Fmoc)-OH; Z-β-Homoala-OH; β-Alanine; β-Alanine BioXtra; β-Alanine ethyl ester hydrochloride; β-Alanine methyl ester hydrochloride; β-Glutamic acid hydrochloride; cis-2-Amino-3-cyclopentene-1-carboxylic acid hydrochloride; cis-3-(Boc-amino)cyclohexanecarboxylic acid; and cis-3-(Fmoc-amino)cyclohexanecarboxylic acid.

In some embodiments, the Lin28 fragment comprises at least one (e.g., 1, 2, 3, 4, 5, 6, 7, 8, 9, 10, 11, 12, 13, 14, 15, 16, 17, 18, 19, 20, or more) modified peptide linkage, e.g., a peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. The peptide replacement linkage can be present at any position in the Lin2 fragment. When more than peptide replacement linkages are present, they can be positioned next to (e.g., on both sides of a given amino acid) or not next to each other (e.g., only one side of a given amino acid is linked via a peptide replacement linkage to the next amino acid).

In some embodiments, the N-terminus amino group of the Lin28 peptide conjugated with nitrogen- or amino-protecting group. As used herein, a "nitrogen protecting group" or an "amino protecting group" refers to moieties that block or mask the NH2 group. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Further amino protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991, content of which is herein incorporated by reference in its entirety.

In some embodiments, the N-terminus amino acid of the Lin28 fragment is acetylated or alkylated, e.g., with acetyl, ethanoyl, propionyl, t-butanoyl, methyl, ethyl, propyl, butyl, pentyl, or hexanyl.

In some embodiments, the N-terminus amino acid of the Lin28 fragment is conjugated with a tag amino acid sequence. Without wishing to be bound by a theory, a tag sequence makes it easy to synthesize and purify the polypeptide. In one embodiment, the tag amino acid sequence is MHHHHHHENLYFQ (SEQ ID NO: 1).

In some embodiments, the Lin28 fragment is conjugated with polyethylene glycol (PEG). Without wishing to be bound by theory, such conjugation can increase the in vivo half-life of the Lin28 fragment. As used herein, "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof. Methods of conjugating PEGs to peptides are well known in the art. A Lin28fragment can comprise a PEG at the N-terminus, C-terminus, or at an internal amino acid. The PEG can be linked to the N-terminus amino group, C-terminus carboxyl group, or to an amino, hydroxyl or thiol group on the side chain of an amino acid.

As Lin28 is functional in the presence of two Zinc atoms which stabilize two zinc finger domains (CCHCx2), in some embodiments, two divalent cations can be bound to the isolated Lin28 or Lin28B polypeptide described herein. As used in this application, the term "divalent cation" means a cation having a +2 charge. Exemplary divalent cations include, but are not limited to, zinc, cobalt, nickel, cadmium, magnesium, and manganese. In some embodiments, the divalent cation is $Zn^{2+}$.

In some embodiments, the Lin28 fragment is selected from the group consisting of:

(SEQ ID NO: 2)
MHHHHHHENLYFQGSGAAEKAPEEAPPDAARAADEPQLLHGAGICK
WFNVRMGFGFLSMTARAGVALDPPVDVFVHQSKLHMEGFRSLKEGE
AVEFTFKKSAKGLESIRVTGPGGVFCIGSERRPKGKNMQKRRSKGD
RCYNCGGLDHHAKECKLPPQPKKCHFCQSINHMVASCPLKAQQGPSS
(mouse Lin28A delta + tag);

(SEQ ID NO: 3)
MHHHHHHENLYFQGSGAADEPQLLHGAGICKWFNVRMGFGFLSMTAR
AGVALDPPVDVFVHQSKLHMEGFRSLKEGEAVEFTFKKSAKGLESIR
VTGPGGVFCIGSERRPKGGDRCYNCGGLDHHAKECKLPPQPKKCHFC
QSINHMVASCPLKAQQGPSSQGK
(mouse Lin28A delta delta + tag);

(SEQ ID NO: 4)
MHHHHHHENLYFQGSGEEPEKLPGLAEDEPQVLHGTGHCKWFNVRMG
FGFISMISREGNPLDIPVDVFVHQSKLFMEGFRSLKEGEPVEFTFKK
SPKGLESIRVTGPGGSPCLGSERRPKGKTLQKRKPKGDRWRRQDLLM

-continued

```
DQMWTVREEESRMIPRCYNCGGLDHHAKECSLPPQPKKCHYCQSIMH

MVANCPHKLAAQLPASS
(mouse Lin28B delta + tag);

                                    (SEQ ID NO: 5)
MHHHHHHENLYFQGSGAAEEAPEEAPEDAARAADEPQLLHGAGICKW

FNVRMGFGFLSMTARAGVALDPPVDVFVHQSKLHMEGFRSLKEGEAV

EFTFKKSAKGLESIRVTGPGGVFCIGSERRPKGKSMQKRRSKGDRCY

NCGGLDHHAKECKLPPQPKKCHFCQSISHMVASCPLKAQQGPSAQGK
(human Lin28A delta + tag);

                                    (SEQ ID NO: 6)
MHHHHHHENLYFQGSGAADEPQLLHGAGICKWFNVRMGFGFLSMTAR

AGVALDPPVDVFVHQSKLHMEGFRSLKEGEAVEFTFKKSAKGLESIR

VTGPGGVFCIGSERRPKGGDRCYNCGGLDHHAKECKLPPQPKKCHFC

QSISHMVASCPLKAQQGPSAQGK
(human Lin28A delta delta + tag),

                                    (SEQ ID NO: 7)
MHHHHHHENLYFQGSGEEPGKLPEPAEEESQVLRGTGHCKWFNVRMG

FGFISMINREGSPLDIPVDVFVHQSKLFMEGFRSLKEGEPVEFTFKK

SSKGLESIRVTGPGGSPCLGSERRPKGKTLQKRKPKGDRCYNCGGLD

HHAKECSLPPQPKKCHYCQSIMHMVANCPHKNVAQPPASSQGR
(human Lin28B delta + tag),

                                    (SEQ ID NO: 8)
MHHHHHHENLYFQGSGPAEEESQVLRGTGHCKWFNVRMGFGFISMIN

REGSPLDIPVDVFVHQSKLFMEGFRSLKEGEPVEFTFKKSSKGLESI

RVTGPGGSPCLGSERRPKGGDRCYNCGGLDHHAKECSLPPQPKKCHY

CQSIMHMVANCPHKNVAQPPASSQGR
(human Lin28B delta delta + tag),

                                    (SEQ ID NO: 9)
GSGAAEKAPEEAPPDAARAADEPQLLHGAGICKWFNVRMGFGFLSMT

ARAGVALDPPVDVFVHQSKLHMEGFRSLKEGEAVEFTFKKSAKGLES

IRVTGPGGVFCIGSERRPKGKNMQKRRSKGDRCYNCGGLDHHAKECK

LPPQPKKCHFCQSINHMVASCPLKAQQGPSS
(mouse Lin28A delta),

                                   (SEQ ID NO: 10)
GSGAADEPQLLHGAGICKWFNVRMGFGFLSMTARAGVALDPPVDVFV

HQSKLHMEGFRSLKEGEAVEFTFKKSAKGLESIRVTGPGGVFCIGSE

RRPKGGDRCYNCGGLDHHAKECKLPPQPKKCHFCQSINHMVASCPLK

AQQGPSSQGK
(mouse Lin28A delta delta),

                                   (SEQ ID NO: 11)
GSGEEPEKLPGLAEDEPQVLHGTGHCKWFNVRMGFGFISMISREGNP

LDIPVDVFVHQSKLFMEGFRSLKEGEPVEFTFKKSPKGLESIRVTGP

GGSPCLGSERRPKGKTLQKRKPKGDRWRRQDLLMDQMWTVREEESRM

IPRCYNCGGLDHHAKECSLPPQPKKCHYCQSIMHMVANCPHKLAAQL

PASS
(mouse Lin28B delta),

                                   (SEQ ID NO: 12)
GSGAAEEAPEEAPEDAARAADEPQLLHGAGICKWFNVRMGFGFLSMT

ARAGVALDPPVDVFVHQSKLHMEGFRSLKEGEAVEFTFKKSAKGLES
```

-continued

```
IRVTGPGGVFCIGSERRPKGKSMQKRRSKGDRCYNCGGLDHHAKECK

LPPQPKKCHFCQSISHMVASCPLKAQQGPSAQGK
(human Lin28A delta),

                                   (SEQ ID NO: 13)
GSGAADEPQLLHGAGICKWFNVRMGFGFLSMTARAGVALDPPVDVFV

HQSKLHMEGFRSLKEGEAVEFTFKKSAKGLESIRVTGPGGVFCIGSE

RRPKGGDRCYNCGGLDHHAKECKLPPQPKKCHFCQSISHMVASCPLK

AQQGPSAQGK
(human Lin28A delta delta),

                                   (SEQ ID NO: 14)
GSGEEPGKLPEPAEEESQVLRGTGHCKWFNVRMGFGFISMINREGSP

LDIPVDVFVHQSKLFMEGFRSLKEGEPVEFTFKKSSKGLESIRVTGP

GGSPCLGSERRPKGKTLQKRKPKGDRCYNCGGLDHHAKECSLPPQPK

KCHYCQSIMHMVANCPHKNVAQPPASSQGR
(human Lin28B delta),
and

                                   (SEQ ID NO: 15)
GSGPAEEESQVLRGTGHCKWFNVRMGFGFISMINREGSPLDIPVDVF

VHQSKLFMEGFRSLKEGEPVEFTFKKSSKGLESIRVT
(human Lin28B delta delta).
```

A Lin28 fragment described herein can be synthesized according to the usual methods of solution and solid phase peptide chemistry, or by classical methods known in the art. Purification of peptides is well known in the art and can be, for example, HPLC. Methods describing useful peptide synthesis and purification methods can be found, for example, in U.S. Patent Application No. 20060084607.

Lin28 fragments described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. Nos. 3,842,067 and 3,872,925, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego, #9830). Contents of all of the foregoing disclosures are incorporated herein by reference.

In some embodiments, Lin28 constructs, e.g., Lin28 constrcuts derived from mouse Lin28a, can be purified after overexpression in *E. coli*, using Nickel affinity, cation exchange, and size exclusion chromatography. For example, Lin28 constructs can be overexpressed in *E. coli* strain BL21(DE3) Rosetta pLysS. After initial affinity chromatography step using Ni-NTA beads (Qiagen), His-tags can be removed by incubating with recombinant TEV protease. After His-tag removal, the Lin28 constrcuts can be purified by cation exchange chromatography. Cation exchange chromatography can be performed using a HiTrap S (GE Healthcare) with a buffer containing 20 mM BisTris pH 6.0, 5 mM dithiothreitol (DTT), 5% glycerol, and 50 μM $ZnCl_2$, over 0.1-1M NaCl gradient. If desired, further purification of the Lin28 constructs can be accomplished by size exclusion chromatography. For example, size exclusion chromatography can be performed using Superdex 200 (GE Healthcare) in the same buffer as noted-above. In some embodiments, a Lin28 functional fragment can be synthesized and purified as described herein in Example 1.

Without wishing to be bound by a theory, a Lin28 fragment described herein can be used in place of the full length Lin28 polypeptide in methods requiring the use of a full length Lin28 polypeptide. As described herein, a Lin28 fragment can bind preE-let-7 both in vivo and in vitro. Thus, a Lin28 fragment described herein has similar preE-let-7 binding activity as the full length Lin28 polypeptide.

One method of producing induced pluripotent stem cells, comprises introducing a Lin28 polypeptide into a cell. Because a Lin28 fragment has the similar activity as the full length polypeptide, a Lin28 fragment of the invention can be used in methods of producing induced pluripotent stem cells. Exemplary methods of producing induced pluripotent stem cells using Lin28 are described for example in U.S. Pat. App. Pub. No. 2011/0117653, No. 2011/0200568, No. 2011/044961, No. 2011/0039338, No. 2010/0062533, No. 2011/0250692, No. 2011/0003365, No. 2011/0236966, No. 2011/0201110, No. 2011/0244566, No. 2011/0104805, No. 2011/0143436, No. 2011/0190729, No. 2010/0041054, No. 2010/0093092, and No. 2010/0120069, content of all of which is incorporated herein by reference. Without wishing to be bound by a theory, a Lin28 fragment disclosed herein can be used in place of a full length Lin28 polypeptide in the methods described in the above-noted references.

A Lin28 fragment described herein is sufficient for binding to preE-let-7 in vitro. Accordingly, the Lin28 fragment can be used for screening inhibitors of full length Lin28 polypeptide or agents that promote miRNA processing of pre-miRNA to mature miRNA. Accordingly, provided herein is a method for screening a test compound for inhibiting activity of Lin28 polypeptide or promoting processing of pre-miRNA to mature miRNA, the method comprising contacting a Lin28 fragment described herein with a test compound.

Alternatively, a test compound can be assessed for its ability to function as an inhibitor of Lin28 polypeptide by assessing the cell proliferation (or cell growth) of a cancer cell line, such as the H1299 lung adenocarcinoma or chronic myelogenous leukemia (CML) cell lines (as disclosed herein in the Examples) in the presence of the test compound inhibitor of Lin28. An decrease in the cell proliferation rate (or cell growth) in the presence of the inhibitor of Lin28 as compared to in the absence of an agent, or a negative control indicates the test compound functions as an inhibitor of Lin28. Alternatively, a substantially similar i.e. about at least 60%, or at least about 70%, or at least about 80% or at least about 90% or more cell proliferation rate (or cell growth) in the presence of the test compound inhibitor of Lin28 as compared to the presence of a positive control (i.e. an oligonucleotide described herein) indicates the test compound functions as an inhibitor of Lin28.

In some embodiments, the method further comprises selecting the compound that promotes processing of a pre-miRNA to a mature miRNA or that inhibits binding of oligonucleotide described herein, a pre-miRNA, or miRNA to the Lin28 fragment.

For the screening assays, the Lin28 fragment can be immobilized on a solid support. Polypeptides can be immobilized using methods known in the art, such as adsorption onto a plastic microtiter plate or specific binding of a GST-fusion protein to a polymeric bead containing glutathione. For example, a GST-Lin28 fragment can be bound to glutathione-Sepharose beads. The immobilized peptide is then contacted with the test compound.

As used herein, the term "test compound" refers to compounds and/or compositions that are to be screened for their ability to inhibit Lin28 activity or to promote miRNA processing. Test compounds may include a wide variety of different compounds, including chemical compounds, mixtures of chemical compounds, e.g., small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular mass equal to or less than 700 Daltons.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, Graffinity, Panvera, Vitas-M Lab, Biomol International and Oxford. Other known compound libraries include, NIH Clinical Collection 1 and 2, Biomol 4—FDA Approved Drugs, Sigma Lopac, Tocriscreen Mini Library, NINDS Custom Collection 2, Prestwick 2 Collection, MSDiscovery 1, Biomol ICCB Know Bioactives, Asinex 1, ChemBridge 3, ChemDiv 4 and 6, Life Chemicals 1, and Maybridge 4 and 5. These libraries can be screened using the screening devices and methods described herein. Chemical compound libraries such as those from NIH Roadmap, Molecular Libraries Screening Centers Network (MLSCN) can also be used. A comprehensive list of compound libraries can be found on the web at www.broad.harvard.edu/chembio/platform/screening/compound_libraries/index.htm.

A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

Generally, compounds can be tested at any concentration. In some embodiments, compounds are tested at a concentration in the range of from about 0.1 nM to about 1000 mM. Preferably the compound is tested in the range of from about 0.1 μM to about 10 μM.

Additionally, the test compound can be contacted with the Lin28 fragment for a sufficient time to allow the test compound to interact with the Lin28 fragment. For a non-limiting example, Lin28 fragment is incubated with the test compound for at least 15 minutes before assaying for activity.

In some embodiments, screening assay further comprises selecting the compound that inhibits or reduces Lin28 activity. The test compound can inhibit Lin28 activity by at least 10%, 20%, 30%, 40%, 50%, 50%, 70%, 80%, 90%, 95% or more relative to a control.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening methods are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic that features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with, such as Ephexin5. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound selected by the screening assay described herein. It is to be understood that analogs, derivatives, and isomers of the compounds selected by the screening assays described herein are also claimed herein.

The structural information disclosed herein is useful analysis of binding interactions with a ligand, e.g., for discovery of inhibitors of Lin28 polypeptide activity. Such data is useful for a number of purposes, including the generation of structures to analyze the mechanisms of action and/or to discover or perform rational drug design of active compounds. For example, a search of several small-molecule structural data bases such as Available Chemicals Directory, Cambridge Crystallographic Database, Fine Chemical Database and CONCORD database is carried out using parameters derived from the crystal structures described herein. The search can be 2-dimensional, 3-dimensional or both and can be done using a combination of software such as UNITY version 2.3.1 (Tripos, Inc.), MACCS 3D, CAVEAT and DOCK. Conformational flexibility of the small molecules is allowed. The strategy for conducting the search takes into account conformations and/or key residues in the combining site Structural information disclosed herein can be stored on a computer-readable medium. The invention therefore provides systems, particularly a computer system, the systems containing the atomic co-ordinate data of any one of the tables below, or selected co-ordinates thereof. The computer system can comprise: (i) a computer-readable data storage medium comprising data storage material encoded with the computer-readable data; (ii) a working memory for storing instructions for processing said computer-readable data; and (iii) a central-processing unit coupled to said working memory and to the computer-readable data storage medium for processing said computer-readable data and thereby generating structures and/or performing rational drug design. The computer system can further comprise a display coupled to the central-processing unit for displaying said structures. The computer system can contain one or more remote devices. The remote device may comprise e.g. a computer system or computer readable media of one of the previous aspects of the invention. The device can be in a different country or jurisdiction from where the computer-readable data is received. The communication with a remote device may be via the internet, intranet, and e-mail etc. . . . , transmitted through wires or by wireless means such as by terrestrial radio or by satellite. Typically the communication will be electronic in nature, but some, or all, of the communication pathway may be optical, for example, over optical fibers. The data received can then be used in a computer-based method for the analysis of the interaction of a ligand as discussed above.

Based on the elucidated structures of Lin28:preE-let-7 complexes, the inventors have discovered the minimum motif for an RNA oligonucleotide that can bind to a Lin28 polypeptide. The inventors have discovered that the sequence 5'-N1N2N3N4N5N6N7N8N9-3' provides the minimum domain capable of binding the CSD domain of Lin28 and the sequence 5'-GGAG-3' is sufficient for binding to the CCHC domain of Lin28. Further a linker of zero or more nucleotides in between the two sequences is sufficient to allow an oligonucleotide to bind with the Lin28.

Accordingly, provided herein is an RNA oligonucleotide comprising at least two different domains for binding to a Lin28 polypeptide. The oligonucleotide comprises: (a) a nucleotide sequence of formula 5'-N1N2N3N4N5N6N7N8N9-3', wherein N2, N4, and N5 are independently a purine; N6 is a pyrimidine; N1, N3, N7, N8, and N9 are independently any nucleotide; and (b) a single-stranded nucleotide sequence of 5'-GGAG-3', wherein the two sequences are linked to each other by a sequence of 0-100 nucleotides. Preferably, the sequence 5'-GGAG-3' is linked to the 3' end of the sequence 5'-N1N2N3N4N5N6N7N8N9-3'.

In some embodiments, the sequence 5'-N1N2N3N4N5N6N7N8N9-3' and the sequence 5'-GGAG-3' are linked to each other by a sequence of 0, 1, 2, 3, 4, 5, 6, 7, 8, 9, 10, 11, 12, 13, 141, 15, 16, 17, 18, 19, 20, 21, 22, 23, 24, or 25 nucleotides.

In some embodiments, the oligonucleotide comprises a hairpin structure comprising a hairpin loop of at least three nucleotides and wherein N4, N5, and N6 are in the loop region of the hairpin.

In some embodiments, the hairpin structure comprises a fully-double stranded stem of at least four nucleotide base-pairs.

In some embodiments, the sequence 5'-GGAG-3' which is linked to the 3'end of the stem of hairpin structure and there are be 0, 1, or 2 nucleotides between the 3' end of the stem and 5' end of the sequence 5'-GGAG-3'.

As used herein, the term "oligonucleotide" refers to a polymer or oligomer of nucleotide or nucleoside monomers consisting of naturally occurring bases, sugars and inter-sugar linkages. The term "oligonucleotide" also includes polymers or oligomers comprising non-naturally occurring monomers, or portions thereof, which function similarly.

The loop region of the hairpin structure can be at least three, e.g. four, five, six, seven, eight, nine, ten, eleven, or more nucleotides in length. In some embodiments, the loop is from three to nine nucleotides in length. In one embodiment, the loop is at least nine nucleotides in length. In some embodiments, the loop comprises at least one oligonucleotide modification described herein. Without limitations, an oligonucleotide modification can be present at an internal position of the loop or at one of the terminus positions of the loop.

Generally, the stem of the hairpin structure is fully double stranded and is at least four, e.g., four, five, six, seven, eight, nine, ten, eleven, twelve, thirteen, fourteen, fifteen or more nucleotide basepairs in length. By "fully double-stranded" is meant that the double stranded region does not comprise one or more single-stranded nucleotides in one or both stands of the stem over its length. In other words, the stem does not comprise any interior loops, branch junctions or bulges. In some embodiments, the stem comprises at least one oligonucleotide modification described herein. Without limitations, an oligonucleotide modification can be present at an internal position of the stem or at one of the terminus positions of the stem.

A part of the sequence of formula 5'-N1N2N3N4N5N6N7N8N9-3' is present in the loop of the hairpin structure. Preferably N4, N5, and N6 are present in the loop. In some embodiments, N5 is at the third, fourth, fifth, sixth, or seventh of the loop. In one embodiment, N5 is at the middle position of the loop, i.e., there are an equal number of single-stranded nucleotides on both side of N5 in the loop. It is to be understood that the first position in the loop is the first nucleotide in the loop that is not base-paired, counting from the end of stem. In some embodiments, the sequence of formula 5'-N1N2N3N4N5N6N7N8N9-3' comprises at least one oligonucleotide modification described herein. Without limitations, an oligonucleotide modification can be present at an internal position of the stem or at one of the terminus positions of the sequence of formula 5'-N1N2N3N4N5N6N7N8N9-3'.

In some embodiments, N1 and N3 are independently selected purines and N7, N8, and N9 are independently selected pyrimidines.

In some embodiments, N2 and N4 are guanosine and N5 is adenosine.

In some embodiments, N1 and N5 are adenosine; N3 is adenosine or uridine; N2 and N4 are guanosine; and N6, N7, N8, and N9 are uridine.

In some embodiments, N1, N3, N8, and N9 are independently selected pyrimidines and N7 is a purine.

In some embodiments, N1, N3, and N6 are uridine; N2, N5, and N7 are adenosine; N4 is guanosine; and N8 and N9 are cytosine.

Oligonucleotides of the present invention can be of various lengths. In some embodiments, the oligonucleotide is at least 18 nucleotides in length. In some embodiments, oligonucleotides can range from 19 to 100 nucleotides in length. In some embodiments, the oligonucleotide is from 19 to 50; 19 to 35; 19 to 30, or 19 to 25 nucleotides in length. In some embodiments, the oligonucleotide is 18, 19, 20, 21, 22, 23, 24, 25, 26, 27, 28, 29, 30, 31, 32, 33, 34, 35, 36, 37, 38, 39, or 40 nucleotides in length.

In some embodiments, the oligonucleotide comprises, consists of or consists essentially of the sequence 5'-GGGCAGAGAUUUUGCCCGGAG-3' (SEQ ID NO: 16), 5'-GGGGUAGUGAUUUUACCCUGGAG-3' (SEQ ID NO: 17) or 5'-GGGGUCUAUGAUACCACCCCGGAG-3' (SEQ ID NO: 18).

In some embodiments, the oligonucleotide is not one of UUAGGGCAGGGAUUUUGCCCACAAGGAGGU (SEQ ID NO: 19), UAGAAUUACAUCAAGGGAGAU (SEQ ID NO: 20), GUGGGGUAGUGAUUUUACCCUGUUCAGGAGAU (SEQ ID NO: 21), UAGAGUUACACCCUGGGAGUU (SEQ ID NO: 22), UGGGGCUCUGCCCUGCUAUGGGAU (SEQ ID NO: 23), GGUCGGGUUGUGACAUUGCCCGCUGUGGAGAU (SEQ ID NO: 24), UUAGGGUCAUACCCCAUCUUGGAGAU (SEQ ID NO: 25), UGAGGGUCUAUGAUACCACCCGGUACAGGAGAU (SEQ ID NO: 26), UUAGGGUCACACCCACCACUGGGAGAU (SEQ ID NO: 27), GAGGAGGACACCCAAGGAGAUC (SEQ ID NO: 28), UCAGGGCAGUGAUGUUGCCCCUCGGAAGAU (SEQ ID NO: 29), GUGGGGUAGGGAUAUUAGGCCCCAAUUAGAAGAU (SEQ ID NO: 30), UAAGGGUCUGUGACACCACCCUCUGUUGGAGAU (SEQ ID NO: 31), or GGUAGGGUCURUGAYAYYRCCCGSURYRGGAGAU (SEQ ID NO: 32).

Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases. Typical oligonucleotide modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the 2' hydroxyl on the ribose sugar; (iii) wholesale replacement of the phosphate moiety with “dephospho” linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

An oligonucleotide described herein can comprise any oligonucleotide modification described herein. In some embodiments, the oligonucleotide comprises at least one modification. In some embodiments, the modification is selected from the group consisting of a sugar modification, a non-phosphodiester intersugar (or internucleoside) linkage, nucleobase modification, and ligand conjugation. In some embodiments, the oligonucleotide comprises at least two different modifications selected from the group consisting of a sugar modification, a non-phosphodiester intersugar linkage, nucleobase modification, and ligand conjugation.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

The phosphate group in the intersugar linkage can be modified by replacing one of the oxygens with a different substituent. One result of this modification to oligonucleotide phosphate intersugar linkages can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the intersugar linkage can be replaced by any of the following: S, Se, BR3 (R is hydrogen, alkyl, aryl), C (i.e. an alkyl group, an aryl group, etc. . . . ), H, NR2 (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the “R” configuration (herein Rp) or the “S” configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as “non-phosphodiester intersugar linkage” or “non-phosphodiester linker.”

The phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-CH2-C(=O)—N(H)-5') and amide-4 (3'-CH2-N(H)—C(=O)-5')), hydroxylamino, siloxane (dialkylsiloxxane), carboxamide, carbonate, carboxymethyl, carbamate, carboxylate ester, thioether, ethylene oxide linker, sulfide,sulfonate, sulfonamide, sulfonate ester, thioformacetal (3'-S—CH2-O-5'), formacetal (3'-β-CH2-O-5), oxime, methyleneimino, methykenecarbonylamino, methylenemethylimino (MMI, 3'-CH2-N(CH3)-O-5'), methylenehydrazo, methylenedimethylhydrazo, methyleneoxymethylimino, ethers (C3'-O—C5'), thioethers (C3'-S—C5'), thioacetamido (C3-N(H)—C(=O)—CH2-S—C5'C3'-O—P(O)—O—SS—C5', C3'-CH2-NH—NH—C5, 3'-NHP(O)(OCH3)-O-5' and 3'-NHP(O)(OCH3)-O-5' and nonionic linkages containing mixed N, O, S and CH2 component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methylphosphonate), selenophosphates, phosphoramidates (e.g., N-alkylphosphoramidate), and boranophosphonates.

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiments, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R═H, alkyl, cycloalkyl, aryl, aralkyl, heteroaryl or sugar); polyethyleneglycols (PEG), O(CH2CH2O)nCH2CH2OR, n=1-50; "locked" nucleic acids (LNA) in which the oxygen at the 2' position is connected by (CH2)n, wherein n=1-4, to the 4' carbon of the same ribose sugar, preferably n is 1 (LNA) or 2 (ENA); O-AMINE or O—(CH2)nAMINE (n=1-10, AMINE=NH2; alkylamino, dialkylamino, heterocyclyl, arylamino, diaryl amino, heteroaryl amino, diheteroaryl amino, ethylene diamine or polyamino); and O—CH2CH2 (NCH2CH2NMe2)2.

"Deoxy" modifications include hydrogen (i.e. deoxyribose sugars, which are of particular relevance to the single-strand overhangs); halo (e.g., fluoro); amino (e.g. NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thio-alkyl; thioalkoxy; thioalkyl; alkyl; cycloalkyl; aryl; alkenyl and alkynyl, which can be optionally substituted with e.g., an amino functionality.

A modification at the 2' position can be present in the arabinose configuration The term "arabinose configuration" refers to the placement of a substituent on the C2' of ribose in the same configuration as the 2'-OH is in the arabinose.

Oligonucleotides can also include abasic sugars, which lack a nucleobase at C-1' or have other chemical groups in place of a nucleobase at C1'. See for example U.S. Pat. No. 5,998,203, contents of which are herein incorporated in their entirety. These abasic sugars can also be further containing modifications at one or more of the constituent sugar atoms. Oligonucleotides can also contain one or more sugars that are the L isomer, e.g. L-nucleosides. Modification to the sugar group can also include replacement of the 4'-O with a sulfur, optionally substituted nitrogen or CH2 group. In some embodiments, linkage between Cl' and nucleobase is in the α configuration. Sugar modifications can also include acyclic nucleotides, wherein a C—C bonds between ribose carbons (e.g., C1'-C2', C2'-C3', C3'-C4', C4'-04', C1'-O4') is absent and/or at least one of ribose carbons or oxygen (e.g., C1', C2', C3', C4' or O4') are independently or in combination absent from the nucleotide.

In some embodiments, the sugar modification is selected from the group consisting of 2'-H (DNA), 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-F arabinose, 2'-OMe arabinose, arabinose, and any combinations thereof.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

Adenine, cytosine, guanine, thymine and uracil are the most common bases (or nucleobases) found in nucleic acids. These bases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the above modifications. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligonucleotide can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-N6-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N6-(isopentyl)adenine, N6-(methyl)adenine, N6,N6-(dimethyl)adenine, 2-(alkyl)guanine, 2-(propyl)guanine, 6-(alkyl)guanine, 6-(methyl)guanine, 7-(alkyl) guanine, 7-(methyl)guanine, 7-(deaza)guanine, 8-(alkyl) guanine, 8-(alkenyl)guanine, 8-(alkynyl)guanine, 8-(amino) guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N4-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio) uracil, 5-(methyl)-2,4-(dithio)uracil, 5-(methylaminomethyl)-2,4-(dithio)uracil, 5-(2-aminopropyl)uracil, 5-(alkyl) uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N3-(methyl)uracil, 5-uracil (i.e., pseudouracil), 2-(thio)pseudouracil,4-(thio)pseudouracil,2,4-(dithio) psuedouracil, 5-(alkyl)pseudouracil, 5-(methyl)pseudouracil, 5-(alkyl)-2-(thio)pseudouracil, 5-(methyl)-2-(thio) pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2, 4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio) pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phen thiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, N2-substituted purines, N6-substituted purines, O6-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any modified or nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4, 5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, Nucleic Acids Research, 29, 2437-2447).

Further nucleobases include those disclosed in U.S. Pat. No. 3,687,808; those disclosed in PCT App. Pub. No. WO/2009/120878; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

The 3' and 5' ends of an oligonucleotide can be modified. Such modifications can be at the 3' end, 5' end or both ends of the molecule. For example, the 3' and/or 5' ends of an oligonucleotide can be conjugated to other functional molecular entities such as labeling moieties, e.g., fluorophores or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

Terminal modifications useful for modulating activity include modification of the 5' end with phosphate or phosphate analogs. For example, in some embodiments, the oligonucleotide is phosphorylated or includes a phosphoryl analog at the 5' terminus. Exemplary 5'-modifications include, but are not limited to, 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)2(O)P—NH-5', (HO)(NH2)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH2OMe), ethoxymethyl, etc. . . . ). Other exemplary 5'-modifications include where Z is optionally substituted alkyl at least once, e.g., ((HO)2(X)P—O[—(CH2)a-O—P(X)(OH)—O]b-5', ((HO)2(X)P—O[—(CH2)a-P(X)(OH)-P]b-5', ((HO)2(X)P—[—(CH2)a-O—P(X)(OH)—O]b-5; dialkyl terminal phosphates and phosphate mimics: HO[—(CH2)a-O—P(X)(OH)—O]b-5', H2[—(CH2)a-O—P(X)(OH)—O]b-5', H[—(CH2)a-O—P(X)(OH)—O]b-5', Me2NB[—(CH2)a-O—P(X)(OH)—O]b-5', HO[—(CH2)a-P(X)(OH)—O]b-5', H2N[—(CH2)a-P(X)(OH)—O]b-5', H[—(CH2)a-P(X)(OH)—O]b-5', Me2N[—(CH2)a-P(X)(OH)—O]b-5', wherein a and b are each independently 1-10. Other embodiments, include replacement of oxygen and/or sulfur with BH3, BH3- and/or Se.

Additional terminal modifications are described, for example, in Manoharan, M. et al. Antisense and Nucleic Acid Drug Development 12, 103-128 (2002) and references therein.

In some embodiments, the oligonucleotide comprises a cap structure at 3' (3'-cap), 5' (5'-cap) or both ends. In some embodiments, oligonucleotide comprises a 3'-cap. In another embodiment, oligonucleotide comprises a 5'-cap. In yet another embodiment, oligonucleotide comprises both a 3' cap and a 5' cap. It is to be understood that when an oligonucleotide comprises both a 3' cap and a 5' cap, such caps can be same or they can be different.

As used herein, “cap structure” refers to chemical modifications, which have been incorporated at either terminus of oligonucleotide. See for example U.S. Pat. No. 5,998,203 and International Patent Publication WO03/70918, contents of which are herein incorporated in their entireties. Exemplary 5'-caps include, but are not limited to, ligands, 5'-5'-inverted nucleotide, 5'-5'-inverted abasic nucleotide residue, 2'-5' linkage, 5'-amino, 5'-amino-alkyl phosphate, 5'-hexylphosphate, 5'-aminohexyl phosphate, bridging and/or non-bridging 5'-phosphoramidate, bridging and/or non-bridging 5'-phosphorothioate and/or 5'-phosphorodithioate, bridging or non-bridging 5'-methylphosphonate, non-phosphodiester intersugar linkage between the end two nucleotides, 4',5'-methylene nucleotide, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, 5'-mercapto nucleotide and 5'-1,4-butanediol phosphate.

Exemplary 3'-caps include, but are not limited to, ligands, 3'-3'-inverted nucleotide, 3'-3'-inverted abasic nucleotide residue, 3'-2'-inverted nucleotide moiety, 3'-2'-inverted abasic moiety, 2'-5'-linkage, 3'-amino, 3'-amino-alkyl phosphate, 3'-hexylphosphate, 3'-aminohexyl phosphate, bridging and/or non-bridging 3'-phosphoramidate, bridging and/or non-bridging 3'-phosphorothioate and/or 3'-phosphorodithioate, bridging or non-bridging 3'-methylphosphonate, non-phosphodiester intersugar linkage between the end two nucleotides, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, and 3'-1,4-butanediol phosphate. For more details see Beaucage and Iyer, 1993, Tetrahedron 49, 1925, incorporated by reference herein.

Other 3' and/or 5' caps amenable to the invention are described in Int. Pat. Pub. No. WO 2011/005861, content of which is incorporated herein by reference.

In some embodiments, the oligonucleotide comprises at least one (e.g., 1, 2, 3, 4, 5, 6, 7, 8, 9, or 10 or more), of 5'-5', 3'-3', 3'-2', 2'-5', 2'-3' or 2'-2' intersugar linkage. In some embodiments, the last nucleotide on the terminal end is linked via a 5'-5', 3'-3', 3'-2', 2'-5', 2'-3' or 2'-2' intersugar linkage to the rest of the oligonucleotide. In some embodiments, the last nucleotide on both the terminal ends is linked via a 5'-5', 3'-3', 3'-2', 2'-3' or 2'-2' intersugar linkage to the rest of the oligonucleotide. In some embodiments, at least one 5'-5', 3'-3', 3'-2', 2'-5', 2'-3' or 2'-2' intersugar linkage is a non-phosphodiester linkage.

A wide variety of entities, e.g., ligands, can be coupled to the oligonucleotides described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., alpha-helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, cpf, bombinin-like peptide (blp), cathelicidins, ceratotoxins, s. clava peptides, hagfish intestinal antimicrobial peptides (hfiaps), magainines, brevinins-2, dermaseptins, melittins, pleurocidin, h2a peptides, xenopus peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), Golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and brached polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to, AALEALAEALEALAEALEALAEAAAAGGC (GALA) (SEQ ID NO: 33); AALAEALAEALAEALAEALAEALAAAAGGC (EALA) (SEQ ID NO: 34); ALEALAEALEALAEA (SEQ ID NO: 35); GLFEAIEGFIENGWEGMIWDYG (INF-7) (SEQ ID NO: 36); GLFGAIAGFIENGWEGMIDGWYG (Inf HA-2) (SEQ ID NO: 37); GLFEAIEGFIENGWEGMIDGWYGCGLFEAIEGFIENGWEGMID GWYGC (diINF-7) (SEQ ID NO: 38); GLFEAIEGFIENGWEGMIDGGCGLFEAIEGFIENGWEGMIDGGC (diINF-3) (SEQ ID NO: 39); GLFGALAEALAEALAEHLAEALAEALEALAAGGSC (GLF) (SEQ ID NO: 40); GLFEAIEGFIENGWEGLAEALAEALEALAAGGSC (GALA-INF3) (SEQ ID NO: 41); GLFEAIEGFIENGWEGnI DG K GLF EAI EGFI ENGW EGnI DG (INF-5, n is norleucine) (SEQ ID NO: 42); LFEALLELLESLWELLLEA (JTS-1) (SEQ ID NO: 43); GLFKALLKLLKSLWKLLLKA (ppTG1) (SEQ ID NO: 44); GLFRALLRLLRSLWRLLLRA (ppTG20) (SEQ ID NO: 45); WEAKLAKALAKALAKHLAKALAKALKACEA (KALA) (SEQ ID NO: 46); GLFFEAIAEFIEGGWEGLIEGC (HA) (SEQ ID NO: 47); GIGAVLKVLTTGLPALISWIKRKRQQ (Melittin) (SEQ ID NO: 48); HSWYG; and CHK6HC.

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), and palmitoyloleoylphosphatidylcholine (POPC).

Synthetic polymers with endosomolytic activity amenable to the present invention are described in U.S. Pat. App. Pub. No. 2009/0048410; No. 2009/0023890; No. 2008/0287630; No. 2008/0287628; No. 2008/0281044; No. 2008/0281041; No. 2008/0269450; No. 2007/0105804; No. 20070036865; and No. 2004/0198687, content of all of which is incorporated herein by reference.

Exemplary cell permeation peptides include, but are not limited to, RQIKIWFQNRRMKWKK (penetratin) (SEQ ID NO: 49); GRKKRRQRRRPPQC (Tat fragment 48-60) (SEQ ID NO: 50); GALFLGWLGAAGSTMGAWSQPKKKRKV (signal sequence based peptide) (SEQ ID NO: 51); LLIILRRRIRKQAHAHSK (PVEC) (SEQ ID NO: 52); GWTLNSAGYLLKINLKALAALAKKIL (transportan) (SEQ ID NO: 53); KLALKLALKALKAALKLA (amphiphilic model peptide) (SEQ ID NO: 54); RRRRRRRRR (Arg9) (SEQ ID NO: 55); KFFKFFKFFK (Bacterial cell wall permeating peptide) (SEQ ID NO: 56); LLGDFFRKSKEKIGKEFKRIVQRIKDFLRNLVPRTES (LL-37) (SEQ ID NO: 57); SWLSKTAKKLENSAKKRISEGIAIAIQGGPR (cecropin P1) (SEQ ID NO: 58); ACYCRIPACIAGERRYGTCIYQGRLWAFCC (α-defensin) (SEQ ID NO: 59) DHYNCVSSGGQCLYSACPIFTKIQGTCYRGKAKCCK (β-defensin) (SEQ ID NO: 60); RRRPRPPYLPRPRPPPFFPPRLPPRIPPGFPPRFPPRFPGKR-NH2 (PR-39) (SEQ ID NO: 61); ILPWKWPWWPWRR-NH2 (indolicidin) (SEQ ID NO: 62); AAVALLPAVLLALLAP (RFGF) (SEQ ID NO: 63); AALLPVLLAAP (RFGF analogue) (SEQ ID NO: 64); and RKCRIVVIRVCR (bactenecin) (SEQ ID NO: 65).

Exemplary cationic groups include, but are not limited to, protonated amino groups, derived from e.g., O-AMINE (AMINE=NH2; alkylamino, dialkylamino, heterocyclyl, arylamino, diaryl amino, heteroaryl amino, or diheteroaryl amino, ethylene diamine, polyamino); aminoalkoxy, e.g., O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino); amino (e.g. NH2; alkylamino, dialkylamino, heterocyclyl, arylamino, diaryl amino, heteroaryl amino, diheteroaryl amino, or amino acid); and NH(CH2CH2NH)nCH2CH2-AMINE (AMINE=NH2; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,410,104; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2,4,6-triiodophenol and flufenamic acid). Oligonucleotides that comprise a number of phosphorothioate intersugar linkages are also known to bind to serum protein, thus short oligonucleotides, e.g. oligonucleotides of comprising from about 5 to 30 nucleiotides (e.g., 5 to 25 nulceotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

In some embodiments, the ligand is a fluorescent reporter, e.g. a fluorophore. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (Invitrogen Corp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramefhyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p(2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H,15H-Xantheno[2,3,4-ij:5,6,7-i'j']diquinolizin-18-ium, 9-[2 (or 4)-[[[6[2,5-dioxo-1-pyrrolidinyl)oxy]-6-oxohexyl] amino]sulfonyl]-4(or 2)-sulfophenyl]-2,3,6,7,12,13,16,17octahydro-inner salt (TR or Texas Red); BODIPY™ dyes; benzoxadiazoles; stilbenes; pyrenes; and the like. Many suitable forms of these fluorescent compounds are available and can be used.

Ligands can be coupled to the oligonucleotides at various places, for example, 3'-end, 5'-end, and/or at an internal position. When two or more ligands are present, the ligand can be on opposite ends of an oligonucleotide. In preferred embodiments, the ligand is attached to the oligonucleotides via an intervening tether/linker. The ligand or tethered ligand can be present on a monomer when said monomer is incorporated into the growing strand. In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH2 can be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118, 802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904, 582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574, 142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents which are herein incorporated in their entireties by reference.

In some embodiments, the ligands, e.g. endosomolytic ligands, targeting ligands or other ligands, are linked to a monomer which is then incorporated into the growing oligonucleotide strand during chemical synthesis. Such monomers are also referred to as carrier monomers herein. The carrier monomer is a cyclic group or acyclic group; preferably, the cyclic group is selected from the group consisting of pyrrolidinyl, pyrazolinyl, pyrazolidinyl, imidazolinyl, imidazolidinyl, piperidinyl, piperazinyl, [1,3]-dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone. In some embodiments, the cyclic carrier monomer is based on pyrrolidinyl such as 4-hydroxyproline or a derivative thereof.

Exemplary ligands and ligand conjugated monomers amenable to the invention are described in U.S. Pat. App. Pub. No. 2005/0107325; No. 2005/0164235; No. 2005/0256069; No. 2006/0008822; No. 2005/0288244; No. 2007/0054279; Ser. No. 11/944,227; No. 2009/0239814; and No. 2009/0247614, content of all of which is incorporated herein by reference. Ligands and ligand conjugated monomers amenable to the invention are also described in PCT App. Pub. No. WO/2004/065601; No WO/2004/090108; No. WO2004/091515; No. WO/2006/078278; No. WO/2006/073458; No. WO/2006/112872; No. WO/2008/131419; No. WO/2009/018332; No. WO/2009/073809; and No. WO/2009/126933, content of which is incorporated herein by reference.

In some embodiments, the covalent linkages between the oligonucleotide and other components, e.g. a ligand or a ligand carrying monomer can be mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the oligonucleotide after transport to the desired target. The intended nature of the conjugation or coupling interaction, or the desired biological effect, will determine the choice of linker group.

As used herein, the term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where IV is hydrogen, acyl, aliphatic or substituted aliphatic.

In some embodiments, the linker comprises at least one cleavable linking group.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions)

Exemplary cleavable linking groups include, but are not limited to, redox cleavable linking groups (e.g., —S—S— and —$C(R)_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C═NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —$NHCHR^AC(O)NHCHR^BC(O)$—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH of about 6.5 or lower (e.g., about 6.0, 5.5, 5.0, or lower), or by agents such as enzymes that can act as a general acid.

In some embodiments, pairings which increase the propensity to form a duplex are used at one or more of the positions in the double-stranded. The terminus base pair of the stem and the subsequent two base pairing positions in the duplex are preferred for placement of modifications to increase the propensity to form a duplex. It is preferred that at least one, and more preferably two or three of the pairs of the recited regions be chosen independently from the group of: G:C, a pair having an analog that increases stability over Watson-Crick matches (A:T, A:U, G:C), 2-amino-A:U, 2-thio-U or 5-Me-thio-U:A, G-clamp (an analog of C having 4 hydrogen bonds):G, guanadinium-G-clamp:G, pseudo uridine:A, a base pair in which one or both subunits have a sugar modification, e.g., a 2' modification, e.g., 2'F, ENA, or LNA, which enhance binding. In some embodiments, at least one, at least, at least 2, or at least 3, of the base pairs promote duplex stability.

In some embodiments, at least one end of the stem double-stranded region is terminated by a G:C, G:U, G-clamp:G or guanadinium-G-clamp:G base pair, i.e., the terminus base pair is a G:C, G:U, G-clamp:G or guanadinium-G-clamp:G base pair. In some embodiments, the G:C, G:U, G-clamp:G or guanadinium-G-clamp:G base pair encloses the loop of the hairpin structure of the oligonucleotide, i.e., the loop is terminated by a G:C, G:U, G-clamp:G or guanadinium-G-clamp:G base pair. In some embodiments, the end of the stem away from the loop is terminated by a G:C, G:U, G-clamp:G or guanadinium-G-clamp:G base pair. In some embodiments, both ends of the stem are terminated independently by a G:C, G:U, G-clamp:G or guanadinium-G-clamp:G base pair.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High- Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," PNAS, US, 96:3513-8, 1999.

The oligonucleotides described herein can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidite oligonucleotides is described in U.S. Pat. No. 5,256,775 or 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed intersugar linkage compounds having, as for instance, alternating MMI and PO or PS linkages can be prepared as is described in U.S. Pat. Nos. 5,378,825, 5,386,023, 5,489,677 and in International Application Nos. PCT/US92/04294 and PCT/US92/04305 (published as WO 92/20822 WO and 92/20823, respectively). Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can occur at a 3' or 5' terminal position, can occur in the internal region, can occur in 3', 5' or both terminal regions, e.g. at a position on a terminal nucleotide or in the last 2, 3, 4, 5, 6, 7, 8, 9, or 10 nucleotides from an end of the oligonucleotide. In some embodiments, the terminal nucleotide (e.g., 3'-terminal or preferably 5'-terminal) does not comprise a modification.

Provided herein also are methods for regulating miRNA biogenesis. In one aspect, the invention provides a method for promoting miRNA processing of pre-miRNA to a mature miRNA in a cell, the method comprising contacting a cell with an oligonucleotide described herein.

The term "contacting" or "contact" as used herein in connection with contacting a cell includes subjecting the cell to an appropriate culture media which comprises the indicated Ephexin5 inhibitor. Where the cell is in vivo, "contacting" or "contact" includes administering the oligonucleotide in a pharmaceutical composition to a subject via an appropriate administration route such that oligonucleotide contacts the cell in vivo.

For in vivo methods, a therapeutically effective amount of an oligonucleotide can be administered to a subject. Methods of administering compounds to a subject are known in the art and easily available to one of skill in the art.

Provided herein also are methods for the treatment and/or prevention of cancer by administering to a subject an oligonucleotide described herein.

Subjects amenable to treatment using the methods as disclosed herein include subjects at risk of a cancer, as well as subjects at risk of developing cancer. In some embodiments, subjects amenable to treatment using the methods as disclosed herein include subjects identified with or having increased risk of cancer, for example subjects identified to carry a genetic mutation or polymorphism associated with an increased risk of developing cancer. Such mutations and genetic susceptibility genes and loci are commonly known by persons skilled in the art, for example some of the more commonly known genes where a mutation is associated with increase in cancer include, but are not limited to; BRAC1, BRAC2, EGFR, EIF4A2, ERBB2, RBI, CDKN2A, P53, INK4a, APC, MLH1, MSH2, MSH6, WTI, NF1, NF2, and VHL (see world-wide web at web site: cancer.org/docroot/ETO/content/ETO 1 4x_oncogenes_and_tumor_suppressor_genes-dot-asp).

In some embodiments, subjects can be screened for their likelihood of having or developing cancer based on a number of biochemical and genetic markers or other biomarkers. Biomarkers are defined as cellular, biochemical, molecular or genetic alterations by which a normal, abnormal or simply biologic process can be recognized or monitored. Biomarkers are measurable in biological media, such as human tissues, cells or fluids. Biomarkers could be used to identify pathological processes before individuals become symptomatic or to identify individuals who are susceptible to cancer.

Several classes of biomarkers in cancer cells and bodily fluids have been studied, mostly in laboratories examining specific observations but also in limited clinical settings. Several biomarkers have shown only limited utility: e.g., CD44, telomerase, transforming growth factor-α (TGFα), transforming growth factor-β (TGF-β), epidermal growth factor receptor erbB-2 (erbB-2), epidermal growth factor receptor erbB-3 (erbB-3), mucin 1 (MUC1), mucin 2 (MUC2) and cytokeratin 20 (CK20). Other biomarkers are used in clinical practice and include, for example Prostate specific antigen (PSA) and cancer antibody or tumor marker 125 (CA125). Several protein markers can be used as cancer biomarkers, for example but not limited to, Fecal occult blood test (FOBT), which is a protein biomarker shown to decrease cause-specific mortality in cancer screens.

In one embodiment, subjects amenable to treatment using the methods as disclosed herein include subjects with a high level of Lin28 in a biological sample from the subject as compared to a reference level of Lin-28, and thus have reduced processing of tumor suppressor miRNAs, such as let-7 miRNA. In some embodiments, the subject is assessed if they are at risk of having cancer by identifying the level of Lin28 in a biological sample from the subject and comparing the level of Lin28 with a reference level of Lin-28. For example, if the level of Lin28 in a biological sample from the subject is above a reference level, the subject is at risk of having a metastasis or a malignant cancer. In some embodiments, the biological sample obtained from the subject is from a biopsy tissue sample, and in some embodiments, the sample is from a tumor or cancer tissue sample. The level of Lin28 can be determined by any method known by one of ordinary skill in the art, for example by northern blot analysis or RT-PCR for mRNA expression levels, or ELISA or western blot analysis for protein expression levels.

In some embodiments, a reference level of Lin28 is the level of Lin28 that does not result in malignancy or a malignant cancer. In some embodiments, the reference level of Lin28 the based on the level of Lin28 expression or protein activity in a normal tissue sample, where in the tissue sample is a biological tissue sample from a tissue matched, species matched and age matched biological sample. In some embodiments, the reference level of Lin28 is based on a biological sample is from a non-malignant matched tissue sample. In some embodiments, the reference level of Lin28 is based on a biological sample from normal tissue, for example non-cancer tissue, or a non-stem cell cancer tissue sample.

In alternative embodiments, a subject amenable to treatment using the methods as disclosed herein include subjects with a low level of Let-7 miRNA family members in a biological sample from the subject as compared to a reference level of Let-7 miRNA, and thus have reduced suppression of oncogenes expression. In some embodiments, the subject is assessed if they are at risk of having cancer by identifying the level of let-7 miRNA in a biological sample from the subject and comparing the level of let-7 miRNA with a reference level of let-7 miRNA. For example, if the level of let-7 miRNA in a biological sample from the subject is below a reference level, the subject is at risk of having a metastasis or a malignant cancer. In some embodiments, the biological sample obtained from the subject is from a biopsy tissue sample, and in some embodiments, the sample is from a tumor or cancer tissue sample. The level of let-7 miRNA can be determined by methods known by the skilled artisan, for example by northern blot analysis or RT-PCR. In some embodiments, the reference level of let-7 miRNA is the level of let-7 miRNA that does not result in malignancy or a malignant cancer. In some embodiments, the reference level of let-7 miRNA is the based on the level of let-7 miRNA expression in a normal tissue sample, where in the tissue sample is a biological tissue sample from a tissue matched, species matched and age matched biological sample. In some embodiments, the reference level of let-7 miRNA is based on a biological sample is from a non-malignant matched tissue sample. In some embodiments, the reference level let-7 miRNA is based on a biological sample from a non-stem cell cancer tissue sample.

In some embodiments, the biological sample obtained from the subject is from a biopsy tissue sample. In some embodiments, the biological sample is from a tumor or cancer tissue sample.

A subject administered an oligonucleotide inhibiting Lin28 activity as disclosed herein can be evaluated for symptoms relative to a subject not administered the oligonucleotide. A measurable change in the severity a symptom (i.e., a decrease in at least one symptom, i.e. 10% or greater decrease), or a delay in the onset of a symptom, in animals treated with an oligonucleotide described herein versus untreated animals is indicative of therapeutic efficacy.

In some embodiments, the method as disclosed herein are useful for the treatment of any disease or disorder characterized by lack or reduced expression of tumor suppressor miRNAs, for example but not limited to let-7 family miRNAs.

In alternative embodiments, the methods as disclosed herein are useful for the treatment of any disease or disorder characterized by increased of Lin28 as compared to a reference level.

In alternative embodiments, the methods as disclosed herein are useful for the treatment of any disease or disorder characterized by a decrease in let-7 miRNA as compared to a reference level.

In some embodiments, the subject is assessed if they have decreased level of let-7 miRNA in a biological sample from the subject as compared to a reference level of let-7 miRNA in a reference biological sample.

In some embodiments, compositions and methods described herein can be used for the treatment of adult and/or pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In one embodiment, compositions and methods described herein can be used for treatment or prevention of breast cancer. In some embodiments, compositions and methods described herein can be used for treatment or prevention of, for example but not limited to; lung cancer, hepatic cancer or leukemia, for example but not limited to lung carcinoma, chronic myelogenous leukemia (CML) and HCC (hepatic cell carcinoma).

In addition, compositions and methods as disclosed herein can also be used for prophylactic treatment of cancer. There are hereditary conditions and/or environmental situations (e.g. exposure to carcinogens) known in the art that predispose an individual to developing cancers, or subjects identified to have increased expression of Lin28 as compared to a reference sample. Under these circumstances, it may be beneficial to treat these individuals with therapeutically effective doses of an agent which inhibit Lin28 and/or Lin-28B to reduce the risk of developing cancers.

In one embodiment, the compositions and methods disclosed herein are useful for a subject who has cancer regression.

In another embodiment, the compositions and methods disclosed herein are useful for a subject who has a therapy resistant cancer, for example a chemotherapy resistant cancer.

In some embodiments, the compositions and methods disclosed herein are useful for a subject who has cancer and has been exposed to adjuvant cancer therapies.

In another embodiment, the compositions and methods disclosed herein are useful for a subject with a malignant cancer. In some embodiments, the compositions and methods disclosed herein are useful for a subject with a cancer or tumor comprising a cancer stem cell.

Most therapeutic strategies for cancer are aimed at reducing or eliminating the tumor or tumor. In some embodiments, the compositions and methods disclosed herein are also useful in the treatment of other disease or disorders associated with abnormal cellular proliferation or differentiation of stem cells. Thus, treatment can be directed to a subject who is affected but asymptomatic with cancer, for example, a disease of an organ or tissue in a subject characterized by poorly controlled or uncontrolled multiplication of normal or abnormal cells in that tissue and its effect on the body as a whole.

Cancer diseases which can be treated or prevented by the compositions and methods disclosed herein include, but are not limited to, benign neoplasms, dysplasias, hyperplasias as well as neoplasms showing metastatic growth or any other transformations like e.g. leukoplakias which often precede a breakout of cancer.

Cancer therapy can also include prophylaxis, including agents which slow or reduce the risk of cancer in a subject. In other embodiments, a cancer therapy is any treatment or any means to prevent the proliferation of cells with abnormal proliferation or cancerous cells. In some embodiments, then anti-cancer treatment is an agent which suppresses the EGF-EGFR pathway, for example but not limited to inhibitors and agents of EGFR. Inhibitors of EGFR include, but are not limited to, tyrosine kinase inhibitors such as quinazolines, such as PID 153035, 4-(3-chloroanilino) quinazoline, orCP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines (Traxleretal., (1996) J. Med Chem 39:2285-2292), curcumin (diferuloyl methane) (Laxmin arayana, et al., (1995), Carcinogen 16:1741-1745), 4,5-bis (4-fluoroanilino)phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO05/018677 (Wyeth); W099/09016 (American Cyanamid); W098/43960 (American Cyanamid); WO 98/14451; WO 98/02434; W097/38983 (Warener Labert); W099/06378 (Warner Lambert); W099/06396 (Warner Lambert); W096/30347 (Pfizer, Inc.); W096/33978 (Zeneca); W096/33977 (Zeneca); and W096/33980 (Zeneca), WO 95/19970; U.S. Pat. App. Nos. 2005/0101618 assigned to Pfizer, 2005/0101617, 20050090500 assigned to OSI Pharmaceuticals, Inc.; all herein incorporated by reference. Further useful EGFR inhibitors are described in U.S. Pat. App. No. 20040127470, particularly in tables 10, 11, and 12, and are herein incorporated by reference.

In another embodiment, the present invention encompasses combination therapy in which subjects identified as having, or increased risk of developing cancer are administered an anti-cancer combination therapy where combinations of anti-cancer agents are used are used in combination with cytostatic agents, anti-VEGF and/or p53 reactivation agent. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics include inhibitors of matrix metalloproteinases such as marimastat, growth factor antagonists, signal transduction inhibitors and protein kinase C inhibitors.

In another embodiment, the anti-cancer therapy includes a chemotherapeutic regimen further comprises radiation therapy. In an alternate embodiment, the therapy comprises administration of an anti-EGFR antibody or biological equivalent thereof.

In some embodiments, the anti-cancer treatment comprises the administration of a chemotherapeutic drug selected from the group consisting of fluoropyrimidine (e.g., 5-FU), oxaliplatin, CPT-11, (e.g., irinotecan) a platinum drug or an anti EGFR antibody, such as the cetuximab antibody or a combination of such therapies, alone or in combination with surgical resection of the tumor. In yet a further aspect, the treatment compresses radiation therapy and/or surgical resection of the tumor masses. In one embodiment, the present invention encompasses administering to a subject identified as having, or increased risk of developing RCC an anti-cancer combination therapy where combinations of anti-cancer agents are used, such as for example Taxol, cyclophosphamide, cisplatin, gancyclovir and the like. Anti-cancer therapies are well known in the art and are encompassed for use in the methods of the present invention. Chemotherapy includes, but is not limited to an alkylating agent, mitotic inhibitor, antibiotic, or antimetabolite, anti-angiogenic agents etc. The chemotherapy can comprise administration of CPT-11, temozolomide, or a platin compound. Radiotherapy can include, for example, x-ray irradiation, w-irradiation, y-irradiation, or microwaves.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex orTrexall), irinotecan (CPT-11); erlotinib; oxalipatin; anthracyclins-idarubicin and daunorubicin; doxorubicin; alkylating agents such as melphalan and chlorambucil; cisplatinum, methotrexate, and alkaloids such as vindesine and vinblastine.

Some examples of anti-VEGF agents include bevacizumab (AvastinTM), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by *Aspergillus fumigates.*

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. Exemplary VEGF inhibitors, i.e., anti-VEGF agents, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (AEterna Zentaris Inc; Quebec City, Calif.) and combinations thereof.

For administering to a subject, the Lin28 fragment or an oligonucleotide described herein can be formulated in a pharmaceutically acceptable composition. Thus, in another aspect, the present invention provides pharmaceutically acceptable compositions which comprise a therapeutically-effective amount of a Lin28 fragment or an oligonucleotide described herein, formulated together with one or more pharmaceutically acceptable carriers (additives) and/or diluents. The pharmaceutical composition can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the oligonucleotide can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, contents of all of which are incorporated herein by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders.

A formulated oligonucleotide composition can assume a variety of states. In some examples, the composition is at least partially crystalline, uniformly crystalline, and/or anhydrous (e.g., less than 80, 50, 30, 20, or 10% water). In another example, the oligonucleotide is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a micro particle as can be appropriate for a crystalline composition). Generally, the oligonucleotide composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An oligonucleotide preparation can be formulated in combination with another agent, e.g., another therapeutic agent or an agent that stabilizes the oligonucleotide, e.g., a protein that complex with oligonucleotide to form an oligonucleotide-protein complex. Still other agents include chelators, e.g., EDTA (e.g., to remove divalent cations such as $Mg^{2+}$), salts, DNAse inhibitors, RNAse inhibitors (e.g., a broad specificity RNAse inhibitor such as RNAsin) and so forth.

The oligonucleotides can be formulated in liposomes. As used herein, a liposome is a structure having lipid-containing membranes enclosing an aqueous interior. Liposomes can have one or more lipid membranes. In some embodiments, liposomes have an average diameter of less than about 100 nm. More preferred embodiments provide liposomes having an average diameter from about 30-70 nm and most preferably about 40-60 nm. Oligolamellar large vesicles and multilamellar vesicles have multiple, usually concentric, membrane layers and are typically larger than 100 nm. Liposomes with several nonconcentric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., U.S. Pat. Nos.

4,235,871; 4,737,323; 4,897,355 and 5,171,678; published International Applications WO 96/14057 and WO 96/37194; Felgner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

The oligonucleotides of the invention can be prepared and formulated as micelles. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In some embodiments, the formulations comprises micelles formed from an oligonucleotide of the invention and at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 30 nm, or even less than about 20 nm.

Micelle formulations can be prepared by mixing an aqueous solution of the oligonucleotide composition, an alkali metal $C_8$ to $C_{22}$ alkyl sulphate, and an amphiphilic carrier. The amphiphilic carrier can be added at the same time or after addition of the alkali metal alkyl sulphate. Micelles will form with substantially any kind of mixing of the ingredients but vigorous mixing in order to provide smaller size micelles.

The oligonucleotides of the present invention can be prepared and formulated as emulsions. As used herein, "emulsion" is a heterogeneous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The oligonucleotide can be present as a solution in either the aqueous phase, oily phase or itself as a separate phase.

In some embodiments, the compositions are formulated as microemulsions. As used herein, "microemulsion" refers to a system of water, oil and amphiphile which is a single optically isotropic and thermodynamically stable liquid solution. Microemuslions also include thermodynamically stable, isotropically clear dispersions of two immiscible liquids that are stabilized by interfacial films of surface-active molecules.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

The oligonucleotides of the present invention can be prepared and formulated as lipid particles, e.g., formulated lipid particles (FLiPs) comprising (a) an oligonucleotide of the invention, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated. The stoichiometry of oligonucleotide to the lipid component can be 1:1. Alternatively the stoichiometry can be 1:many, many:1 or many:many, where many is two or more.

The FLiP can comprise triacylglycerols, phospholipids, glycerol and one or several lipid-binding proteins aggregated, admixed or associated via a lipophilic linker molecule with an oligonucleotide. Surprisingly, it has been found that due to said one or several lipid-binding proteins in combination with the above mentioned lipids, the FLiPs show affinity to liver, gut, kidney, steroidogenic organs, heart, lung and/or muscle tissue. These FLiPs can therefore serve as carrier for oligonucleotides to these tissues. For example, lipid-conjugated oligonucleotides, e.g., cholesterol-conjugated oligonucleotides, bind to HDL and LDL lipoprotein particles which mediate cellular uptake upon binding to their respective receptors thus directing oligonucleotide delivery into liver, gut, kidney and steroidogenic organs, see Wolfrum et al. Nature Biotech. (2007), 25:1145-1157.

The FLiP can be a lipid particle comprising 15-25% triacylglycerol, about 0.5-2% phospholipids and 1-3% glycerol, and one or several lipid-binding proteins. FLiPs can be a lipid particle having about 15-25% triacylglycerol, about 1-2% phospholipids, about 2-3% glycerol, and one or several lipid-binding proteins. In some embodiments, the lipid particle comprises about 20% triacylglycerol, about 1.2% phospholipids and about 2.25% glycerol, and one or several lipid-binding proteins.

Another suitable lipid component for FLiPs is lipoproteins, for example isolated lipoproteins or more preferably reconstituted lipoproteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins). Methods of producing reconstituted lipoproteins are known in the art, for example see A. Jones, Experimental Lung Res. 6, 255-270 (1984), U.S. Pat. Nos. 4,643,988 and 5,128,318, PCT publication WO87/02062, Canadian Pat. No. 2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

One preferred lipid component for FLiP is Intralipid. Intralipid® is a brand name for the first safe fat emulsion for human use. Intralipid® 20% (a 20% intravenous fat emulsion) is made up of 20% soybean oil, 1.2% egg yolk phospholipids, 2.25% glycerin, and water for injection. It is further within the present invention that other suitable oils, such as safflower oil, can serve to produce the lipid component of the FLiP.

FLiP can range in size from about 20-50 nm or about 30-50 nm, e.g., about 35 nm or about 40 nm. In some embodiments, the FLiP has a particle size of at least about 100 nm. FLiPs can alternatively be between about 100-150 nm, e.g., about 110 nm, about 120 nm, about 130 nm, or about 140 nm, whether characterized as liposome- or emulsion-based. Multiple FLiPs can also be aggregated and delivered together; therefore the size can be larger than 100 nm.

The process for making the lipid particles comprises the steps of: (a) mixing a lipid component with one or several lipophile (e.g. cholesterol) conjugated oligonucleotides that can be chemically modified; and (b) fractionating this mixture. In some embodiments, the process comprises the additional step of selecting the fraction with particle size of 30-50 nm, preferably of about 40 nm in size.

Some exemplary lipid particle formulations amenable to the invention are described in U.S. Pat. App. Pub. No. 2010/0003317, content of which is incorporated herein by reference.

In some embodiments, the oligonucleotide is formulated in yeast cell wall particles ("YCWP"). A yeast cell wall particle comprises an extracted yeast cell wall exterior and a core, the core comprising a payload (e.g., oligonucleotides). Exterior of the particle comprises yeast glucans (e.g. beta glucans, beta-1,3-glucans, beta-1,6-glucans), yeast mannans, or combinations thereof. Yeast cell wall particles are typically spherical particles about 1-4 μm in diameter.

Preparation of yeast cell wall particles is known in the art, and is described, for example in U.S. Pat. Nos. 4,992,540; 5,082,936; 5,028,703; 5,032,401; 5,322,841; 5,401,727; 5,504,079; 5,607,677; 5,741,495; 5,830,463; 5,968,811; 6,444,448; and 6,476,003, U.S. Pat. App. Pub. Nos. 2003/0216346 and 2004/0014715, and Int. App. Pub. No. WO 2002/12348, contents of which are herein incorporated by reference in their entirety. Applications of yeast cell like particles for drug delivery are described, for example in U.S. Pat. Nos. 5,032,401; 5,607,677; 5,741,495; and 5,830,463, and U.S. Pat. Pub Nos. 2005/0281781 and 2008/0044438, contents of which are herein incorporated by reference in their entirety. U.S. Pat. App. Pub. No. 2009/0226528, contents of which are herein incorporated by reference, describes formulation of nucleic acids with yeast cell wall particles for delivery of oligonucleotide to cells.

Exemplary formulations for oligonucleotides are described in U.S. Pat. Nos. 4,897,355: 4,394,448; 4,235,871; 4,231,877; 4,224,179; 4753,788, 4,673:567, 4,247,411: 4,814,270; 5,567,434; 5,552,157; 5,565,213; 5,738,868; 5,795,587; 5,922,859: and 6,077,663, lnt. App Nos. PCT/US07/079203, filed Sep. 21, 2007; PCT/US07/080331, filed Oct. 3, 2007; U.S. patent application Ser. No. 12/123,922, filed May 28, 2008; U.S. Pat. App. Pub. No. 2006/0240093 and No. 2007/0135372, contents of which are herein incorporated by reference in their entirety. Bair (1994) Bioconjugate Chem 5:382-389, and Lewis et al. (1996) PNAS 93:3176-3181), also describe formulations for oligonucleotides that are amenable to the invention, contents of which are herein incorporated by reference in their entirety.

The phrase "therapeutically-effective amount" as used herein means that amount of an oligonucleotide described herein or a composition comprising an oligonucleotide described herein which is effective for producing some desired therapeutic effect in at least a sub-population of cells in an animal at a reasonable benefit/risk ratio applicable to any medical treatment. For example, an amount of an oligonucleotide administered to a subject that is sufficient to produce a statistically significant, measurable inhibition of a Lin28 polypeptide activity or produce a statistically significant, measurable increase in processing of a pre-miRNA.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

An oligonucleotide can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. Exemplary modes of administration include, but are not limited to, injection, infusion, instillation, inhalation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

As used herein, a "subject" means a human or animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of conditions or disorders associated with decreased spine/excitatory synapse formation and/or numbers. In addition, the methods and compositions described herein can be used to treat domesticated animals and/or pets.

The amount of a Lin28 fragment or an oligonucleotide that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that an oligonucleotide is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg,8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that oligonucleotide has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to oligonucleotide. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The oligonucleotide can be administrated to a subject in combination with one or more pharmaceutically active agents. Exemplary pharmaceutically active compound include, but are not limited to, those found in *Harrison's Principles of Internal Medicine,* $13^{th}$ Edition, Eds. T. R. Harrison et al. McGraw-Hill N.Y., NY; Physicians' Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

The oligonucleotide and the pharmaceutically active agent can be administrated to the subject in the same pharmaceutical composition or in different pharmaceutical compositions (at the same time or at different times). When administrated at different times, the oligonucleotide and the pharmaceutically active agent can be administered within 5 minutes, 10 minutes, 20 minutes, 60 minutes, 2 hours, 3 hours, 4, hours, 8 hours, 12 hours, 24 hours of administration of the other. When the oligonucleotide and the pharmaceutically active agent are administered in different pharmaceutical compositions, routes of administration can be different.

In some embodiments, the pharmaceutically active agent is an anti-cancer agent.

The invention can also be described by any one of the following numbered paragraphs:

1. An isolated RNA oligonucleotide comprising:
    a. a nucleotide sequence of formula 5'-$N^1N^2N^3N^4N^5N^6N^7N^8N^9$-3', wherein $N^2$, $N^4$, and $N^5$ are independently a purine; $N^6$ is a pyrimidine; $N^1$, $N^3$, $N^7$, $N^8$, and $N^9$ are independently any nucleotide; and
    b. a nucleotide sequence of 5'-GGAG-3', wherein the sequence 5'-GGAG-3' is linked to the 3' of the sequence of formula 5'-$N^1N^2N^3N^4N^5N^6N^7N^8N^9$-3', wherein the sequence 5'-GGAG-3' is single-stranded, wherein there are from 0 to 100 nucleotides between the 3' end of 5'-$N^1N^2N^3N^4N^5N^6N^7N^8N^9$-3' and 5' end of the sequence 5'-GGAG-3'.
2. The oligonucleotide of paragraph 1, wherein the oligonucleotide comprises a hairpin structure comprising a hairpin loop of at least 3 nucleotides and $N^4$, $N^5$, and $N^6$ are in the loop region of the hairpin.
3. The oligonucleotide of paragraph 2, wherein the hairpin structure comprises a double-stranded stem of at least four nucleotide base pairs, wherein the stem is fully double-stranded.
4. The oligonucleotide of any of paragraphs 1-3, wherein the oligonucleotide is from 19 to 100 nucleotides in length.
5. The oligonucleotide of any of paragraphs 3-4, wherein the stem comprises at least one G-clamp:G or guanadinium-G-clamp:G base pair.

6. The oligonucleotide of any of paragraphs 3-5, wherein the stem is terminated by a G:C, G:U, G-clamp:G or guanadinium-G-clamp:G base pair.
7. The oligonucleotide of any of paragraphs 1-6, wherein the oligonucleotide comprises at least one 5'-5', 3'-3', 3'-2', 2'-5', 2'-3' or 2'-2' intersugar.
8. The oligonucleotide of any of paragraphs 1-6, wherein the oligonucleotide comprises at least one modification selected from the group consisting of a sugar modification, a non-phosphodiester intersugar (or internucleoside) linkage, nucleobase modification, and ligand conjugation.
9. The oligonucleotide of any of paragraphs 1-8, wherein the oligonucleotide comprises a sugar modification selected from the group consisting of 2'-H (DNA), 2'-O-Me (2'-O-methyl), 2'-O-MOE (2'-O-methoxyethyl), 2'-F, 2'-O[2-(methylamino)-2-oxoethyl] (2'-O-NMA), 2'-S-methyl, 2'-O—CH2-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-F arabinose, 2'-OMe arabinose, arabinose, and any combinations thereof.
10. The oligonucleotide of paragraph 8 or 9, wherein the sugar medication is located within the loop, at the 5' or 3' end of the loop; within the stem; within the sequence 5'-GGAG-3'; or at $N^1$, $N^2$, $N^3$, $N^4$, $N^5$, $N^6$, $N^7$, $N^8$, or $N^9$.
11. The oligonucleotide of any of paragraphs 1-10, wherein the oligonucleotide comprises at least one non-phosphodiester intersugar linkage selected from the group consisting of phosphorothioate, phosphorodithioate, alkyl-phosphonate and phosphoramidate linkage.
12. The oligonucleotide of any of paragraphs 8-11, wherein the at least one modified intersugar linkage is located within the loop, at the 5' or 3' end of the loop; within the stem; within the sequence 5'-GGAG-3'; at the 5' position of the 5' most guanosine of the sequence 5'-GGAG-3'; or at 5' or 3' position of $N^1$, $N^2$, $N^3$, $N^4$, $N^5$, $N^6$, $N^7$, $N^8$, or $N^9$.
13. The oligonucleotide of any of paragraphs 1-12, wherein the oligonucleotide comprises a nucleobase modification selected from the group consisting of inosine, thymine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino) adenine, 8-(halo)adenine, 8-(hydroxyl)adenine, 8-(thioalkyl)adenine, 8-(thiol)adenine, $N^6$-(isopentyl) adenine, $N^6$-(methyl)adenine, $N^6$,$N^6$-(dimethyl)adenine, 2-(alkyl)guanine,2-(propyl)guanine, 6-(alkyl) guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza) cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl) uracil, 5-(alkyl)uracil, 5-(alkynyl)uracil, 5-(allylamino) uracil, 5-(aminoallyl)uracil, 5-(aminoalkyl)uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo) uracil, dihydrouracil, $N^3$-(methyl)uracil, 5-uracil (i.e., pseudouracil), 2-(thio)pseudouracil,4-(thio)pseudouracil,2,4-(dithio)psuedouracil,5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio) pseudouracil, 5-(methyl)-4-(thio)pseudouracil, 5-(alkyl)-2,4-(dithio)pseudouracil, 5-(methyl)-2,4-(dithio) pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl) isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl) phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, A-(methyl)benzimidazole, 6-(azo)thymine, 2-pyridinone, 5-nitroindole, 3-nitropyrrole, 6-(aza)pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, or any O-alkylated or N-alkylated derivatives thereof.

14. The oligonucleotide of any of paragraphs 8-13, wherein the nucleobase modification is located within the loop, at the 5' or 3' end of the loop; within the stem; within the sequence 5'-GGAG-3'; or at $N^1$, $N^2$, $N^3$, $N^4$, $N^5$, $N^6$, $N^7$, $N^8$, or $N^9$.

15. The oligonucleotide of any of paragraphs 1-14, wherein the oligonucleotide is conjugated with a ligand selected from the group consisting of polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), a cell-permeation agent (e.g., a.helical cell-permeation agent), and any combinations thereof 16. The oligonucleotide of any of paragraphs 8-15, wherein the ligand is conjugated at the 5' end or 3' end of the oligonucleotide, in the loop, within the stem, within the sequence 5'-GGAG-3'; or within the sequence 5'-$N^1N^2N^3N^4N^5N^6N^7N^8N^9$-3'.

17. The oligonucleotide of any of paragraphs 1-16, wherein the oligonucleotide comprises a fluorescent reporter (e.g., a fluorophore).

18. The oligonucleotide of paragraph 17, wherein the fluorescent reporter is selected from the group consisting of fluorescein dyes, rhodamine dyes, naphthylamine dyes, coumarins, acridines, N-(p(2-benzoxazolyl) phenyl)maleimide; cyanines, 1H,5H,11H, 15H-Xantheno[2,3,4-ij: 5,6,7-i'j']diquinolizin-18-ium; 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like.

19. The oligonucleotide of paragraph 17 or 18, wherein the fluorescent reporter is conjugated at the 5' end or 3' end of the oligonucleotide, within the loop, within the stem, within the sequence 5'-GGAG-3'; or within the sequence 5'-$N^1N^2N^3N^4N^5N^6N^7N^8N^9$-3'.

20. The oligonucleotide of any of paragraphs 1-18, wherein the oligonucleotide comprises a monophosphate, diphosphate, triphosphate, monothiophosphate (phosphorothioate); monodithiophosphate (phosphorodithioate), phosphorothiolate; alpha-thiotriphosphate; beta-thiotriphosphate; gamma-thiotriphosphate; P-N phosphoramidate $(HO)(NH_2)(O)P—O-5')$; 5'O—N phosphoramidate; $((HO)_2(O)P—NH-5')$; alkylphosphonate (R(OH)(O)P—O-5', wherein R is alkyl); and alkyletherphosphonate (R(OH)(O)P—O-5', wherein R is alkylether) at the 5' end.

21. The oligonucleotide of any of paragraphs 1-20, wherein the 5' end of the oligonucleotide is covalently linked to the 3' end of the oligonucleotide.

22. The oligonucleotide of any of paragraphs 1-21, wherein $N^1$ and $N^3$ are independently selected purines and $N^7$, $N^8$, and $N^9$ are independently selected pyrimidines.

23. The oligonucleotide of any of paragraphs 1-22, wherein $N^2$ and $N^4$ are guanosine and $N^5$ is adenosine.

24. The oligonucleotide of any of paragraphs 1-23, wherein $N^1$ and $N^5$ are adenosine; $N^3$ is adenosine or uridine; $N^2$ and $N^4$ are guanosine; and $N^6$, $N^7$, $N^8$, and $N^9$ are uridine.

25. The oligonucleotide of paragraph 22, wherein the oligonucleotide comprises the sequence 5'-GGGCAGAGAUUUUGCCCGGAG-3' (SEQ ID NO: 16) or 5'-GGGGUAGUGAUUUUACCCUGGAG-3' (SEQ ID NO: 17).

26. The oligonucleotide of any of paragraphs 1-21, wherein $N^1$, $N^3$, $N^8$, and $N^9$ are independently selected pyrimidines and $N^7$ is a purine.

27. The oligonucleotide any of paragraphs 1-21 or 26, wherein $N^1$, $N^3$, and $N^6$ are uridine; $N^2$, $N^5$, and $N^7$ are adenosine; $N^4$ is guanosine; and $N^8$ and $N^9$ are cytosine.

28. The oligonucleotide of paragraph 27, wherein the oligonucleotide comprises the sequence 5'-GGGGUCUAUGAUACCACCCCGGAG-3' (SEQ ID NO: 18).

29. The oligonucleotide of any of paragraphs 1-28, wherein the oligonucleotide inhibits the activity of a Lin28 polypeptide 30. A pharmaceutical composition comprising a oligonucleotide of any of paragraphs 1-29 and a pharmaceutically acceptable carrier.
31. A method for promoting miRNA processing of pri-miRNA to mature miRNA in a cell, the method comprising contacting a cell with an isolated oligonucleotide of any of paragraphs 1-29.
32. The method of paragraph 31, wherein the mature miRNA is a tumor suppressor miRNA.
33. The method of any of paragraphs 31 or 32, wherein the mature miRNA is a member of the let-7 miRNA family.
34. The method of any of paragraphs 31-33, wherein the cell comprises a cancer cell.
35. The method of paragraph 34, wherein the cancer cell comprises a cancer cell line.
36. The method of paragraph 34 or 35, wherein the cancer cell is a pre-cancer cell, a malignant cancer cell, a therapy resistant cancer cell or a cancer stem cell.
37. The method of any of paragraphs 34-36, wherein the cancer cell is selected from the group consisting of: a breast cancer cell, a lung cancer cell, lung adrenocarcinoma cell, a head and neck cancer cell, a bladder cancer cell, a chronic myelogenous leukemia (CML) cell, a stomach cancer cell, a nervous system cancer cell, a bone cancer cell, a bone marrow cancer cell, a brain cancer cell, a colon cancer cell, a colorectal cancer cell, a esophageal cancer cell, a endometrial cancer cell, a gastrointestinal cancer cell, a genital-urinary cancer cell, a stomach cancer cell, a lymphomas cell, a melanoma cell, a glioma cell, a bladder cancer cell, a pancreatic cancer cell, a gum cancer cell, a kidney cancer cell, a retinal cancer cell, a liver cancer cell, a nasopharynx cancer cell, an ovarian cancer cell, an oral cancer cell, a bladder cancer cell, a hematological neoplasm cell, a follicular lymphoma cell, a cervical cancer cell, a multiple myeloma cell, a B-cell chronic lymphcylic leukemia cell, a B-cell lymphoma cell, an osteosarcoma cell, a thyroid cancer cell, a prostate cancer cell, a colon cancer cell, a prostate cancer cell, a skin cancer cell, a stomach cancer cell, a testis cancer cell, a tongue cancer cell, an uterine cancer cell, and any combinations thereof.
38. The method of any of paragraphs 31-37, wherein the cell is a human cell.
39. The method of any of paragraphs 31-38, wherein said contact is in vitro, in vivo, in a subject or ex vivo.
40. The method of any of paragraphs 39, wherein the in vivo contact is in a subject, which subject is identified to have, or be at risk of an increase in the level of expression and/or activity of Lin-28 or the subject is identified to have, or be at risk of a reduction of the level or expression and/or activity, or loss of expression of a tumor suppressor miRNA.
41. The method of paragraph 39 or 40, wherein the in vivo contact is in a human.
42. A method of treating or preventing a cancer in a subject, comprising administering to a subject an effective amount of an isolated oligonucleotide of any of paragraphs 1-29.
43. The method of paragraph 42, wherein the subject is identified to have, or be at risk of an increase in the level of expression and/or activity of Lin28 or the subject is identified to have, or be at risk of a reduction of the level or expression and/or activity, or loss of expression of a tumor suppressor miRNA.
44. The method of paragraph 42 or 43, further comprising a diagnosing a subject for ac cancer prior to administrating the oligonucleotide.
45. The method of any of paragraphs 42-44, wherein the tumor suppressor miRNA is a member of the let-7 miRNA family.
46. The method of any of the paragraphs 42-45, wherein the cancer is a pre-cancer, malignant cancer, therapy resistant cancer or a cancer comprising cancer stem cells.
47. The method of any of the paragraphs 42-46, wherein the cancer is selected from the group consisting of breast cancer, lung cancer, head and neck cancer, bladder cancer, stomach cancer, cancer of the nervous system, bone cancer, bone marrow cancer, brain cancer, colon cancer, colorectal cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, B-cell chronic lymphcylic leukemia, B-cell lymphoma, osteosarcomas, thyroid cancer, prostate cancer, colon cancer, prostate cancer, skin cancer, stomach cancer, testis cancer, tongue cancer, or uterine cancer.
48. The method of any of paragraphs 42-47, wherein said administering is intravenous, intradermal, intramuscular, intraarterial, intralesional, percutaneous, subcutaneous, or by aerosol.
49. The method of any of paragraphs 42-48, further comprising administering to the subject one or more additional therapies.
50. The method of paragraph 49, wherein additional therapies are selected from the group consisting of surgery, chemotherapy, radiotherapy, thermotherapy, immunotherapy, hormone therapy or laser therapy.
51. The method of any of the paragraphs 42-50, wherein the subject is a human.
52. An isolated polypeptide comprising amino acids 31-187 of full length Lin28A or Lin28B polypeptide, wherein the isolated polypeptide is less than 200 amino acids in length.
53. The isolated polypeptide of paragraph 52, wherein the isolated polypeptide further comprises a deletion of at least five amino acids between positions 121 to 138 of full length Lin28A or Lin28B polypeptide.
54. The isolated polypeptide of paragraph 52 or 53, wherein the isolated polypeptide comprises at least one modification selected from a non-natural amino acid, a D-amino acid, a β amino acid, a chemically modified amino acid, a modified amide linkage, a tag amino acid sequence, and any combinations thereof.
55. The isolated polypeptide of any of paragraphs 52-54, wherein the polypeptide is useful for stem cell reprogramming.
56. The isolated polypeptide of any of paragraphs 52-55, wherein the isolated polypeptide is selected from the group consisting of
MHHHHHHENLYFQGSGAAEKAPEEAPP-DAARAADEPQLLHGAGICKWFNVRMGFG FLSMTARAGVALDPPVDVFVHQSKLHMEG-FRSLKEGEAVEFTFKKSAKGLESIRVTG PGGVFCIGSERRPKGKNMQKRRSKGDRCYN-CGGLDHHAKECKLPPQPKKCHFCQSI NHMVASCPLKAQQGPSS (SEQ ID NO: 2);

MHHHHHHENLYFQGSGAADEPQLLHGAGICK-WFNVRMGFGFLSMTARAGVALDPP VDVFVHQSKLHMEGFRSLKEGEAVEFTFKK-SAKGLESIRVTGPGGVFCIGSERRPKG GDRCYNCGGLDHHAKECK-LPPQPKKCHFCQS-INHMVASCPLKAQQGPSSQGK (SEQ ID NO: 3);

MHHHHHHENLYFQGSGEEPEKLPGLAE-DEPQVLHGTGHCKWFNVRMGFGFISMISR EGNPLDIPVDVFVHQSKLFMEGFRSLKEG-EPVEFTFKKSPKGLESIRVTGPGGSPCLGS ERRPKGKTLQKRKPKGDRWRRQDLL-MDQMWTVREEESRMIPRCYNCGGLDHHAK ECSLPPQPKKCHYCQSIMHMVANCPHK-LAAQLPASS (SEQ ID NO: 4);

MHHHHHHENLYFQGSGAAEEAPEEAPED-AARAADEPQLLHGAGICKWFNVRMGFG FLSMTARAGVALDPPVDVFVHQSKLHMEG-FRSLKEGEAVEFTFKKSAKGLESIRVTG PGGVFCIGSERRPKGKSMQKRRSKGDRCYN-CGGLDHHAKECKLPPQPKKCHFCQSIS HMVASCPLKAQQGPSAQGK (SEQ ID NO: 5);

MHHHHHHENLYFQGSGAADEPQLLHGAGICK-WFNVRMGFGFLSMTARAGVALDPP VDVFVHQSKLHMEGFRSLKEGEAVEFTFKK-SAKGLESIRVTGPGGVFCIGSERRPKG GDRCYNCGGLDHHAKECKLPPQPKKCHFCQ-SISHMVASCPLKAQQGPSAQGK (SEQ ID NO: 6);

MHHHHHHENLYFQGSGEEPGKLPE-PAEEESQVLRGTGHCKWFNVRMGFGFISMIN-REGSPLDIPVDVFVHQSKLFMEGFRSLKEG-EPVEFTFKKSSKGLESIRVTGPGGSPCLGS ERRPKGKTLQKRKPKGDRCYNCG-GLDHHAKECSLPPQPKKCHYCQSIMHM-VANCP HKNVAQPPASSQGR (SEQ ID NO: 7);

MHHHHHHENLYFQGSGPAEEESQVLRGTGHCK-WFNVRMGFGFISMINREGSPLDIPV DVFVHQSKLFMEGFRSLKEG-EPVEFTFKKSSKGLE-SIRVTGPGGSPCLGSERRPKGGDRCYNCGGL DHHAKECSLPPQPKKCHYCQSIMHM-VANCPHKNVAQPPASSQGR (SEQ ID NO: 8);

GSGAAEKAPEEAPPDAARAADEPQLLHGAG-ICKWFNVRMGFGFLSMTARAGVALDP PVDVFVHQSKLHMEGFRSLKEGEAVEFTFKK-SAKGLESIRVTGPGGVFCIGSERRPKG KNMQKRRSKGDRCYNCGGLDHHAKECK-LPPQPKKCHFCQSINHMVASCPLKAQQGPSS (SEQ ID NO: 9);

GSGAADEPQLLHGAGICKWFNVRMGFGFL-SMTARAGVALDPPVDVFVHQSKLHME GFRSLKEGEAVEFTFKKSAKGLE-SIRVTGPGGVFCIGSERRPKGGDRCYNCG-GLDHHAKECKLPPQPKKCHFCQSINHM VASCPLKAQQGPSSQGK (SEQ ID NO: 10);

GSGEEPEKLPGLAEDEPQVLHGTGHCK-WFNVRMGFGFISMISREGNPLDIPVDVFVH QSKLFMEGFRSLKEGEPVEFTFKKSPKGLE-SIRVTGPGGSPCLGSERRPKGKTLQKRK PKGDRWRRQDLL-MDQMWTVREEESRMIPRCYNCG-GLDHHAKECSLPPQPKKCHYCQSIMHM-VANCPHKLAAQLPASS (SEQ ID NO: 11);

GSGAAEEAPEEAPEDAARAADEPQLLHGAG-ICKWFNVRMGFGFLSMTARAGVALDPPVD VFVHQSKLHMEGFRSLKEGEAVEFTFKK-SAKGLESIRVTGPGGVFCIGSERRPKG KSMQKRRSKGDRCYNCGGLDHHAKECK-LPPQPKKCHFCQSISHMVASCPLKAQQGP SAQGK (SEQ ID NO: 12);

GSGAADEPQLLHGAGICKWFNVRMGFGFL-SMTARAGVALDPPVDVFVHQSKLHME GFRSLKEGEAVEFTFKKSAKGLE-SIRVTGPGGVFCIGSERRPKGGDRCYNCG-GLDHHAKECKLPPQPKKCHFCQSIS HMVASCPLKAQQGPSAQGK (SEQ ID NO: 13);

GSGEEPGKLPEPAEEESQVLRGTGHCK-WFNVRMGFGFISMINREGSPLDIPVDVFVHQ SKLFMEGFRSLKEGEPVEFTFKKSSKGLE-SIRVTGPGGSPCLGSERRPKGKTLQKRKP KGDRCYNCGGLDHHAKECSL PPQPKKCHYCQSIMHMVANCPHKNVAQP-PASSQGR (SEQ ID NO: 14); and GSGPAEEESQVLRGTGHCKWFNVRMGFGFIS-MINREGSPLDIPVDVFVHQSKLFMEGFRS LKEGEPVEFTFKKSSKGLESIRVT (SEQ ID NO: 15).

57. A crystalline molecule or molecular complex comprising a binding pocket of Lin28, wherein the Lin28 binding pocket is defined by structure coordinates binding pocket of Tables 1-3 and said Tables 1-3 being optionally varied by a rmsd of less than 1.5 Å or selected coordinates thereof.

58. The crystalline molecule or molecular complex of paragraph 57, wherein the Lin28 binding pocket comprises at least one amino acid selected from the group consisting of D71, E105, E106, F55, F73, F84, H75, K102, K45, K78, M51, R123, R50, R85, S100, W45, W46, and any combinations from Table 1-3, or selected coordinates thereof.

59. The crystalline molecule or molecular complex of paragraph 57 or 58, wherein the Lin28 binding pocket comprises the amino acids D71, E106, F55, F84, H75, K102, K45, K78, M51, R50, R85, S100, and W45; amino acids D71, E106, F55, F84, H75, K102, K78, M51, R50, R85, S100, and W45; or amino acids D71, E105, F55, F73, H75, K102, K78, M51, R123, R50, R85, S100, and W46 from Tables 1-3 or selected coordinates thereof.

60. A crystal comprising Lin28 complexed with a pre-let-7, wherein the crystal comprises structure coordinates of Tables 1-3.

61. A computer readable medium having Lin28 crystal structure coordinates of Tables 1-3 stored thereon.

62. A computer based-method for analysis of interaction of ligand with Lin28, the method comprising: providing Lin28 binding pocket of Tables 1-3, the Tables 1-3 being optionally varied by a rmsd of less than 1.5 Å, or selected coordinates thereof; providing a ligand structure to be fitted to the Lin28 binding pocket; and fitting the ligand structure to the Lin28 binding pocket, wherein the ligand structure is fitted to at least one atom of an amino acid selected from the group consisting of D71, D100, E105, F47, F55, F73, F84, G83, H75, K102, K192, K45, K78, M51, N48, R122, R123, R50, R85, S100, V49, W46, and any combinations thereof.

63. A screening assay for determining inhibitors of Lin28 activity, the method comprising contacting a polypeptide of any of paragraphs 52-56 with a test compound and selecting the compound that increases level of mature let-7 miRNA relative to a control.

64. The method of paragraph 63, wherein the test compound is selected from the group consisting of small organic or inorganic molecules; peptides; proteins; peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof.

65. The method of any of paragraphs 63-64, wherein the test compound has a molecular weight of less than 5000 Daltons (5 kD).
66. The method of any of paragraphs 63-65, wherein the test compound is tested at a concentration in the range of about 0.1 nM to about 1000 mM.
67. The method of any of paragraphs 63-66, wherein the method is a high-throughput screening method.
68. A compound selected by the method of any of paragraphs 63-67, and analogs, isomers, derivatives, and pharmaceutically acceptable salts thereof.
69. A method of purifiying a Lin28 polypeptide, the method comprising:
   (i) expressing a Lin28 polypeptide or fragment thereof from a vector in a cell;
   (ii) purifying the Lin28 polypeptide using cation exchange chromatography, wherin the cation exchange chromatography is using a buffer comprising about 20 mM BisTris about pH 6.0, about mM dithiothreitol (DTT), about 5% glycerol, and about 50 50 µM $ZnCl_2$, over 0.1-1M NaCl gradient.
70. The method of paragraph 69, comprising further purifying the Lin28 polypeptide or fragment thereof of step (ii) with size exclusion chromatography, wherin the size exclusion chromatography is using a buffer comprising about 20 mM BisTris about pH 6.0, about mM dithiothreitol (DTT), about 5% glycerol, and about 50 50 µM $ZnCl_2$.
71. The method of paragraph 69 or 70, wherein the cell is expressed in *E. coli.*
72. The method of any of paragraphs 69-71, wherein the expressed Lin28 polypeptide comprises a His-tag, wherein the His-tag is removed before purification by cation exchange chromatography.
73. The method of any of paragraphs 69-72, wherein the Lin28 polypeptide of fragment thereof is a polypeptide of any of paragraphs 52-56.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased","increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "Lin28" as used herein is also referred to in the art as aliases LIN-28A, FLJ12457, ZCCHC1, Lin-28A, CSDD1 and Lin-28 homolog (*C. elegans*). Human Lin-28 is encoded by nucleic acid corresponding to GenBank Accession No: AF521099 (SEQ ID NO: 66) or RefSeq ID: NM_024674 (SEQ ID NO: 67), and the human Lin-28 corresponds to protein sequence corresponding to RefSeq ID:AAM77751 (SEQ ID NO: 68). Human Lin-28 has a conserved Cold Shock Domain (CSD) between residues 39-112, and two CCHC domains; a type 1 CCHC domain between residues 137-154 and a type 2 CCHC domain between resides 159-176. As used herein, the term The term "Lin-28B" as used herein refers to a homologue of Lin28 and is also known in the art as CSDD2, FLJ16517, or Lin-28.2. There are two isoforms of, B, differing in their 5' exons, have been reported, the long isoform (Lin-28B-L also known as isoform 1 or identifier: Q6ZN17-1, corresponding to SEQ ID NO: 69 herein) which has two retroviral-type CCHC zinc-finger motifs and a truncated cold-shock domain, and a short isoform (Lin-28B-S, also known as isoform 2 or identifier: Q6ZN17-2, corresponding to SEQ ID NO: 70 herein) which preserves the two retroviral-type CCHC zinc-finger motifs but contains a truncated cold-shock domain (i.e. lacks 70 N-terminal amino acids as compared to the Lin-28B-L isoform). Human Lin28B-L has a conserved Cold Shock Domain (CSD) between residues 29-102, and two CCHC domains; a type 1 CCHC domain between residues 127-144 and a type 2 CCHC domain between residues 149-166. Human Lin-28B-L is encoded by nucleic acid corresponding to GenBank Accession No: AK131411 or RefSeq ID: NM_001004317 and the human Lin-28B corresponds to protein sequence corresponding to RefSeq ID: NP_001004317.

The terms "microRNA" or "miRNA" or "miR" are used interchangeably herein refer to endogenous RNA molecules, which act as gene silencers to regulate the expression of protein-coding genes at the post-transcriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

During miRNA maturation in animals, the primary transcript is first processed to a stem-loop precursor and then the stem-loop is processed to yield a mature miRNA of about 22 nucleotides. These molecules can direct the cleavage of mRNA or they can interfere with productive translation of the mRNA, either of which results in reduced protein accumulation and hence the miRNAs are able to modulate gene expression and related cellular activities. miRNAs are important in development and differentiation, and thus the altered expression of miRNAs could be used to alter development and differentiation during tissue engineering and other applications. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. Mimetics of miRNAs include, artificial miRNAs, and siRNAs are inefficient and are not effective for many small RNA sequences.

The term "pri-miRNA" refers to a precursor microRNA molecule having a microRNA sequence in the context of microRNA flanking sequences. A precursor microRNA, also referred to as large RNA precursors, are composed of any type of nucleic acid based molecule capable of accommodating the microRNA flanking sequences and the microRNA sequence. Examples of precursor microRNAs and the individual components of the precursor (flanking sequences and microRNA sequence) are provided herein. The invention, however, is not limited to the examples provided. The invention is based, at least in part, on the discovery of an important component of precursor microRNAs, that is, the microRNA flanking sequences. The nucleotide sequence of the precursor and its components may vary widely. In one aspect a precursor microRNA molecule is an isolated nucleic acid; including microRNA flanking sequences and having a stem-loop structure with a microRNA sequence incorporated therein.

A precursor microRNA molecule may be processed in vivo or in vitro to produce a mature microRNA (miRNA). A precursor microRNA molecule is processed in a host cell by a ribonuclease enzyme or enzymes. One example of a ribonuclease enzyme which processes precursor microRNA molecules is the RNase II ribonuclease Dicer. [0075] The term "pre-miRNA" refers to the intermediate miRNA species from the processing of a pre-miRNA to a mature miRNA. Pre-miRNAs are produced from the processing of a pri-miRNA in the nucleus into a pre-miRNA. PremiRNAs undergo additional processing in the cytoplasm to form mature miRNA. Pre-miRNAs are approximately 70 nucleotides long, but can be less than 70 nucleotides or more than 70 nucleotides.

The term "microRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure. Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

The microRNA flanking sequences may be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences. The microRNA flanking sequences within the precursor microRNA molecule may flank one or both sides of the stemloop structure encompassing the microRNA sequence. Thus, one end (i.e., 5') of the stem-loop structure may be adjacent to a single flanking sequence and the other end (i.e., 3') of the stem-loop structure may not be adjacent to a flanking sequence. Preferred structures have flanking sequences on both lo ends of the stem-loop structure. The flanking sequences may be directly adjacent to one or both ends of the stem-loop structure or may be connected to the stem-loop structure through a linker, additional nucleotides or other molecules.

As used herein, the term "let-7" refers to the nucleic acid encoding the let-7 miRNA family members and homologues and variants thereof including conservative substitutions, additions, and deletions therein not adversely affecting the structure or function. Preferably, let-7 refers to the nucleic acid encoding let-7 from *C. elegances* (NCBI Accession No. AY390762), most preferably, let-7 refers to the nucleic acid encoding a let-7 family member from humans, including but not limited to, NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity. Exemplary let-7 family member miRNAs include, but are not limited to, Let-7, Let-7a-1, Let-7a-2, Let-7a-3, Let-7b, Let-7c, Let-7d, Let-7e, Let-7f-1, Let-7f-2, Let-7g, Let-7i, and miR-98.

The term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a nonconventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or nonpolar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of a Lin-28 polypeptide to process the maturation of miRNA). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Eastern, Pa. (1990).

The term "functional" when used in conjunction with "derivative" or "variant" refers to a molecule such as a protein which possess a biological activity (either functional or structural) that is substantially similar to a biological activity of the entity or molecule is a functional derivative or functional variant thereof. The term functional derivative is intended to include the fragments, analogues or chemical derivatives of a molecule.

A molecule is said to be "substantially similar" to another molecule if both molecules have substantially similar structures or if both molecules possess a similar biological activity, for example if both molecules are able to deliver a target antigen to the cytosol of a cell in the absence of PA and without being fused to the target antigen. Thus, provided that two molecules possess a similar activity, are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical.

As used herein, the term "non-conservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

The term "tumor" or "tumor cell" are used interchangeably herein, refers to the tissue mass or tissue type of cell that is undergoing abnormal proliferation.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see Example VII) (see also Freshney, Culture of Animal Cells: A Manual of Basic Technique (3rd ed. 1994)).

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. Archival tissues, such as those having treatment or outcome history may also be used. As used herein, the term "biological sample" also refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples may be either paraffin-embedded or frozen tissue. The sample can be obtained by removing a sample of cells from a subject, but can also be accomplished by using previously isolated cells (e.g. isolated by another person), or by performing the methods of the invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples may be fresh, fixed, frozen, or embedded in paraffin.

The term "tissue" is intended to include intact cells, blood, blood preparations such as plasma and serum, bones, joints, muscles, smooth muscles, and organs.

As used herein, the term "treating" includes reducing or alleviating at least one adverse effect or symptom of a condition, disease or disorder associated with inappropriate proliferation, for example cancer. As used herein, the term treating is used to refer to the reduction of a symptom and/or a biochemical marker of in appropriate proliferation, for example a reduction in at least one biochemical marker of cancer by at least 10%. For example but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as affective treatments by the methods as disclosed herein.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1: Molecular Basis for Interaction of let-7 microRNAs with Lin28

Materials and Methods

Figure 2:
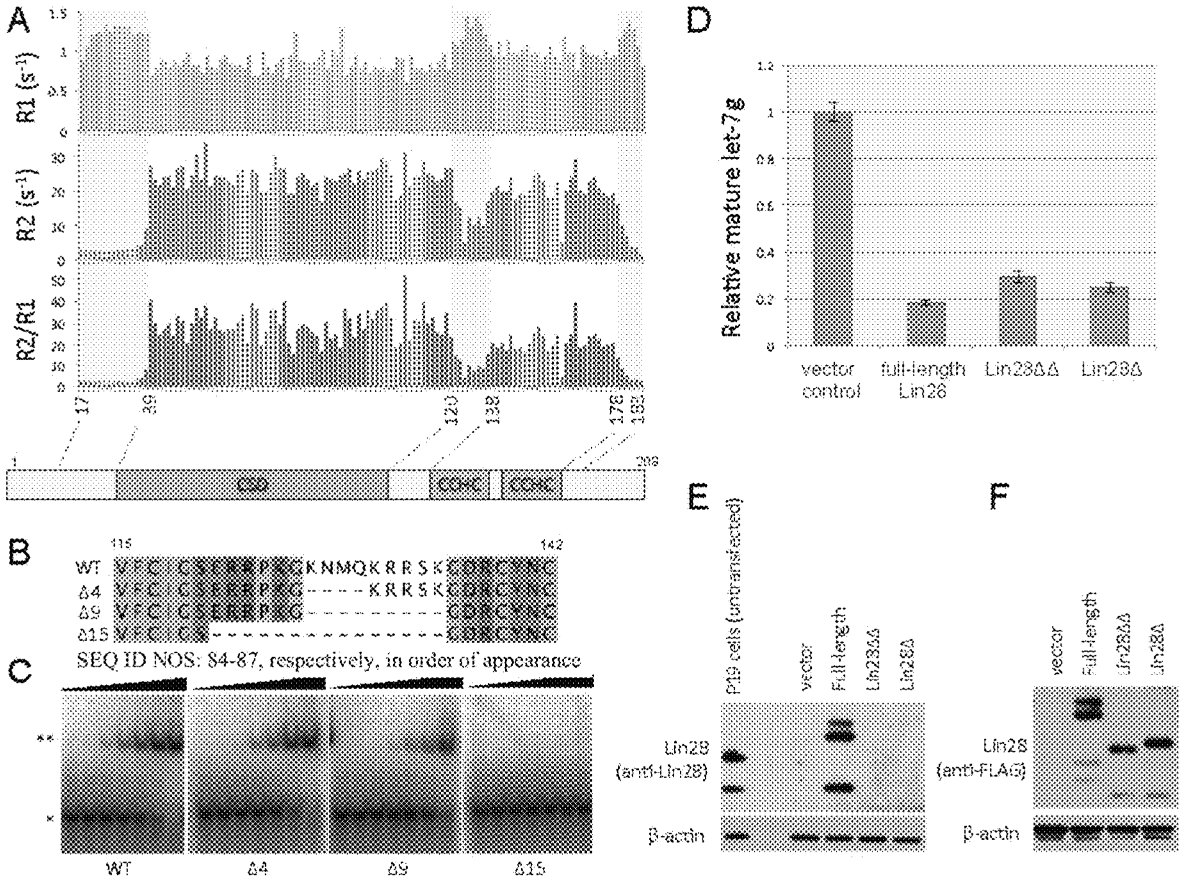
FIG. 2. Linker between CSD and CCHCx2 is flexible. See also FIG. 9. (A) Longitudinal (R1) and transverse (R2) relaxation rates and the ratio (R2/R1), plotted against the residue number. Relatively more dynamic regions are marked with a light yellow box. (B) Alignment of internal deletions in the linker, indicated with the number of amino acids deleted on left (SEQ ID NOS 84-87, respectively, in order of appearance). (C) EMSAs with preE-let-7d as probe, mixed with increasing concentrations (0.005, 0.02, 0.08, 0.3, 1.2, 5, 20 μM) of linker deletion constructs of Lin28(16-184): *, free probe; **, complex. (D) Quantitative RT-PCR results for in vivo levels of mature let-7g. Lin28Δ is truncated at both N and C termini. Lin28ΔΔ has both of the terminal extensions and the linker removed. The standard deviation is calculated from triplicate experiments; U6 RNA levels were used for normalization. (E) and (F) Western blots of Trizol bottom layer for transfections shown in (D). Anti-Lin28 antibodies do not recognize truncation constructs, so anti-FLAG was used in (F) to compare the relative expression levels of different Lin28 constructs.

Constructs: All Lin28 crystallization constructs were derived from mouse Lin28a (NP_665832). Expression constructs are in pETDuet-1 (Novagen), with an N-terminal hexahistidine tag (SEQ ID NO: 71) followed by a TEV cleavage site. For NMR studies and electrophoretic mobility shift assays, Lin28 (residues 16-184) contained the wild-type linker sequence, unless otherwise noted. For crystallization a similar construct (35-187) with nine internally deleted residues in the linker (49) was used (FIG. 2B). Isolated CSD construct contains residues 16-126 and CCHCx2 construct contains residues 135-184.

Protein purification and complex preparation: Lin28 constructs derived from mouse Lin28a were purified after overexpression in *E. coli*, using Nickel affinity, cation exchange, and size exclusion chromatography. Specifically, Lin28 constructs were overexpressed in *E. coli* strain BL21 (DE3) Rosetta pLysS. After initial affinity chromatography step using Ni-NTA beads (Qiagen), His-tags were removed by incubating with recombinant TEV protease. Cation exchange chromatography (HiTrap S, GE Healthcare) was performed using a buffer containing 20 mM BisTris pH 6.0, 5 mM dithiothreitol (DTT), 5% glycerol, and 50 μM $ZnCl_2$, over 0.1-1M NaCl gradient. Further purification was accomplished by size exclusion chromatography (Superdex 200, GE Healthcare) in the same buffer. Complexes with RNA oligonucleotides were prepared for NMR studies and crystallization trials, by mixing at 1:1.2 (protein:RNA) molar ratio, and free RNA was removed by another size-exclusion chromatography step.

Electrophoretic Mobility Shift Assay: For preE probes, RNA oligonucleotides were synthesized (IDT), and full pre-miR probes were purified by PAGE after in vitro transcription followed by double ribozyme cleavage, as detailed in (Walker et al., 2003). RNAs were radiolabeled with ATI:[γ-$^{32}$P] using T4 polynucleotide kinase, incubated with protein in a buffer containing 20 mM Tris 7.5, 100 mM NaCl, 10 mM DTT, 50 μM $ZnCl_2$, 15 μg/μL yeast tRNA, and 1U/μL RNAse inhibitor.

Equilibrium Sedimentation: Complexes containing indicated protein and RNA constructs were purified as described above. Three concentrations ($Absorbance_{280}$=0.2, 0.4, 0.6) were measured for each complex. Data was collected on a Beckman Optima XL-A ultracentrifuge at 4 speeds (15, 18, 21, 24K RPM) and analyzed by fitting to a single-species model using Origin. Partial specific volumes for each complex was calculated by using NucProt (Voss and Gerstein, 2005).

NMR spectroscopy: All NMR samples were prepared as 0.5 mM Lin28 (16-184) and $preE_M$-let-7d complex, in a buffer containing 20 mM BisTris pH 7.0, 100 mM NaCl, 5% glycerol, 5 mM dithiothreitol, 50 μM $ZnCl_2$, and 0.2% sodium azide. Backbone distance restraints were obtained using uniform $^{15}N$, $^{13}C$-labeled protein in complex with unlabeled RNA, from 3D $^{15}N$-edited NOESY (mixing time=120 ms). To measure $^{15}NR_1$ and $R_2$, a sample containing $^{15}N$, $^{13}C$ and 85% $^2H$-labeled protein combined with unlabeled RNA was used with standard pulse schemes (Kay et al., 1989). Secondary chemical shifts were calculated by the comparing the recorded chemical shift to sequence adjusted random coil chemical shift (Schwarzinger et al., 2001). Sequence-specific chemical shifts for backbone atoms were determined for 157 residues (out of 166 total, including 13 prolines), using the TROSY versions of HNCA, HN(CO)CA, HNCACB, HN(CO)CACB, HNCO, and HN(CA)CO, using a $^{15}N$, $^{13}C$ and 85% $^2H$-labeled protein combined with unlabeled RNA. Experiments were conducted at 30° C. on Bruker spectrometers equipped with cryogenic probes, operating at 1H frequencies of 600 MHz (sequence assignment and relaxation experiments) or 750 MHz (NOESYs).

All spectra were processed and analyzed with NMRPipe (Delaglio et al., 1995) and CCPnmr Analysis (Vranken et al., 2005).

Crystallography: Crystals of all three complexes were produced by vapor diffusion, using the hanging drop method. Concentrated complexes (10 mg/mL) were mixed 1 μL:1 μL with reservoir solution, and crystals grew overnight. Reservoir solution contained 0.6M $NaH_2PO_4$, 1.4M $K_2HPO_4$ and 5% glycerol for $preE_M$-let-7d and $preE_M$-let-7f-1 complexes; for $preE_M$-let-7g, it contained 0.1M Tris pH 8.0, 32% w/v PEG 4000, and 0.2M Sodium Acetate. Crystals were harvested with mother liquor supplemented with 20% glycerol and frozen in liquid nitrogen. Diffraction data was indexed and scaled using XDS (Kabsch, 2010) and SCALA (Evans, 2006) in a workflow provided by autoPROC (Vonrhein et al., 2011). Experimental phases were obtained for Lin28:pre-let-7d complex by anomalous scattering from zinc atoms (SAD), using HKL2MAP (Schneider and Sheldrick, 2002) and AutoSol (Terwilliger et al., 2009). The structures of Lin28: $preE_M$-let-7f-1 and Lin28: preEM-let-7g were solved by molecular replacement with Lin28: preEM-let-7d as search model using Phaser (McCoy et al., 2007). Density modification and NCS averaging over 6 or 2 copies were performed with PHENIX (Adams et al., 2010) to obtain electron density maps for model building with COOT (Emsley and Cowtan, 2004) and PHENIX was used for further refinement. Final rounds of refinement were carried out using BUSTER with local structure similarity restraints (LSSR) and TLS (Bricogne et al., 2011).

Dicer in vitro processing assay: Dicer expression construct (Addgene plasmid 19873) and purification are described as in (Landthaler et al., 2008), and radiolabeled pre-miR constructs were prepared similarly to EMSA probes. Dicer assays were carried out as described in (De and Macrae, 2011), using a buffer containing 20 mM Tris 7.5, 5% glycerol, 3.2 mM $MgCl_2$, 5 mM DTT, 50 mM NaCl, and 100 μM $ZnCl_2$.

MicroRNA in vivo processing assay: Ability of Lin28 constructs to block let-7 processing in cells was compared as outlined in (Viswanathan et al., 2008). Briefly, pri-let-7g was co-transfected with FLAG-tagged Lin28 constructs (25 ng unless otherwise noted) or vector control into 293T cells (12 well) using lipofectamine. Total RNA was isolated using TriZol reagent, treated with DNAse I, and quantitative RT-PCR was used with miRNA-specific stem-loop primers as previously described (Wan et al., 2010). Relative levels of mature miRNAs were analyzed by ΔΔCt method, and normalized by U6 snRNA levels.:

Accession numbers: Coordinates and structure factors for the structures of Lin28:pre$E_M$-let-7d, Lin28:pre$E_M$-let-7f-1, and Lin28:pre$E_M$-let-7g complexes are disclosed in Tables 1-3 and have been deposited with the Protein Data Bank under accession codes 3TRZ, 3TS0, and 3TS2.

Results and Discussion

Figure 8:
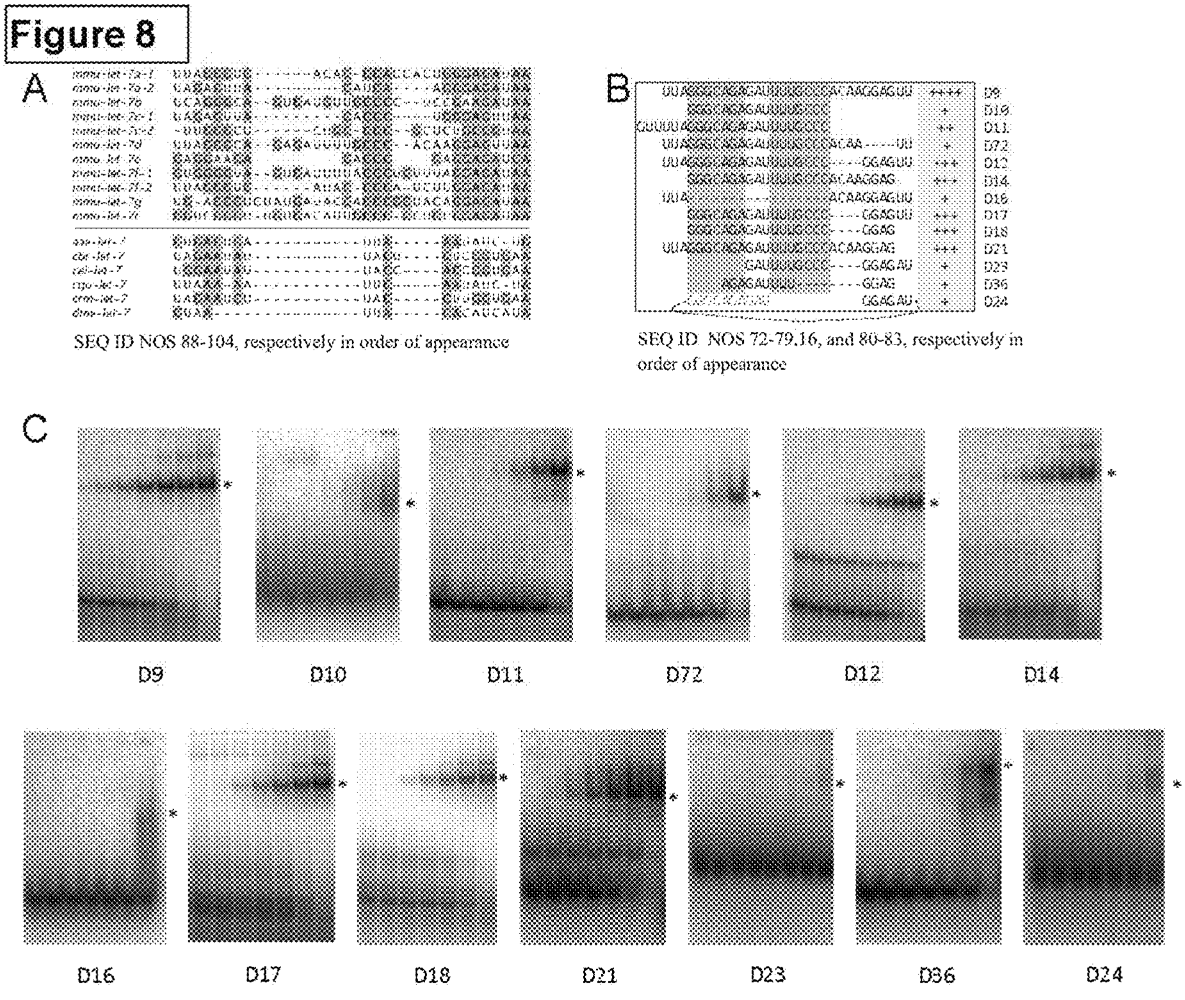
FIG. 8. Mapping of let-7 precursors for binding to Lin28, Related to FIG. 1. (A) Sequence alignment of pre-elements (preEs) from let-7 homologs. Upper block contains mouse homologs, and the lower block contains dme (*Drosophila melanogaster*), crm (*Caenorhabditis remanei*), cqu (*Culex quinquefasciatus*), cel (*Caenorhabditis elegans*), cbr (*Caenorhabditis briggasae*), and aae (*Aedes aegypti*). The colors follow Clustalx scheme. Sequences are SEQ ID NO NOS 88-104, respectively, in order of appearance. (B) Alignment of the tested oligonucleotide sequences for electrophoretic mobility shift assays. Scores for binding are defined by Kd ranges: ++++, 0.2-1.5 μM; +++, 1.5-3 μM; ++, 3-15 μM; +, >15 μM. D24 starts with GGAG with the grey sequence attached to the 3' end of the GGAG motif. Sequences are SEQ ID NO NOS 72-79, 16, and 80-83, respectively, in order of appearance. (C) Representative EMSAs using probes indicated, titrated with increasing concentrations of Lin28(16-184) from left to right (8 nM, 33 nM, 130 nM, 520 nM, 2.1 μM, 8.3 μM, 33.3 μM). Binding affinities were scored using the major complex band (marked with an asterisk at the right side). Other minor bands sometimes appear, but they are not reproducible and seem to depend on the protein/RNA batch.

Two discrete binding sites in pre-let-7 for Lin28 binding: As a first step to understanding how pre-let-7 is recognized by Lin28, the inventors tested a series of deletions in pre-let-7d for binding to the protein. Pre-let-7d has a relatively high affinity for Lin28 both in vivo and in vitro (Hagan et al., 2009, Heo et al., 2009,Newman et al., 2008), and secondary structure predictions indicate that it has the most stable preE-stem among mouse pre-let-7s, without interrupting bulges (Markham and Zuker, 2005). The inventors focused their analysis on the preE, as mutagenesis studies had indicated its importance in direct association with Lin28 (Heo et al., 2009, Newman et al., 2008, Piskounova et al., 2008, Rybak et al., 2008). Innetos discovered that an isolated preE segment, containing none of the mature-region nucleotides, can bind Lin28 and that two distinct regions are critical for binding to Lin28, thereby defining a minimal preE-let-7d (pre$E_M$-let-7d) sufficient for high-affinity binding (FIG. 1C, 8B-C). The first required region includes the preE-stem and the preE-loop; truncating the stem reduces binding. The other is the GGAG motif, which occurs at the 3' end of the preE bulge. Although overall preE sequence conservation is low, even within the preE stem and loop, the GGAG tetranucleotide element is well conserved throughout the let-7 family (FIG. 8A). Inventors' mapping results indicated that the GGAG element provides an independent binding site, as deleting the neighboring nucleotides, thereby altering the distance to the CSD binding site, does not abolish Lin28 binding. Without wishing to be bound by a theory, the presence of two independent binding sites can explain how diverse preE-let-7s containing variable linker sequences can all bind Lin28 with high specificity and affinity.

Figure 9:
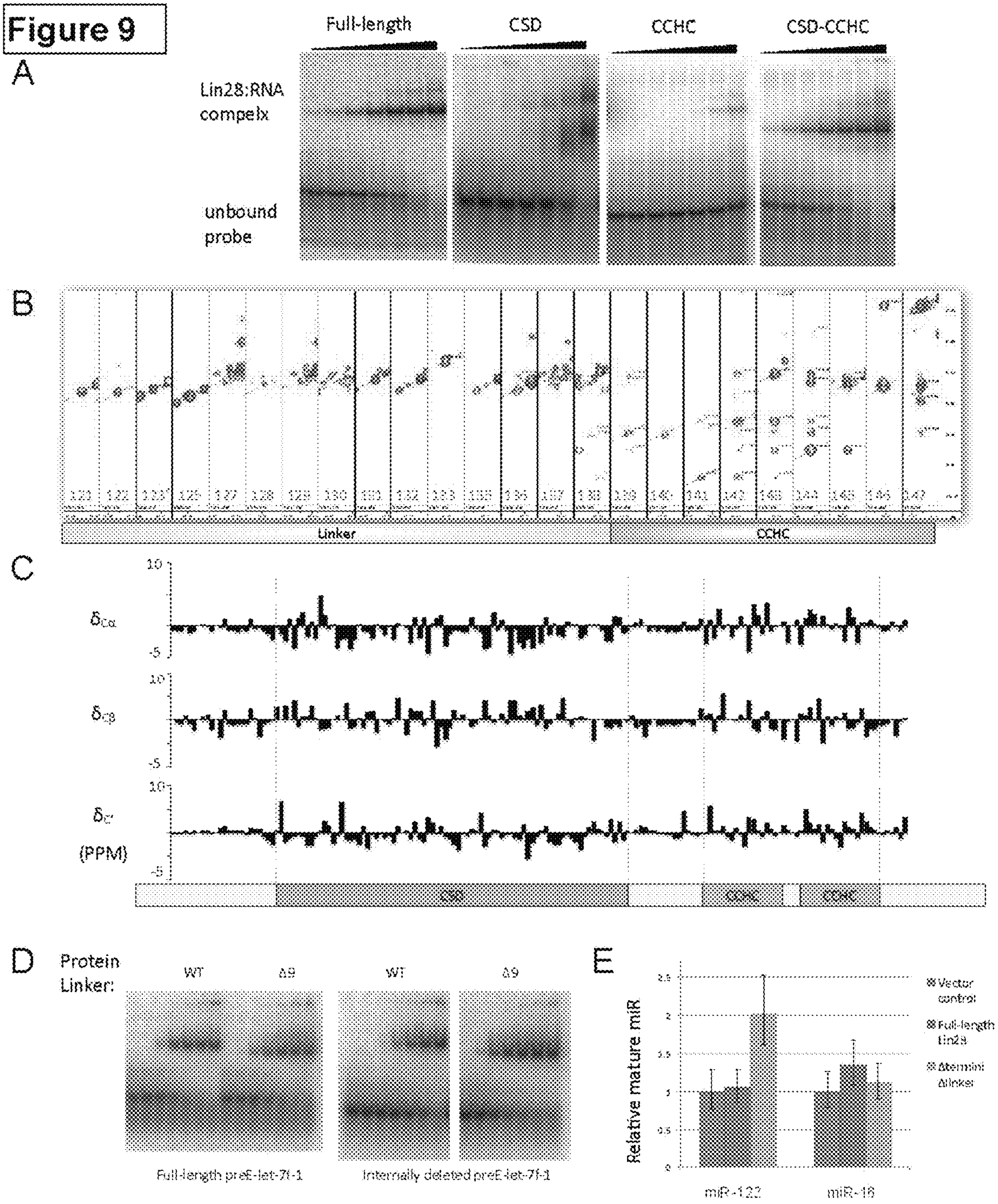
FIG. 9. Domain mapping and structural analysis of Lin28 protein, Related to FIG. 2. (A) EMSA of Lin28 truncations. Full-length (1-209) and CSD-CCHC (16-184) constructs have comparable affinity but isolated CSD (16-126) or isolated CCHCx2 (134-184) do not. Full-length preE-let-7d was used as probe, titrated with protein constructs indicated (left to right: 8 nM, 33 nM, 130 nM, 520 nM, 2.1 μM, 8.3 μM, 33.3 μM). (B) $^{15}$N-NOESY of the linker region. Homonuclear 1H/1H NOE spectral strips belonging to the residue numbers marked in red were taken from a 3D 15N-selected NOESY-HSQC, and only the amide region is shown for inter-residue backbone NOEs. Diagonal peaks are marked with a diagonal line and crosspeaks are marked with a cross. The linker region is missing inter-residue NOEs, while CCHC has amide-amide interactions evident from crosspeaks. (C) Plot of secondary shifts for Cα, Cβ, and C' vs. residue number. Domain boundaries, consistent as in FIG. 2A, are marked with dashed grey lines. (D) EMSA of protein linker deletion constructs. Increasing amounts of protein (Lin28 35-187, with or without 9-residue internal deletion in the linker region) were added to radioactively labeled fragment of pre-let-7f-1 indicated. The concentrations of protein in each lane are as follows: 5 nM, 20 nM, 78 nM, 313 nM, 1.2 μM, 50 μM, 20 μM. (E) In vivo processing assay of pri-miR-122 and pri-miR-16, similar to main FIG. 2D. 293T cells (12 well) were co-transfected with Lin28 (100 ng) with pri-miR-122 or pri-miR-15-16 (750 ng). Standard deviations from three experiments are shown.

Domains of Lin28 tethered to each other are sufficient for inhibiting let-7 processing: Lin28 has two folded regions, CSD and CCHCx2, connected by a positively charged linker of ~15 amino acids, with extensions of ~30 residues at both the amino and carboxy termini. Mutagenesis studies have implicated both folded domains in repression of let-7 (Heo et al., 2009, Piskounova et al., 2008). The region C-terminal to the CCHCx2 domain also promotes translation of certain mRNA targets (Jin et al., 2011, Peng et al., 2011, Qiu et al., 2010). Using limited proteolysis and electrophoretic mobility shift assay (EMSA), the inventors analyzed a series of truncation constructs of Lin28 to identify the essential region for interaction with preE-let-7. Both the N- and C-terminal regions can be removed without affecting affinity for RNA, but removal of either the CSD or the CCHCx2 abolishes high-affinity preE-let-7 binding (FIG. 9A).

The inventors used NMR spectroscopy to study the dynamics of Lin28:pre$E_M$-let-7d complexes in more detail (FIG. 2A). They measured longitudinal (R1) and transverse (R2) relaxation rates to probe backbone dynamics. The R2/R1 ratio, which is a measure of correlation time, is an indicator of tumbling rate in solution. This ratio is similar for the folded domains but much lower for the terminal segments and the intervening linker, indicating more rapid motion in those regions. This indicates that the linker sequence lacks secondary structure, an inference consistent with absence of inter-residue backbone NOE crosspeaks in $^{15}N$-NOESY (FIG. 9B). Comparing the Cα, Cβ, C' chemical shifts to random coil chemical shifts also indicates that the linker region lacks secondary structure (FIG. 9C). Deletion of up to 9 amino acids in the linker region supports binding to preE-let-7d or preE-let-7f-1, although further deletion prevents complex formation (FIG. 2B-C, 9D). This indicates that a Lin28 fragment (31-187) with N- and C-terminal truncations and a 9-residue linker deletion (Lin28ΔΔ), is sufficient for binding to preE-let-7 in vitro.

To test whether Lin28ΔΔ can inhibit let-7 processing in cells, the inventors compared the intracellular levels of processed mature let-7g when pri-let-7g is co-transfected with different Lin28 truncation constructs. Relative to vector alone, Lin28ΔΔ significantly reduces the level of mature let-7g, although not as much as the full-length Lin28 construct, probably due to slightly lower affinity (FIG. 2C-D). Processing of pri-miR-122 or pri-miR-16 is not inhibited by either Lin28 construct (FIG. 9E). Ectopically expressed Lin28 levels are similar to the endogenous levels observed in P19 cells and also among all Lin28 constructs (FIG. 2E-F). The Lin2844 construct is therefore comparable to the full-length protein in its ability to inhibit processing in vivo as well as to bind let-7 precursors in vitro.

Figure 10:
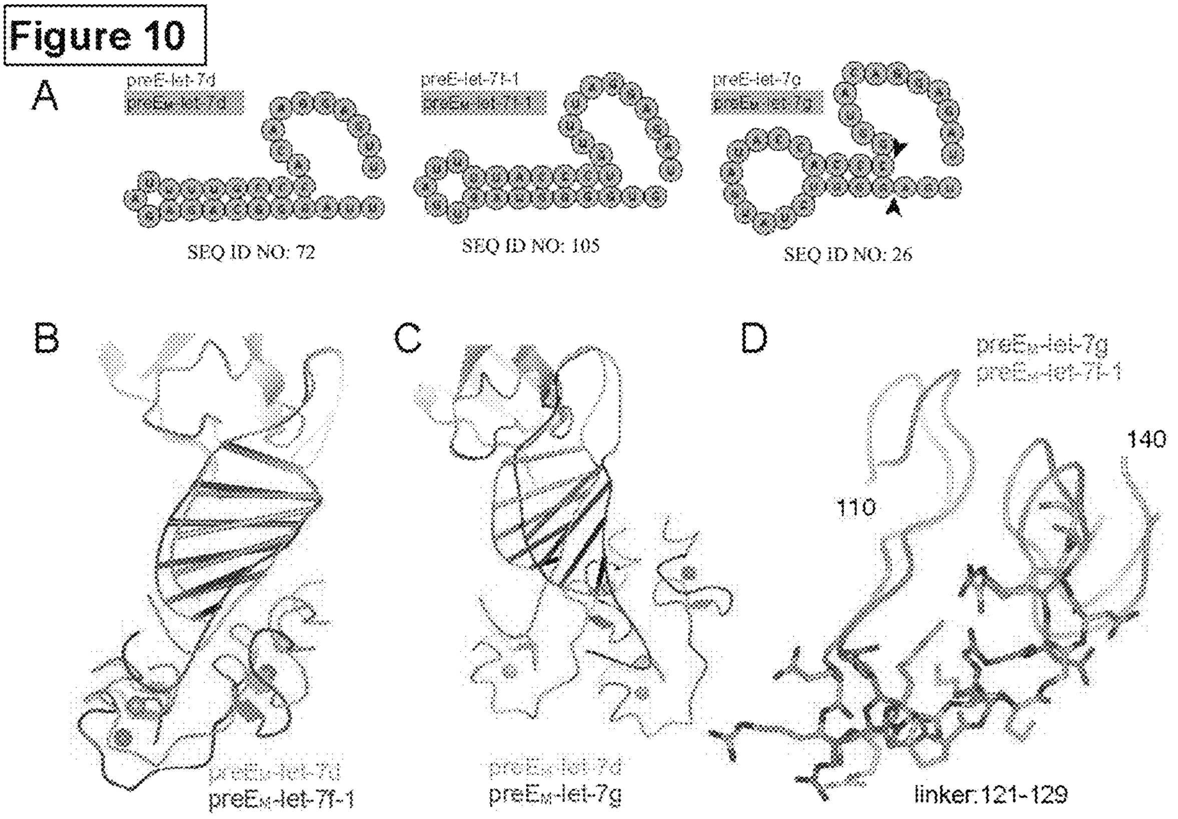
FIG. 10. Co-crystallization of Lin28 with sequences from three let-7 precursors, Related to FIG. 3. (A) Minimal preE (preE$_M$, orange) used for co-crystallization is shown for each let-7, in the context of the full-length preE. Grey nucleotides were removed to reduce flexibility for crystallization. For preE-let-7g, another GC pair was added at the position marked with arrow heads to stabilize the stem structure. From left to rigt, sequences are SEQ ID NO NOS 72, 105 and 106, respectively, in order of appearance. (B) Comparison of Lin28:preE-let-7d structure with preE-let-7f-1 complex shows that when the CSDs are superimposed, the CCHCx2 shifts according to the longer stem length of preE-let-7f-1. (C) Comparison of Lin28:preE-let-7d structure with preE-let-7g complex shows that due to differences near the ds-ss junction in the CSD binding region, the overall axis of the preE-stem is tilted. Again, the CCHCx2 follows the GGAG motif, indicating specific binding. (D) Interdomain linker of preE-let-7g is compared to preE-let-7f-1, and shows variability. Lack of clear density prevented modeling of the preE-let-7d linker. (E) Equilibrium sedimentation of WT and truncated linker constructs shows that the complexes are monomeric in solution, in contrast to what is seen in co-crystals.

High resolution crystal structures of Lin28 with let-7 microRNA: The inventors determined crystal structures of Lin2844 in complex with preEM-let-75 derived from let-7d, let-7f-1, and let-7g, at resolutions 2.9 Å, 2.8 Å, and 2.0 Å, respectively, from three different crystal forms (FIGS. 3, 10A). They used single-wavelength anomalous dispersion (SAD), with the bound zinc atoms as the anomalous scatterers, to determine the structure of the Lin28ΔΔ:pre$E_M$-let-7d complex; we determined the other structures by molecular replacement. While the overall architectures of the three complexes are similar (Lin28 Cα RMSD<1.3 Å), there are several local differences due to divergent RNA sequences (FIG. 10B-C, and see CSD and CCHC sections below).

The structures reveal that the CSD and CCHCx2 domains of Lin28 interact with two distinct single-stranded regions of the RNA fragment (FIG. 3A). The preE-loop encircles a protrusion of the CSD as a necktie would wrap around a collar, with the extensive contacts around the circle made possible by the presence of the preE-stem, which functions as the necktie's knot. The CCHC zinc knuckles interact with the GGAG motif at the 3' end, and several sequence-specific interactions shape the single stranded segment around the knuckles to introduce a distinctive kink in the RNA backbone. Positively charged surfaces on both domains interact with RNA throughout the complex (FIG. 3B).

The shortened linker between CSD and CCHCx2 is the most variable region among the different complexes (FIG. 10D). In all three crystal forms, the inventors discovered a domain swap in which the Lin28 CSD interacts with the loop of one RNA molecule and the CCHCx2 interacts with the GGAG of a second RNA (FIG. 3C). That is, each Lin28 monomer in the crystal interacts with distinct elements of two separate preEM-let-7d molecules. In sedimentation equilibrium ultracentrifugation experiments under more physiological conditions, we observe only monomeric complexes of Lin28:preE-let-7d, with or without internal deletions in the Lin28 linker (FIG. 10E). An unswapped complex conformation can be modeled with a small rearrangement of the C-terminal extension of the CSD (residues 112-121) and a rotation of the 7-residue linker to span the 18-30 Å distance between CSD and CCHCx2 on the same RNA (FIG. 3A). Moreover, the longer, 16-residue linker in wild-type Lin28 would accommodate even longer RNA substrates, including pre-let-7d without internal deletions. The monomeric model is also consistent with our observation that high affinity RNA binding by Lin28 requires both Lin28-binding sites on the same molecule (FIG. 1C). As all biochemical evidence points to a monomeric complex in solution, the description is restricted to a 1:1 complex, with CSD and CCHCx2 bound in cis to a single RNA.

Figure 11:
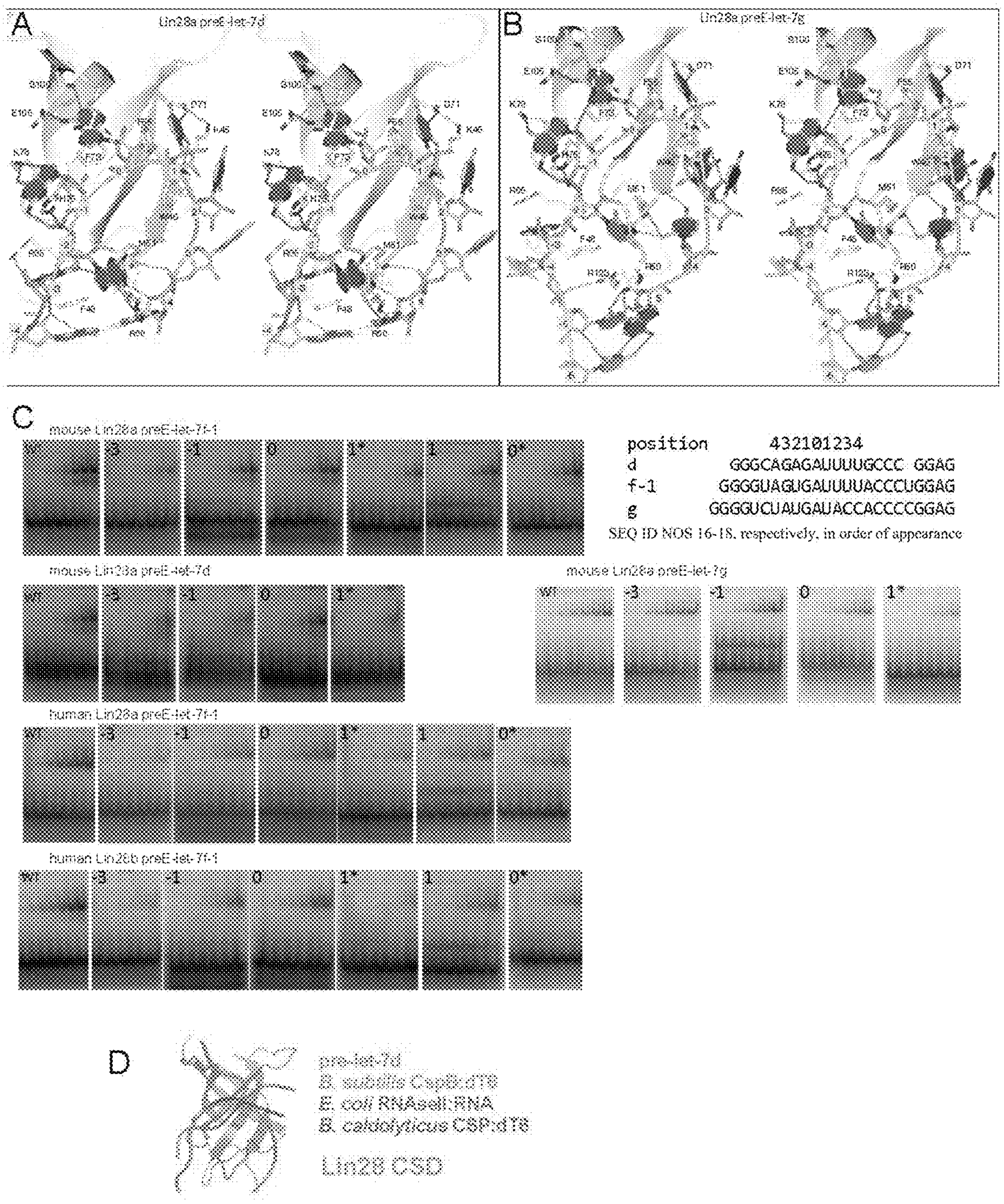
FIG. 11. CSD:RNA interactions, related to FIGS. 4. (A) and (B) Stereo representation of a detailed view of CSD: preE-loop of the complex indicated. (C) EMSA using the protein and preEM RNA combination indicated above each row. Each panel represents a titration using the particular mutation at position marked at the left top corner. An asterisk indicates a transversion mutation, and plain numbers indicate transition mutations. Actual sequences for the probes and mutations are shown in main FIG. 4. Sequences are SEQ ID NO NOS 16-18, respectively in order of appearance. (D) Superimposition of previously determined CSD:RNA complexes with Lin28:pre-let-7. Only CSD from Lin28 is shown since all four protein models overlap well (blue cartoon) and RNA backbone is shown in indicated colors.

Specific binding of preE-let-7 with CSD: A detailed analysis of the contacts between the CSD and the preE-let-7 stem-loops suggests that specificity relies on both the sequence and the conformation of the RNA. Most of the direct contacts lie in a ≥9-nucleotide segment that includes the preE-loop (FIG. 4, 11A-B). As the loop wraps around the CSD, the bases project and make a number of π-stacking interactions with aromatic side chains. Complementary to the Velcro-like effects of the hydrophobic interactions, hydrogen bonding and steric exclusion create nucleotide preferences and enhance specificity. From inspection of the binding pocket of each nucleotide, we can imagine an ideal RNA substrate for the CSD of Lin28. To simplify the discussion, the inventors define the middle position of preE-let-7d that docks into the pocket lined by Phe73 and Lys102 as the "center", or position 0. Purines are preferred at positions 0 and −1, near the tip of the loop so that the bulky bases can reach the protein. Position 1, on the other hand, is limited to a pyrimidine, as Lys45 and Asp71 impose steric hindrance. A deeper pocket at position −3 makes a purine more favorable, because a larger ring is necessary to stack over Phe84 (in d and f-1) and also to make favorable contacts with the Lin28 backbone (in all three). The hydrogen bonding networks around −3, −1 and 0 are specific for G, G and A, respectively.

The inventors evaluated the effect of several point mutations in the co-crystallized preEs at positions where specific interactions are observed in the structures (FIG. 4C, 11C). Most of the mutant probes have lower affinity for Lin28 than wild-type. Although Gua is strongly preferred over Ade at positions −3 and −1, substitution of $Ade_0$ with a Gua is not as deleterious. Ade replaces $Gua_{-3}$ in the Lin28:let-7g complex, and as a result some favorable hydrogen bonds are absent in comparison to other structures. Due to the small size of the pocket, a pyrimidine is strongly preferred at position 1. Some of the previously reported mutations of preE-let-7g include a transversion (purine to pyrimidine) at position 0 (Newman et al., 2008) and changes in the preE-stem that disrupt base pairing (Piskounova et al., 2008). While the studies described herein in focused on mouse Lin28a, the observed effects of $preE_M$ point mutations on complex stability are equivalent for human Lin28a and Lin28b (FIG. 11C).

Comparing the structure of Lin28 bound to the divergent preE-let-7g with those of the preE-let-7d and -7f-1 complexes illustrates how the CSD accommodates variability in substrate RNAs. The short preE-loops in let-7d and -f-1 require that base pairs be broken to fit around the CSD. In order to tighten the longer loop in preE-let-7g (FIG. 4B), Arg50 moves in to mimic a base, pairing with $Cyt_{-5}$ and stacking against $Ade_5$. The other extra bases have π-stacking interactions: two with the side chains of Arg122 and Arg123 at the amino-terminal end of the inter-domain linker, and $Ade_2$ and $Cyt_3$ with each other. A closed RNA loop appears to be important to maintain full contact with the CSD, perhaps explaining the more extensive interactions here than in other CSD:RNA complex structures (Frazão et al., 2006, Max et al., 2006, 2007) (FIG. 11D).

Figure 5:
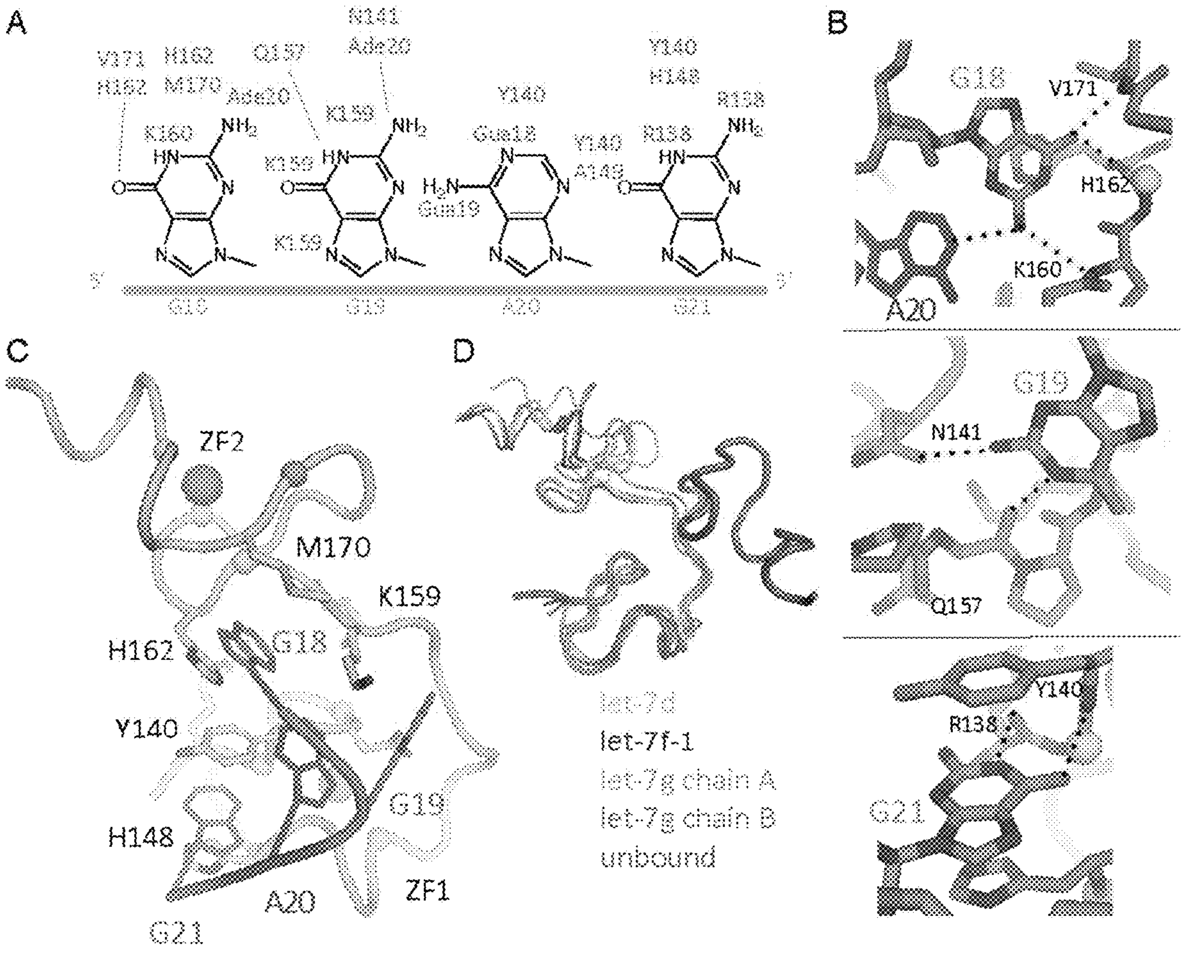
FIG. 5. CCHCx2:RNA interactions. See also FIG. 12. (A) Schematic drawing of GGAG, and atoms making contact are marked with amino acid/nucleotide numbers (green, hydrophobic or γc-stacking; red, H-bond). (B) Close-up view of base interactions. H-bonds are marked with dashed lines. (C) View of GGAG interactions with CCHCx2. Lin28 is represented with grey cartoon, and GGAG are colored by sequence (Green, Gua; Azure, Ade). Zinc (large grey spheres)-coordinating residues are represented with small spheres at Cα positions (yellow, Cys; cyan, His). (D) Comparison of the CCHCx2 region of Lin28 in different states by superimposition of the first CCHC motif (unbound, PDB code=2CQF).
Figure 12:
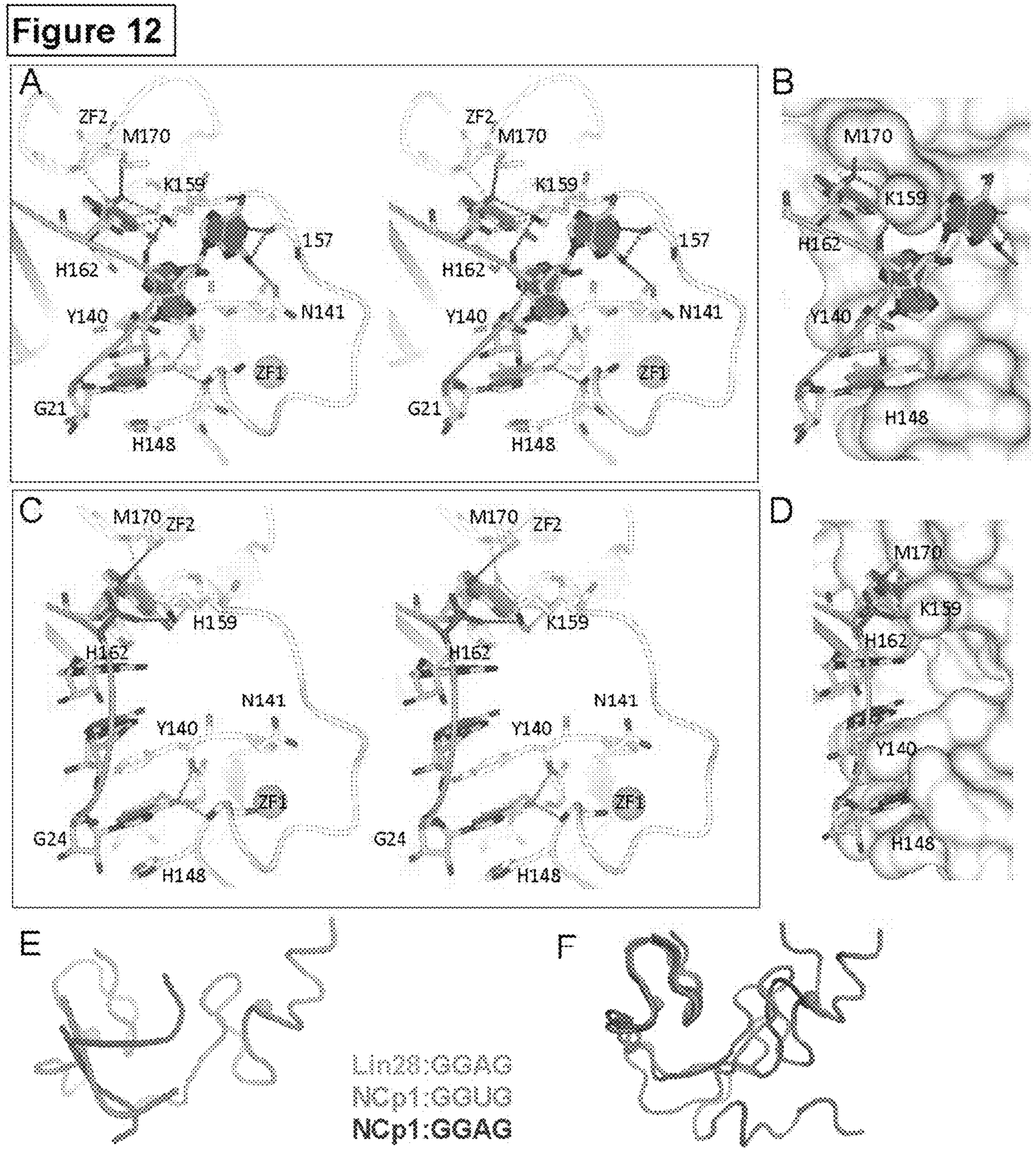
FIG. 12. CCHCx2:RNA interactions, related to FIG. 5. (A) Stereo representation of a detailed view of CCHCx2: GGAG interactions, using Lin28:preE$_M$-let-7d complex structure. This conformation is observed in all copies of preE-let-7d, both copies of preE-let-7f, and chain B of preE-let-7g. (B) Identical orientation as in (A), but protein is shown with surface representation. (C) Same as (A) but for Lin28:preE$_M$-let-7g structure, chain A. (D) Identical orientation as (C), but protein is shown with surface representation. (E) and (F) CCCHCx2 conformations are variable. CCHCx2 from Lin28 (green):preE$_M$-let-7d (orange) complex is compared with NMR structures of HIV NCp1 CCHCx2:RNA complexes by superimposition of the first CCHC. Only RNA backbone is shown in (E) against Lin28, and only protein backbone is shown in (F) for clarity.

Interactions of zinc knuckles with preE-let-7: The CCHC knuckles maximize favorable interactions with a small number of nucleotides by making many contacts with the bases (FIG. 5A-C). The intimate interaction between GGAG and CCHCx2 produces a distinctive kink in the RNA backbone. Most of the protein atoms participating in the extensive hydrogen bonding network lie in relatively rigid regions of the protein, such as adjacent to zinc-coordinating residues or in a proline-rich linker, thereby imposing a specific, rigid conformation on the 3' end of the RNA (FIG. 5C, 12A-B). Ring stacking and hydrophobic interactions with side chains of the CCHCx2 further stabilize the particular conformation by aligning the bases. One of the key residues is Y140, which establishes the kinked conformation by sandwiching between the last two bases (AG) and interacting with H162, which braces the first (G). Although the adenine base does not have as many polar contacts with Lin28, it packs closely against the first Gua and makes a hydrogen bond that assists in bending the RNA backbone. The resulting conformation of the ssRNA resembles that of the so-called "K-turn", which often participates in specific protein-RNA interactions (Klein et al., 2001).

The CCHCx2 regions from all our structures align well with each other, except for slight differences, due to crystal contacts, in one of the two non-crystallographic copies of $preE_M$-let-7g (FIG. 12C-D). When compared with the conformation seen in the solution structure of an isolated Lin28 zinc-knuckle fragment (PDB 2CQF), however, there is a large rearrangement of the inter-knuckle joint in Lin28 (FIG. 5D). Therefore, association of CCHCx2 with GGAG imposes specific conformational constraints on both the RNA and the protein; this reciprocal effect may be functionally important for regulation.

Two NMR structures of CCHC motifs from HIV NCp1 have been determined previously, in which the knuckles bind a tetraloop of sequence GGAG or GGUG in two stem loops (SL2 and SL3) of the ψ-site (Amarasinghe et al., 2000, De Guzman et al., 1998). The conformation of the GGAG motif in complex with Lin28 is very different from its conformation in complex with HIV NCp1, indicating that the conformation we observe is specific to Lin28 (FIG. 12E-F).

Lin28 interactions with full-length pre-let-7: To test their conclusions from the model provided by the crystal structures, and to verify that the truncations and deletions they had made for crystallization did not affect specificity, the inventors generated mutant forms of full-length Lin28 and pre-let-7g. Alteration of the key binding sites of CSD (near position 0) or CCHCx2 (GGAG) in pre-let-7g reduces affinity, consistent with the mutagenesis studies with preE fragments (FIG. 6A, 13A). In addition, mutation of RNA-contacting residues in CSD and CCHCx2 also interferes with complex formation, especially when aromatic side chains are replaced with Ala (FIG. 6B, 13B). We then conducted binding assays using combinations of protein and RNA mutants (FIG. 6C, 3C). The D71 side chain, which is near nucleotide position 1, limits the size of the pocket and restricts it to pyrimidine rings. Presumably due to the additional free space provided by a glycine, a D71G mutant no longer discriminates against a purine at position 1 (FIG. 6C, D71G block).

The bipartite character of the Lin28:let-7 interactions implies that one should observe strong synergy when combining a mutation in one of the two let-7 interaction sites with a mutation in the Lin28 domain that recognizes the other let-7 interaction site. Indeed, a CSD mutation (F73A) has much greater effect on binding with RNA bearing a mutation in the GGAG motif (to GGAU or deletion) than it does on binding with RNA bearing a preE-loop mutation near the CSD binding site (FIG. 6C, F73A block). Similarly, for binding with a mutated CCHCx2 (Y140A), GGAG mutations are not as detrimental as a CSD binding-site mutation (FIG. 6C, Y140A block). The inventors also tested binding of individual domains of Lin28 to various pre-let-7g mutants (FIG. 6C, CSD and CCHCx2 blocks). Neither isolated domain binds to let-7 as specifically or tightly as does full-length Lin28. Nevertheless, RNA mutations at each binding site affect only the affinity of the corresponding domain, consistent with the model presented herein. In summary, the results of all these mutational studies are all consistent with the conclusion that Lin28 binds full-length pre-let-7 in the same way as does the truncated form present in the crystals described herein.

The GGAG motif is conserved among let-7s not only in its sequence but also in its proximal position with respect to the Dicer site in the context of the full pre-let-7 molecule. The last G is 4 bases from the Dicer cleavage site on the 3' strand, and only 2 bases from the position at which complementarity to the mature strand begins. Using previously determined structures of Dicer and the proposed location of the cut site (Du et al., 2008, Macrae et al., 2006), the inventors have modeled how a Lin28:pre-let-7 complex would interact with Dicer (FIG. 13D). Because their binding sites on RNA are close together and because Lin28 bends the RNA backbone, Lin28, especially its CCHCx2, can hinder Dicer directly. To test whether binding of Lin28 with pre-let-7g is sufficient to inhibit Dicer processing, the inventors used different mutants in an in vitro Dicer assay (FIG. 6D). The mutations that disrupt association between Lin28 and pre-let-7 lead to increased Dicer cleavage, compared with wildtype control. The data presented herein are thus consistent with a direct effect of Lin28 on Dicer processing of pre-let-7.

The inventors also tested the effect of the described mutations on in vivo processing of let-7 (FIG. 6E-G). Mutations that affect CSD binding de-repress processing of pri-let-7g only modestly, perhaps because the presence of other cellular factors partially compensate for the affinity change (<10 fold). Altering the CCHCx2:GGAG interaction—by changes in RNA or protein—is more detrimental to Lin28 activity. Levels of mature let-7 in our in vivo assay depend on both complex formation between Lin28 and let-7 precursors and downstream effects of Lin28, such as hindering Drosha and Dicer while recruiting TUTase. The results indicate that although both CSD and CCHCx2 contribute to affinity and specificity for let-7 precursors, the CCHCx2:GGAG interaction is more critical for the effector function of Lin28.

Figure 14:
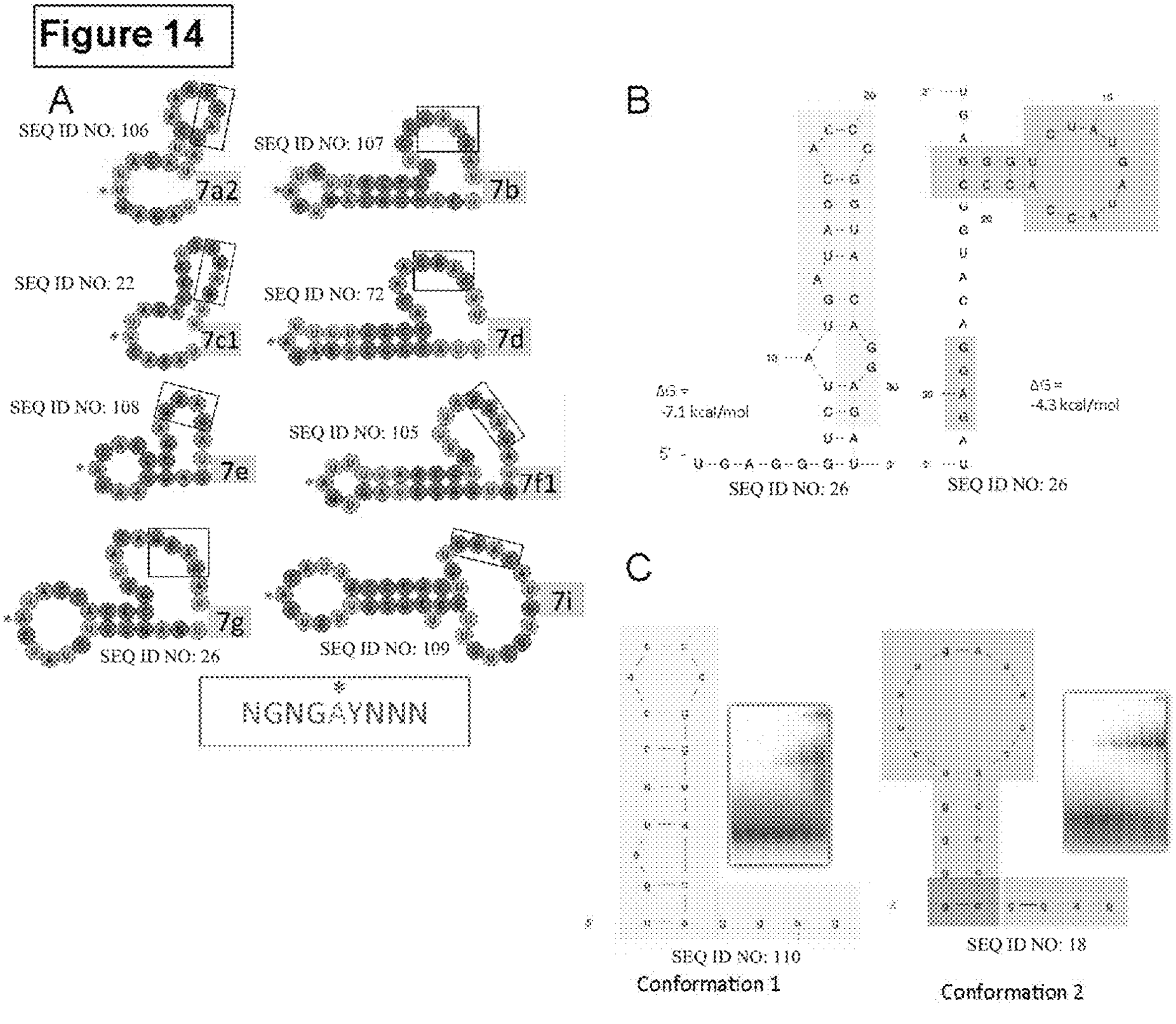
FIG. 14. Structural model suggests how Lin28 would bind to various let-7 family members, related to FIG. 7. (A) Proposed Lin28 binding sites on a selection of mouse preE-let-7s. The entire preE-let-7 sequences are shown, as seen in FIG. 8A. The optimal conformation for binding was chosen among the top 3 structures calculated by mfold. The minimal RNA for CSD binding is shown in red box, with sequence preference (Y=pyrimidine, N=any). The central position in the loop (zero as defined in the text) is marked with an asterisk and the GGAG motif is indicated with boxes outlined in black. Although some CSD binding sites do not exactly match the preferred sequence, our mutagenesis results show that these RNA mutations only slightly reduce affinity to Lin28. Sequences shown are SEQ ID NO: 106, for 7a2; SEQ ID NO: 107, for 7b; SEQ ID NO: 22, for 7c1; SEQ ID NO: 72, for 7d; SEQ ID NO: 108, for 7e; SEQ ID NO: 105, for 7f1; SEQ ID NO: 26, for 7g; and SEQ ID NO: 109, for 7i. (B) Predicted structures of preE-let-7g by mfold as referenced in text. Colored blocks indicate portions used to generate minimal Lin28-binding constructs shown in (C). Sequences shown are SEQ ID NO: 26 (left) and SEQ ID NO: 26 (right). (C) Predicted structures of fragments of preE-let-7g designed for complex formation with Lin28. Two constructs of stem-loop with a 3' tail were designed using the two predicted structures in (A). An extra G-C base pair was added distal to the preE-loop to aid with crystallization. EMSA results using the diagrammed probes in (C) show that conformation 2 construct binds Lin28 with much higher affinity. Sequences shown are SEQ ID NO: 110 (left) and SEQ ID NO: 18 (right).

Deciphering Lin28 specificity: The structural and biochemical studies presented here reveal how Lin28 recognizes let-7 precursors and allow us to postulate how Lin28 might bind diverse pre-let-7s. The inventors have discovered a preferred sequence consensus for CSD binding: NGNGA$_0$YNNN (Y=pyrimidine; N=any base). The sequences and distances between the CSD binding site and the CCHCx2-binding GGAG motif are variable, but the two sites can be identified in many of the preE-let-7 sequences (FIG. 14A). Without wishing to be bound by a theory, in cases where no significant preE-stem structure is predicted (e.g., in let-7a-2 or let-7c-1), the nearby mature region with its stable double-stranded helix can aid in closing the loop around the CSD. Loss of one or a few favorable interactions in other preE-let-7s might not completely exclude the RNAs from binding to Lin28, but rather result in differences in affinity that could affect the sensitivity of particular let-7s to Lin28 regulation in vivo. Indeed, understanding Lin28 specificity from preE-let-7d and preE-let-7f-1 allowed the inventors to crystallize the preE-let-7g complex, which binds to Lin28 in an energetically less stable conformation (FIG. 14B-C).

The sequence of the linker between CSD and CCHCx2 has a strong net positive charge, probably to interact with the negatively charged RNA sugar-phosphate backbone, or to compensate for any unpaired bases, as seen in the case of preE-let-7g complex. Evolutionary conservation of the electrostatic property suggests that the linker does play some role, even though its sequence is not crucial for binding specificity. The length of the linker varies in some organisms, and shorter linkers occur in those with only one copy of let-7 containing a shorter preE sequence. Longer, more flexible linkers might have evolved in higher eukaryotes to recognize longer and divergent let-7 precursors. The preE-let-7g complex structure described herein illustrates how the linker can adapt to different RNA substrates; Arg122 and Arg123 at the amino terminal end of the inter-domain linker stack against extra bases near the ds-ss junction (FIG. 12B).

The GGAG tetranucleotide motif is well conserved among the members of the let-7 family within a particular species. In evolutionarily distant organisms such as worms and fruit flies, however, other sequences (such as GGUG or AUCA) are found in place of GGAG, perhaps due to co-evolution of RNA and protein. Although not included in the crystal structure, the two nucleotides following GGAG are A and U in most let-7 sequences. In the context of full-length molecules, there may be more contacts between the bulge near GGAG and CCHCx2. The importance of the GGAG motif has been explored previously, by introducing a GGAG motif into an unrelated RNA sequence, miR-16, to generate a chimeric pre-miRNA that has gained affinity for Lin28 (Heo et al., 2009). From the binding experiments and structural data, the GGAG motif alone cannot confer robust binding with Lin28, and shifting its position by a base or two relative to the CSD binding site does not affect Lin28 binding significantly. In the case of the chimeric RNA with miR-16, its preE also coincidentally contains a sequence similar to the preferred CSD binding site (UAAGAUUCU vs. NGNGAYNN), at the 5' side of the GGAG motif, explaining why this chimera can bind Lin28. The structural and biochemical data disclosed herein thus provide a molecular explanation for Lin28 specificity, making it possible to investigate further its role in let-7 biogenesis as well as its function in binding various mRNA targets (Jin et al., 2011, Peng et al., 2011, Qiu et al., 2010).

Implications for miRNA regulatory mechanisms: Although Drosha and Dicer are known to cut at opposite ends of the mature miRNA, there are still major questions regarding how they recognize their target and how the cleavage can be regulated. The structures of Lin28:preE-let-7 complexes disclosed herein combined with known structural data for Dicer have allowed the inventor to discover how the Lin28 binding event itself can inhibit processing of pre-let-7 in at least two ways (FIG. 13D). First, Lin28 can act as a "wedge" to melt part of the double-stranded mature region as it bends GGAG and situates itself in a particular conformation on one of the strands. As a result, Dicer can be unable to recognize its substrate properly. Second, given the location of CCHCx2 binding site, the volume of CCHCx2, and the location of its N-terminus from which the interdomain linker would have to traverse to CSD, Lin28 is likely to clash with the Dicer dsRNA binding domains and also mask one of the cleavage sites.

The role of the preE in Drosha processing is less clear, especially since the Drosha cleavage site is at the opposite end of the mature region from preE. Nonetheless, the direct association of Lin28 with the preE shows that the observed effects of both the preE modifications and Lin28 on Drosha activity are probably linked (Michlewski et al., 2008, Zeng, 2003, Zeng and Cullen, 2005, Zeng et al., 2005, Zhang and Zeng, 2010). Other small RNA-binding proteins such as hnRNP-A1 and KSRP have been proposed to modify Drosha processing by binding to the preE region (Michlewski and Caceres, 2010, Michlewski et al., 2008). Rather than being a mere by-product of miRNA processing, preE is clearly a critical handle for regulatory factors such as Lin28.

The mutagenesis studies disclosed herein indicate that the GGAG:CCHCx2 region has an important functional role in regulating let-7, in addition to contributing to the specificity and tightness of complex formation. The in vitro binding results show that the observed strong effect of mutations in the CCHCx2:let-7 interface cannot be attributed to the overall affinity of the molecules alone. As the GGAG motif is closer to the mature sequence, mutations that lead to lower occupancy at this site—regardless of association of CSD with preE—can be more directly linked to hindrance of processing enzymes. Moreover, the specific conformation of CCHCx2:GGAG induced by complex formation, as observed in our crystals, is probably important for recruiting downstream factor(s) such as TUTase. The critical role of Y140 of CCHCx2 in determining the RNA conformation is described in Results, and a uracil base (in GGAU mutant) would not be large enough to stack against Y140 efficiently in the observed conformation. Transition mutations in GGAG sequence might also result in slightly different conformations, without greatly reducing complex formation. Some of these mutations (to GAGG or AAGG) maintain their affinity for Lin28, but can obliterate uridylation by TUTase (Heo et al., 2009). That is, the CSD provides a larger contact and contributes more strongly than CCHxCx2 to let-7 affinity, but the latter domain has additional effector functions.

Figure 7:
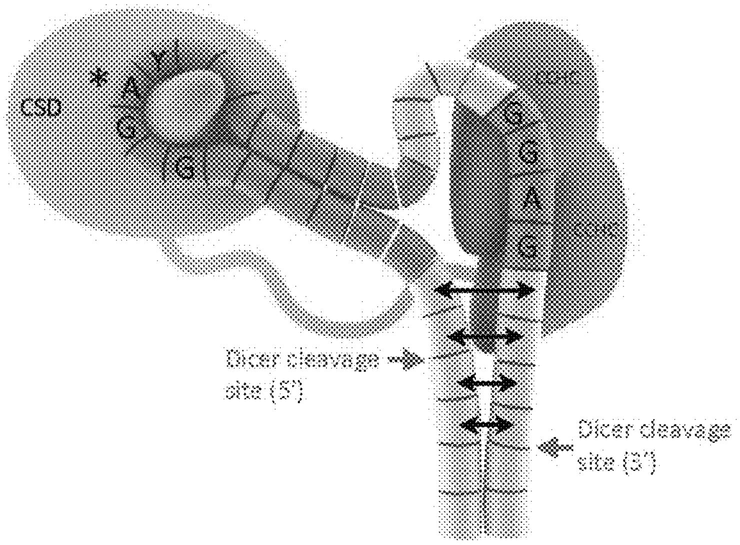
FIG. 7. Schematic model for Lin28 domains binding to two distinct regions of preE-let-7 (f-1 was used for the model figure). For Lin28: Blue, CSD; Green, CCHCx2; Blue-green loop, protein linker. For pre-let-7 depicted as array of cylinders: Yellow, mature region; Orange, bases included in the crystallization construct; Grey, parts of preE not included in the crystal. Potential partial melting of dsRNA near Dicer sites is represented with double-headed arrows; it is uncertain how far the effect would carry. From structural models, interactions with other preE-let-7 sequences can be postulated as shown in FIG. 14.

The structures of the three Lin28:preE-let-7 complexes the inventors have determined show a bipartite interaction of Lin28 with its let-7 family partners (FIG. 7). The CSD inserts into the loop at one end of the central stem-loop structure in preE-let-7, and the CCHCx2 module recognizes a GGAG motif at the other end. The linker between CSD and CCHCx2 is flexible, to accommodate variable sequences and lengths among Lin28-regulated let-7 family members without compromising affinity or specificity. This molecular organization explains several conserved features of preE-let-7s: first, a minimum loop length of 9-nucleotides, with a preferred sequence of NGNGAYNNN; second, a stem-like structure that closes the loop into a circle; and third, a GGAG motif close to the 3' end of the preE. The model provided by our crystal structures provides a mechanistic explanation for the inhibitory effect of Lin28 on miRNA processing by Dicer; it further suggests that the CCHCx2:GGAG part of the complex directly influences downstream factor(s) important for let-7 regulation. These structural details will be useful for developing therapies that target the Lin28:pre-let-7 complex and its effects on let-7 processing.

Thus, presented herein are high-resolution crystal structures of mouse Lin28a in complex with three preE constructs of let-7d, let-7f-1, and let-7g. These structures provide a direct view of a protein interacting with the terminal loop region of a miRNA. The inventors have discovered sequence-specific interactions between Lin28 and let-7 precursors that give direct structural evidence for the role of preEs in miRNA regulation. The Lin28 CSD and the CCHC "zinc knuckles" make extensive contacts with the preE elements in two distinct regions. Described herein also are NMR studies and biochemical assays showing that the linker between the CSD and CCHCx2 regions introduces flexibility to accommodate variable preE sequences and lengths while preserving the joint contribution of the two interaction sites to overall affinity. The data show that both the terminal and linker regions outside of the folded domains are not essential for blocking let-7 in vivo. Studies with mutagenesis of preE fragments and full-length pre-miRNA show the specificity of Lin28 and how Lin28 recognizes other let-7s. Complex formation induces in both Lin28 and preE-let-7 a specific conformation that can affect recognition by downstream factors such as Drosha, Dicer and TUTase, and changes in the CCHCx2 region are particularly detrimental to Lin28 activity in vivo.

REFERENCES

1. Amarasinghe, G. K., De Guzman, R. N., Turner, R. B., Chancellor, K. J., Wu, Z. R., and Summers, M. F. (2000). NMR structure of the HIV-1 nucleocapsid protein bound to stem-loop SL2 of the psi-RNA packaging signal. Implications for genome recognition. Journal of Molecular Biology 301, 491-511.
2. Büssing, I., Slack, F. J., and Grosshans, H. (2008). let-7 microRNAs in development, stem cells and cancer. Trends in molecular medicine 14, 400-409.
3. Davis-Dusenbery, B. N., and Hata, A. (2010). Mechanisms of control of microRNA biogenesis. Journal of biochemistry 148, 381-392.
4. De Guzman, R. N., Wu, Z. R., Stalling, C. C., Pappalardo, L., Borer, P. N., and Summers, M. F. (1998). Structure of the HIV-1 nucleocapsid protein bound to the SL3 psi-RNA recognition element. Science (New York, N.Y.) 279, 384-388.
5. De, N., and Macrae, I. J. (2011). Purification and Assembly of Human Argonaute, Dicer, and TRBP Complexes. Methods in molecular biology (Clifton, N.J.) 725, 107-119.

6. Du, Z., Lee, J. K., Tjhen, R., Stroud, R. M., and James, T. L. (2008). Structural and biochemical insights into the dicing mechanism of mouse Dicer: a conserved lysine is critical for dsRNA cleavage. Proceedings Of The National Academy Of Sciences Of The United States Of America 105, 2391-2396.
7. Frazão, C., McVey, C. E., Amblar, M., Barbas, A., Vonrhein, C., Arraiano, C. M., and Carrondo, M. A. (2006). Unravelling the dynamics of RNA degradation by ribonuclease II and its RNA-bound complex. Nature 443, 110-114.
8. Guo, Y., Chen, Y., Ito, H., Watanabe, A., Ge, X., Kodama, T., and Aburatani, H. (2006). Identification and characterization of lin-28 homolog B (LIN28B) in human hepatocellular carcinoma. Gene 384, 51-61.
9. Hagan, J. P., Piskounova, E., and Gregory, R. I. (2009). Lin28 recruits the TUTase Zcchcll to inhibit let-7 maturation in mouse embryonic stem cells. Nature Structural & Molecular Biology 16, 1021-1025.
10. Han, J., Lee, Y., Yeom, K.-H., Nam, J.-W., Heo, I., Rhee, J.-K., Sohn, S. Y., Cho, Y., Zhang, B.-T., and Kim, V. N. (2006). Molecular basis for the recognition of primary microRNAs by the Drosha-DGCR8 complex. Cell 125, 887-901.
11. Heo, I., Joo, C., Cho, J., Ha, M., Han, J., and Kim, V. N. (2008). Lin28 mediates the terminal uridylation of let-7 precursor MicroRNA. Molecular Cell 32, 276-284.
12. Heo, I., Joo, C., Kim, Y.-K., Ha, M., Yoon, M.-J., Cho, J., Yeom, K.-H., Han, J., and Kim, V. N. (2009). TUT4 in concert with Lin28 suppresses microRNA biogenesis through pre-microRNA uridylation. Cell 138, 696-708.
13. Iliopoulos, D., Hirsch, H. A., and Struhl, K. (2009). An epigenetic switch involving NF-kappaB, Lin28, Let-7 MicroRNA, and IL6 links inflammation to cell transformation. Cell 139, 693-706.
14. Jin, J., Jing, W., Lei, X.-X., Feng, C., Peng, S., Boris-Lawrie, K., and Huang, Y. (2011). Evidence that Lin28 stimulates translation by recruiting RNA helicase A to polysomes. Nucleic Acids Research 39, 3724-3734.
15. Kim, V. N., Han, J., and Siomi, M. C. (2009). Biogenesis of small RNAs in animals. Nature reviews Molecular cell biology 10, 126-139.
16. King, C. E., Cuatrecasas, M., Castells, A., Sepulveda, A. R., Lee, J.-S., and Rustgi, A. K. (2011). LIN28B promotes colon cancer progression and metastasis. Cancer research 71, 4260-4268.
17. Klein, D. J., Schmeing, T. M., Moore, P. B., and Steitz, T. A. (2001). The kink-turn: a new RNA secondary structure motif The EMBO Journal 20, 4214-4221.
18. Krol, J., Loedige, I., and Filipowicz, W. (2010). The widespread regulation of microRNA biogenesis, function and decay. Nature reviews Genetics 11, 597-610.
19. Landthaler, M., Gaidatzis, D., Rothballer, A., Chen, P. Y., Soll, S. J., Dinic, L., Ojo, T., Hafner, M., Zavolan, M., and Tuschl, T. (2008). Molecular characterization of human Argonaute-containing ribonucleoprotein complexes and their bound target mRNAs. RNA (New York, N.Y.) 14, 2580-2596.
20. Lehrbach, N. J., Armisen, J., Lightfoot, H. L., Murfitt, K. J., Bugaut, A., Balasubramanian, S., and Miska, E. A. (2009). LIN-28 and the poly(U) polymerase PUP-2 regulate let-7 microRNA processing in *Caenorhabditis elegans*. Nature Structural & Molecular Biology 16, 1016-1020.
21. Lettre, G., Jackson, A. U., Gieger, C., Schumacher, F. R., Berndt, S. I., Sanna, S., Eyheramendy, S., Voight, B. F., Butler, J. L., Guiducci, C., et al. (2008). Identification often loci associated with height highlights new biological pathways in human growth. Nature genetics 40, 584.
22. Lu, L., Katsaros, D., Shaverdashvili, K., Qian, B., Wu, Y., de la Longrais, I. A. R., Preti, M., Menato, G., and Yu, H. (2009). Pluripotent factor lin-28 and its homologue lin-28b in epithelial ovarian cancer and their associations with disease outcomes and expression of let-7a and IGF-II. European journal of cancer (Oxford, England: 1990) 45, 2212-2218.
23. Macrae, I. J., Zhou, K., Li, F., Repic, A., Brooks, A. N., Cande, W. Z., Adams, P. D., and Doudna, J. A. (2006). Structural basis for double-stranded RNA processing by Dicer. Science (New York, N.Y.) 311, 195-198.
24. Markham, N. R., and Zuker, M. (2005). DINAMelt web server for nucleic acid melting prediction. Nucleic Acids Research 33, W577-581.
25. Max, K. E. A., Zeeb, M., Bienert, R., Balbach, J., and Heinemann, U. (2006). T-rich DNA single strands bind to a preformed site on the bacterial cold shock protein Bs-CspB. Journal of Molecular Biology 360, 702-714.
26. Max, K. E. A., Zeeb, M., Bienert, R., Balbach, J., and Heinemann, U. (2007). Common mode of DNA binding to cold shock domains. Crystal structure of hexathymidine bound to the domain-swapped form of a major cold shock protein from Bacillus caldolyticus. The FEBS journal 274, 1265-1279.
27. Michlewski, G., and Caceres, J. F. (2010). Antagonistic role of hnRNP A1 and KSRP in the regulation of let-7a biogenesis. Nature Structural & Molecular Biology 17, 1011-1018.
28. Michlewski, G., Guil, S., Semple, C. A., and Cáceres, J. F. (2008). Posttranscriptional regulation of miRNAs harboring conserved terminal loops. Molecular Cell 32, 383-393.
29. Moss, E. G., Lee, R. C., and Ambros, V. (1997). The cold shock domain protein LIN-28 controls developmental timing in *C. elegans* and is regulated by the lin-4 RNA. Cell 88, 637-646.
30. Newman, M. A., Thomson, J. M., and Hammond, S. M. (2008). Lin-28 interaction with the Let-7 precursor loop mediates regulated microRNA processing. RNA (New York, N.Y.) 14, 1539-1549.
31. Ong, K. K., Elks, C. E., Li, S., Zhao, J. H., Luan, J. a. a., Andersen, L. B., Bingham, S. A., Brage, S., Smith, G. D., Ekelund, U., et al. (2009). Genetic variation in LIN28B is associated with the timing of puberty. Nature genetics 41, 729.
32. Peng, S., Chen, L.-L., Lei, X.-X., Yang, L., Lin, H., Carmichael, G. G., and Huang, Y. (2011). Genome-wide studies reveal that lin28 enhances the translation of genes important for growth and survival of human embryonic stem cells. STEM CELLS 29, 496-504.
33. Peng, S., Maihle, N. J., and Huang, Y. (2010). Pluripotency factors Lin28 and Oct4 identify a sub-population of stem cell-like cells in ovarian cancer. Oncogene 29, 2153-2159.
34. Permuth-Wey, J., Kim, D., Tsai, Y.-Y., Lin, H.-Y., Chen, Y. A., Barnholtz-Sloan, J., Birrer, M. J., Bloom, G., Chanock, S. J., Chen, Z., et al. (2011). LIN28B polymorphisms influence susceptibility to epithelial ovarian cancer. Cancer research 71, 3896-3903.
35. Perry, J. R. B., Stolk, L., Franceschini, N., Lunetta, K. L., Zhai, G., Mcardle, P. F., Smith, A. V., Aspelund, T., Bandinelli, S., Boerwinkle, E., et al. (2009). Meta-analysis of genome-wide association data identifies two loci influencing age at menarche. Nature genetics 41, 648.

36. Piskounova, E., Viswanathan, S. R., Janas, M., Lapierre, R. J., Daley, G. Q., Sliz, P., and Gregory, R. I. (2008). Determinants of microRNA processing inhibition by the developmentally regulated RNA-binding protein Lin28. The Journal of biological chemistry 283, 21310-21314.

37. Qiu, C., Ma, Y., Wang, J., Peng, S., and Huang, Y. (2010). Lin28-mediated post-transcriptional regulation of Oct4 expression in human embryonic stem cells. Nucleic Acids Research 38, 1240-1248.

38. Rybak, A., Fuchs, H., Smirnova, L., Brandt, C., Pohl, E. E., Nitsch, R., and Wulczyn, F. G. (2008). A feedback loop comprising lin-28 and let-7 controls pre-let-7 maturation during neural stem-cell commitment. Nature Cell Biology 10, 987-993.

39. Siomi, H., and Siomi, M. C. (2010). Posttranscriptional regulation of microRNA biogenesis in animals. Molecular Cell 38, 323-332.

40. Sulem, P., Gudbjartsson, D. F., Rafnar, T., Holm, H., Olafsdottir, E. J., Olafsdottir, G. H., Jonsson, T., Alexandersen, P., Feenstra, B., Boyd, H. A., et al. (2009). Genome-wide association study identifies sequence variants on 6q21 associated with age at menarche. Nature genetics 41, 734.

41. Viswanathan, S. R., and Daley, G. Q. (2010). Lin28: A microRNA regulator with a macro role. Cell 140, 445-449.

42. Viswanathan, S. R., Daley, G. Q., and Gregory, R. I. (2008). Selective blockade of microRNA processing by Lin28. Science (New York, N.Y.) 320, 97-100.

43. Viswanathan, S. R., Powers, J. T., Einhorn, W., Hoshida, Y., Ng, T. L., Toffanin, S., O' Sullivan, M., Lu, J., Phillips, L. A., Lockhart, V. L., et al. (2009). Lin28 promotes transformation and is associated with advanced human malignancies. Nature genetics 41, 843-848.

44. Walker, S. C., Avis, J. M., and Conn, G. L. (2003). General plasmids for producing RNA in vitro transcripts with homogeneous ends. Nucleic Acids Research 31, e82.

45. Wan, G., En Lim, Q., and Too, H. P. (2010). High-performance quantification of mature microRNAs by real-time RT-PCR using deoxyuridine-incorporated oligonucleotides and hemi-nested primers. RNA (New York, N.Y.) 16, 1436-1445.

46. Yang, D. H., and Moss, E. G. (2003). Temporally regulated expression of Lin-28 in diverse tissues of the developing mouse. Gene expression patterns: GEP 3, 719-726.

47. Yu, F., Yao, H., Zhu, P., Zhang, X., Pan, Q., Gong, C., Huang, Y., Hu, X., Su, F., Lieberman, J., et al. (2007a). Let-7 regulates self-renewal and tumorigenicity of breast cancer cells. Cell 131, 1109-1123.

48. Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007b). Induced pluripotent stem cell lines derived from human somatic cells. Science (New York, N.Y.) 318, 1917-1920.

49. Zeng, Y. (2003). Sequence requirements for micro RNA processing and function in human cells. RNA (New York, N.Y.) 9, 112-123.

50. Zeng, Y., and Cullen, B. R. (2005). Efficient processing of primary microRNA hairpins by Drosha requires flanking nonstructured RNA sequences. The Journal of biological chemistry 280, 27595-27603.

51. Zeng, Y., Yi, R., and Cullen, B. R. (2005). Recognition and cleavage of primary microRNA precursors by the nuclear processing enzyme Drosha. The EMBO Journal 24, 138-148.

52. Zhang, X., and Zeng, Y. (2010). The terminal loop region controls microRNA processing by Drosha and Dicer. Nucleic Acids Research 38, 7689-7697.

53. Zhu, H., Shah, S., Shyh-Chang, N., Shinoda, G., Einhorn, W. S., Viswanathan, S. R., Takeuchi, A., Grasemann, C., Rinn, J. L., Lopez, M. F., et al. (2010). Lin28a transgenic mice manifest size and puberty phenotypes identified in human genetic association studies. Nature genetics 42, 626-630.

54. Adams, P. D., Afonine, P. V., Bunkoczi, G., Chen, V. B., Davis, I. W., Echols, N., Headd, J. J., Hung, L.-W., Kapral, G. J., Grosse-Kunstleve, R. W., et al. (2010). PHENIX: a comprehensive Python-based system for macromolecular structure solution. Acta crystallographica Section D, Biological crystallography 66, 213-221.

55. Bricogne, G., Blanc, E., Brandl, M., Flensburg, C., Keller, P., Paciorek, W., Roversi, P., Sharff, A., Smart, O. S., Vonrhein, C., et al. (2011). BUSTER version 2.11.1 (Cambridge, United Kingdom, Global Phasing Ltd).

56. Delaglio, F., Grzesiek, S., Vuister, G. W., Zhu, G., Pfeifer, J., and Bax, A. (1995). NMRPipe: a multidimensional spectral processing system based on UNIX pipes. Journal of biomolecular NMR 6, 277-293.

57. Emsley, P., and Cowtan, K. (2004). Coot: model-building tools for molecular graphics. Acta crystallographica Section D, Biological crystallography 60, 2126-2132.

58. Evans, P. (2006). Scaling and assessment of data quality. Acta crystallographica Section D, Biological crystallography 62, 72-82.

59. Kabsch, W. (2010). XDS. Acta crystallographica Section D, Biological crystallography 66, 125-132.

60. Kay, L. E., Torchia, D. A., and Bax, A. (1989). Backbone dynamics of proteins as studied by 15N inverse detected heteronuclear NMR spectroscopy: application to staphylococcal nuclease. Biochemistry 28, 8972-8979.

61. McCoy, A. J., Grosse-Kunstleve, R. W., Adams, P. D., Winn, M. D., Storoni, L. C., and Read, R. J. (2007). Phaser crystallographic software. Journal of applied crystallography 40, 658-674.

62. Schneider, T. R., and Sheldrick, G. M. (2002). Substructure solution with SHELXD. Acta crystallographica Section D, Biological crystallography 58, 1772-1779.

63. Schwarzinger, S., Kroon, G. J., Foss, T. R., Chung, J., Wright, P. E., and Dyson, H. J. (2001). Sequence-dependent correction of random coil NMR chemical shifts. Journal of the American Chemical Society 123, 2970-2978.

64. Terwilliger, T. C., Adams, P. D., Read, R. J., McCoy, A. J., Moriarty, N. W., Grosse-Kunstleve, R. W., Afonine, P. V., Zwart, P. H., and Hung, L.-W. (2009). Decision-making in structure solution using Bayesian estimates of map quality: the PHENIX AutoSol wizard. Acta crystallographica Section D, Biological crystallography 65, 582-601.

65. Vonrhein, C., Flensburg, C., Keller, P., Sharff, A., Smart, O., Paciorek, W., Womack, T., and Bricogne, G. (2011). Data processing and analysis with the autoPROC toolbox. Acta crystallographica Section D, Biological crystallography 67, 293-302.

66. Voss, N. R., and Gerstein, M. (2005). Calculation of standard atomic volumes for RNA and comparison with proteins: RNA is packed more tightly. Journal of Molecular Biology 346, 477-492.

67. Vranken, W. F., Boucher, W., Stevens, T. J., Fogh, R. H., Pajon, A., Llinas, M., Ulrich, E. L., Markley, J. L., Ionides, J., and Laue, E. D. (2005). The CCPN data model for NMR spectroscopy: development of a software pipeline. Proteins 59, 687-696.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

LENGTHY TABLES

The patent application contains three (3) lengthy Tables; Table 1, Table 2, and Table 3. A copy of the Tables (Table 1, Table 2, and Table 3) are available in electronic form from the USPTO web site. An electronic copy of the table will also be available from the USPTO upon request and payment of the fee set forth in 37 CFR 1.19(b)(3).

What is claimed is:

1. A polypeptide comprising amino acids 31-187 of a wild-type Lin28 polypeptide and wherein the polypeptide comprises a deletion in the amino acid sequence connecting the cold shock domain (CSD) and the first CCHC domain of the wild-type Lin28 polypeptide.

2. The polypeptide of claim 1, wherein the polypeptide comprises a deletion of at least five amino acids in the amino acid sequence connecting the CSD and the first CCHC domain of the wild-type Lin28 polypeptide.

3. The polypeptide of claim 1, wherein the polypeptide comprises a deletion between amino acid positions 121 to 138 of the wild-type Lin28 polypeptide.

4. The polypeptide of claim 3, wherein the polypeptide comprises a deletion of at least five amino acids between positions 121 to 138 of the wild-type Lin28 polypeptide.

5. The polypeptide of claim 4, wherein the polypeptide comprises a deletion of amino acids 127 to 135 of the wild-type Lin28 polypeptide.

6. The polypeptide of claim 4, wherein the polypeptide comprises a deletion of amino acids 121 to 135 of the wild-type Lin28 polypeptide.

7. The polypeptide of claim 1, wherein the polypeptide is less than 200 amino acids in length.

8. The polypeptide of claim 1, wherein the polypeptide comprises at least one modification.

9. The polypeptide of claim 8, wherein the modification is selected from the group consisting of a non-natural amino acid, a D-amino acid, a p amino acid, a chemically modified amino acid, a modified amide linkage, a tag amino acid sequence, and any combinations thereof.

10. The polypeptide of claim 1, wherein the polypeptide is complexed with a divalent cation.

11. The polypeptide of claim 10, wherein the divalent cation is selected from the group consisting of zinc, cobalt, nickel, cadmium, magnesium, and manganese cations.

12. The polypeptide of claim 11, wherein the divalent cation is $Zn^{2+}$.

13. The polypeptide of claim 1, wherein the polypeptide is complexed with a nucleic acid.

14. The polypeptide of claim 13, wherein the nucleic acid comprises the nucleotide sequence 5'-$N^1N^2N^3N^4N^5N^6N^7N^8N^9$-X-GGAG-3', wherein $N^2$, $N^4$, and $N^5$ are independently a purine; $N^6$ is a pyrimidine; $N^1$, $N^3$, $N^7$, $N^8$, and $N^9$ are independently any nucleotide; and X is a nucleotide sequence of from 0 to 100 nucleotides.

15. The polypeptide of claim 1, wherein the wild-type Lin28 polypeptide is a Lin28A or Lin28B polypeptide.

16. The polypeptide of claim 1, wherein the wild-type Lin28 polypeptide is a human Lin28 polypeptide.

17. A method of inhibiting miRNA processing of a pri-miRNA to a mature miRNA in a cell, the method comprising contacting a cell with a polypeptide of claim 1.

18. A screening assay for determining an inhibitor of Lin28 activity, the method comprising contacting a polypeptide of claim 1 with a test compound and selecting the compound that increases the level of mature let-7 miRNA relative to a control.

19. The method of claim 18, wherein the test compound has a molecular weight of less than 5000 Daltons (5 kD).

20. The method of claim 18, wherein the method is a high-throughput screening method.

* * * * *

SEQUENCE LISTING

```
<160> NUMBER OF SEQ ID NOS: 121

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met His His His His His His Glu Asn Leu Tyr Phe Gln
1               5                   10


<210> SEQ ID NO 2
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His His His His His His Glu Asn Leu Tyr Phe Gln Gly Ser Gly
1               5                   10                  15

Ala Ala Glu Lys Ala Pro Glu Glu Ala Pro Pro Asp Ala Ala Arg Ala
            20                  25                  30

Ala Asp Glu Pro Gln Leu Leu His Gly Ala Gly Ile Cys Lys Trp Phe
        35                  40                  45

Asn Val Arg Met Gly Phe Gly Phe Leu Ser Met Thr Ala Arg Ala Gly
    50                  55                  60

Val Ala Leu Asp Pro Pro Val Asp Val Phe Val His Gln Ser Lys Leu
65                  70                  75                  80

His Met Glu Gly Phe Arg Ser Leu Lys Glu Gly Glu Ala Val Glu Phe
                85                  90                  95

Thr Phe Lys Lys Ser Ala Lys Gly Leu Glu Ser Ile Arg Val Thr Gly
            100                 105                 110

Pro Gly Gly Val Phe Cys Ile Gly Ser Glu Arg Arg Pro Lys Gly Lys
        115                 120                 125

Asn Met Gln Lys Arg Arg Ser Lys Gly Asp Arg Cys Tyr Asn Cys Gly
    130                 135                 140

Gly Leu Asp His His Ala Lys Glu Cys Lys Leu Pro Pro Gln Pro Lys
145                 150                 155                 160

Lys Cys His Phe Cys Gln Ser Ile Asn His Met Val Ala Ser Cys Pro
                165                 170                 175

Leu Lys Ala Gln Gln Gly Pro Ser Ser
            180                 185
```

-continued

```
<210> SEQ ID NO 3
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His His His His His His Glu Asn Leu Tyr Phe Gln Gly Ser Gly
1               5                   10                  15

Ala Ala Asp Glu Pro Gln Leu Leu His Gly Ala Gly Ile Cys Lys Trp
            20                  25                  30

Phe Asn Val Arg Met Gly Phe Gly Phe Leu Ser Met Thr Ala Arg Ala
        35                  40                  45

Gly Val Ala Leu Asp Pro Pro Val Asp Val Phe Val His Gln Ser Lys
    50                  55                  60

Leu His Met Glu Gly Phe Arg Ser Leu Lys Glu Gly Glu Ala Val Glu
65                  70                  75                  80

Phe Thr Phe Lys Lys Ser Ala Lys Gly Leu Glu Ser Ile Arg Val Thr
                85                  90                  95

Gly Pro Gly Gly Val Phe Cys Ile Gly Ser Glu Arg Arg Pro Lys Gly
            100                 105                 110

Gly Asp Arg Cys Tyr Asn Cys Gly Gly Leu Asp His His Ala Lys Glu
        115                 120                 125

Cys Lys Leu Pro Pro Gln Pro Lys Lys Cys His Phe Cys Gln Ser Ile
    130                 135                 140

Asn His Met Val Ala Ser Cys Pro Leu Lys Ala Gln Gln Gly Pro Ser
145                 150                 155                 160

Ser Gln Gly Lys


<210> SEQ ID NO 4
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met His His His His His His Glu Asn Leu Tyr Phe Gln Gly Ser Gly
1               5                   10                  15

Glu Glu Pro Glu Lys Leu Pro Gly Leu Ala Glu Asp Glu Pro Gln Val
            20                  25                  30

Leu His Gly Thr Gly His Cys Lys Trp Phe Asn Val Arg Met Gly Phe
        35                  40                  45

Gly Phe Ile Ser Met Ile Ser Arg Glu Gly Asn Pro Leu Asp Ile Pro
    50                  55                  60

Val Asp Val Phe Val His Gln Ser Lys Leu Phe Met Glu Gly Phe Arg
65                  70                  75                  80

Ser Leu Lys Glu Gly Glu Pro Val Glu Phe Thr Phe Lys Lys Ser Pro
                85                  90                  95

Lys Gly Leu Glu Ser Ile Arg Val Thr Gly Pro Gly Gly Ser Pro Cys
            100                 105                 110

Leu Gly Ser Glu Arg Arg Pro Lys Gly Lys Thr Leu Gln Lys Arg Lys
        115                 120                 125

Pro Lys Gly Asp Arg Trp Arg Arg Gln Asp Leu Leu Met Asp Gln Met
    130                 135                 140
```

```
Trp Thr Val Arg Glu Glu Glu Ser Arg Met Ile Pro Arg Cys Tyr Asn
145                 150                 155                 160

Cys Gly Gly Leu Asp His His Ala Lys Glu Cys Ser Leu Pro Pro Gln
                165                 170                 175

Pro Lys Lys Cys His Tyr Cys Gln Ser Ile Met His Met Val Ala Asn
            180                 185                 190

Cys Pro His Lys Leu Ala Ala Gln Leu Pro Ala Ser Ser
        195                 200                 205


<210> SEQ ID NO 5
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met His His His His His His Glu Asn Leu Tyr Phe Gln Gly Ser Gly
1               5                   10                  15

Ala Ala Glu Glu Ala Pro Glu Glu Ala Pro Glu Asp Ala Ala Arg Ala
            20                  25                  30

Ala Asp Glu Pro Gln Leu Leu His Gly Ala Gly Ile Cys Lys Trp Phe
        35                  40                  45

Asn Val Arg Met Gly Phe Gly Phe Leu Ser Met Thr Ala Arg Ala Gly
    50                  55                  60

Val Ala Leu Asp Pro Pro Val Asp Val Phe Val His Gln Ser Lys Leu
65                  70                  75                  80

His Met Glu Gly Phe Arg Ser Leu Lys Glu Gly Glu Ala Val Glu Phe
                85                  90                  95

Thr Phe Lys Lys Ser Ala Lys Gly Leu Glu Ser Ile Arg Val Thr Gly
            100                 105                 110

Pro Gly Gly Val Phe Cys Ile Gly Ser Glu Arg Arg Pro Lys Gly Lys
        115                 120                 125

Ser Met Gln Lys Arg Arg Ser Lys Gly Asp Arg Cys Tyr Asn Cys Gly
    130                 135                 140

Gly Leu Asp His His Ala Lys Glu Cys Lys Leu Pro Pro Gln Pro Lys
145                 150                 155                 160

Lys Cys His Phe Cys Gln Ser Ile Ser His Met Val Ala Ser Cys Pro
                165                 170                 175

Leu Lys Ala Gln Gln Gly Pro Ser Ala Gln Gly Lys
            180                 185


<210> SEQ ID NO 6
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met His His His His His His Glu Asn Leu Tyr Phe Gln Gly Ser Gly
1               5                   10                  15

Ala Ala Asp Glu Pro Gln Leu Leu His Gly Ala Gly Ile Cys Lys Trp
            20                  25                  30

Phe Asn Val Arg Met Gly Phe Gly Phe Leu Ser Met Thr Ala Arg Ala
        35                  40                  45
```

```
Gly Val Ala Leu Asp Pro Pro Val Asp Val Phe Val His Gln Ser Lys
    50                  55                  60

Leu His Met Glu Gly Phe Arg Ser Leu Lys Glu Gly Glu Ala Val Glu
65                  70                  75                  80

Phe Thr Phe Lys Lys Ser Ala Lys Gly Leu Glu Ser Ile Arg Val Thr
                85                  90                  95

Gly Pro Gly Gly Val Phe Cys Ile Gly Ser Glu Arg Arg Pro Lys Gly
            100                 105                 110

Gly Asp Arg Cys Tyr Asn Cys Gly Gly Leu Asp His His Ala Lys Glu
        115                 120                 125

Cys Lys Leu Pro Pro Gln Pro Lys Lys Cys His Phe Cys Gln Ser Ile
    130                 135                 140

Ser His Met Val Ala Ser Cys Pro Leu Lys Ala Gln Gln Gly Pro Ser
145                 150                 155                 160

Ala Gln Gly Lys


<210> SEQ ID NO 7
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met His His His His His His Glu Asn Leu Tyr Phe Gln Gly Ser Gly
1               5                   10                  15

Glu Glu Pro Gly Lys Leu Pro Glu Pro Ala Glu Glu Glu Ser Gln Val
            20                  25                  30

Leu Arg Gly Thr Gly His Cys Lys Trp Phe Asn Val Arg Met Gly Phe
        35                  40                  45

Gly Phe Ile Ser Met Ile Asn Arg Glu Gly Ser Pro Leu Asp Ile Pro
    50                  55                  60

Val Asp Val Phe Val His Gln Ser Lys Leu Phe Met Glu Gly Phe Arg
65                  70                  75                  80

Ser Leu Lys Glu Gly Glu Pro Val Glu Phe Thr Phe Lys Lys Ser Ser
                85                  90                  95

Lys Gly Leu Glu Ser Ile Arg Val Thr Gly Pro Gly Gly Ser Pro Cys
            100                 105                 110

Leu Gly Ser Glu Arg Arg Pro Lys Gly Lys Thr Leu Gln Lys Arg Lys
        115                 120                 125

Pro Lys Gly Asp Arg Cys Tyr Asn Cys Gly Gly Leu Asp His His Ala
    130                 135                 140

Lys Glu Cys Ser Leu Pro Pro Gln Pro Lys Lys Cys His Tyr Cys Gln
145                 150                 155                 160

Ser Ile Met His Met Val Ala Asn Cys Pro His Lys Asn Val Ala Gln
                165                 170                 175

Pro Pro Ala Ser Ser Gln Gly Arg
            180


<210> SEQ ID NO 8
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 8

Met His His His His His His Glu Asn Leu Tyr Phe Gln Gly Ser Gly
1 5 10 15

Pro Ala Glu Glu Glu Ser Gln Val Leu Arg Gly Thr Gly His Cys Lys
20 25 30

Trp Phe Asn Val Arg Met Gly Phe Gly Phe Ile Ser Met Ile Asn Arg
35 40 45

Glu Gly Ser Pro Leu Asp Ile Pro Val Asp Val Phe Val His Gln Ser
50 55 60

Lys Leu Phe Met Glu Gly Phe Arg Ser Leu Lys Glu Gly Glu Pro Val
65 70 75 80

Glu Phe Thr Phe Lys Lys Ser Ser Lys Gly Leu Glu Ser Ile Arg Val
85 90 95

Thr Gly Pro Gly Gly Ser Pro Cys Leu Gly Ser Glu Arg Arg Pro Lys
100 105 110

Gly Gly Asp Arg Cys Tyr Asn Cys Gly Gly Leu Asp His His Ala Lys
115 120 125

Glu Cys Ser Leu Pro Pro Gln Pro Lys Lys Cys His Tyr Cys Gln Ser
130 135 140

Ile Met His Met Val Ala Asn Cys Pro His Lys Asn Val Ala Gln Pro
145 150 155 160

Pro Ala Ser Ser Gln Gly Arg
165

<210> SEQ ID NO 9
<211> LENGTH: 172
<212> TYPE: PRT
<213> ORGANISM: Mus musculus

<400> SEQUENCE: 9

Gly Ser Gly Ala Ala Glu Lys Ala Pro Glu Glu Ala Pro Pro Asp Ala
1 5 10 15

Ala Arg Ala Ala Asp Glu Pro Gln Leu Leu His Gly Ala Gly Ile Cys
20 25 30

Lys Trp Phe Asn Val Arg Met Gly Phe Gly Phe Leu Ser Met Thr Ala
35 40 45

Arg Ala Gly Val Ala Leu Asp Pro Pro Val Asp Val Phe Val His Gln
50 55 60

Ser Lys Leu His Met Glu Gly Phe Arg Ser Leu Lys Glu Gly Glu Ala
65 70 75 80

Val Glu Phe Thr Phe Lys Lys Ser Ala Lys Gly Leu Glu Ser Ile Arg
85 90 95

Val Thr Gly Pro Gly Gly Val Phe Cys Ile Gly Ser Glu Arg Arg Pro
100 105 110

Lys Gly Lys Asn Met Gln Lys Arg Arg Ser Lys Gly Asp Arg Cys Tyr
115 120 125

Asn Cys Gly Gly Leu Asp His His Ala Lys Glu Cys Lys Leu Pro Pro
130 135 140

Gln Pro Lys Lys Cys His Phe Cys Gln Ser Ile Asn His Met Val Ala
145 150 155 160

Ser Cys Pro Leu Lys Ala Gln Gln Gly Pro Ser Ser
165 170

<210> SEQ ID NO 10
<211> LENGTH: 151
<212> TYPE: PRT
<213> ORGANISM: Mus musculus

<400> SEQUENCE: 10

```
Gly Ser Gly Ala Ala Asp Glu Pro Gln Leu Leu His Gly Ala Gly Ile
1               5                   10                  15

Cys Lys Trp Phe Asn Val Arg Met Gly Phe Gly Phe Leu Ser Met Thr
            20                  25                  30

Ala Arg Ala Gly Val Ala Leu Asp Pro Pro Val Asp Val Phe Val His
        35                  40                  45

Gln Ser Lys Leu His Met Glu Gly Phe Arg Ser Leu Lys Glu Gly Glu
    50                  55                  60

Ala Val Glu Phe Thr Phe Lys Lys Ser Ala Lys Gly Leu Glu Ser Ile
65                  70                  75                  80

Arg Val Thr Gly Pro Gly Gly Val Phe Cys Ile Gly Ser Glu Arg Arg
                85                  90                  95

Pro Lys Gly Gly Asp Arg Cys Tyr Asn Cys Gly Gly Leu Asp His His
            100                 105                 110

Ala Lys Glu Cys Lys Leu Pro Pro Gln Pro Lys Lys Cys His Phe Cys
        115                 120                 125

Gln Ser Ile Asn His Met Val Ala Ser Cys Pro Leu Lys Ala Gln Gln
    130                 135                 140

Gly Pro Ser Ser Gln Gly Lys
145                 150
```

<210> SEQ ID NO 11
<211> LENGTH: 192
<212> TYPE: PRT
<213> ORGANISM: Mus musculus

<400> SEQUENCE: 11

```
Gly Ser Gly Glu Glu Pro Glu Lys Leu Pro Gly Leu Ala Glu Asp Glu
1               5                   10                  15

Pro Gln Val Leu His Gly Thr Gly His Cys Lys Trp Phe Asn Val Arg
            20                  25                  30

Met Gly Phe Gly Phe Ile Ser Met Ile Ser Arg Glu Gly Asn Pro Leu
        35                  40                  45

Asp Ile Pro Val Asp Val Phe Val His Gln Ser Lys Leu Phe Met Glu
    50                  55                  60

Gly Phe Arg Ser Leu Lys Glu Gly Glu Pro Val Glu Phe Thr Phe Lys
65                  70                  75                  80

Lys Ser Pro Lys Gly Leu Glu Ser Ile Arg Val Thr Gly Pro Gly Gly
                85                  90                  95

Ser Pro Cys Leu Gly Ser Glu Arg Arg Pro Lys Gly Lys Thr Leu Gln
            100                 105                 110

Lys Arg Lys Pro Lys Gly Asp Arg Trp Arg Arg Gln Asp Leu Leu Met
        115                 120                 125

Asp Gln Met Trp Thr Val Arg Glu Glu Glu Ser Arg Met Ile Pro Arg
    130                 135                 140

Cys Tyr Asn Cys Gly Gly Leu Asp His His Ala Lys Glu Cys Ser Leu
145                 150                 155                 160
```

```
Pro Pro Gln Pro Lys Lys Cys His Tyr Cys Gln Ser Ile Met His Met
                165                 170                 175

Val Ala Asn Cys Pro His Lys Leu Ala Ala Gln Leu Pro Ala Ser Ser
            180                 185                 190


<210> SEQ ID NO 12
<211> LENGTH: 175
<212> TYPE: PRT
<213> ORGANISM: Homo sapiens

<400> SEQUENCE: 12

Gly Ser Gly Ala Ala Glu Glu Ala Pro Glu Glu Ala Pro Glu Asp Ala
1               5                   10                  15

Ala Arg Ala Ala Asp Glu Pro Gln Leu Leu His Gly Ala Gly Ile Cys
            20                  25                  30

Lys Trp Phe Asn Val Arg Met Gly Phe Gly Phe Leu Ser Met Thr Ala
        35                  40                  45

Arg Ala Gly Val Ala Leu Asp Pro Pro Val Asp Val Phe Val His Gln
    50                  55                  60

Ser Lys Leu His Met Glu Gly Phe Arg Ser Leu Lys Glu Gly Glu Ala
65                  70                  75                  80

Val Glu Phe Thr Phe Lys Lys Ser Ala Lys Gly Leu Glu Ser Ile Arg
                85                  90                  95

Val Thr Gly Pro Gly Gly Val Phe Cys Ile Gly Ser Glu Arg Arg Pro
            100                 105                 110

Lys Gly Lys Ser Met Gln Lys Arg Arg Ser Lys Gly Asp Arg Cys Tyr
        115                 120                 125

Asn Cys Gly Gly Leu Asp His His Ala Lys Glu Cys Lys Leu Pro Pro
    130                 135                 140

Gln Pro Lys Lys Cys His Phe Cys Gln Ser Ile Ser His Met Val Ala
145                 150                 155                 160

Ser Cys Pro Leu Lys Ala Gln Gln Gly Pro Ser Ala Gln Gly Lys
                165                 170                 175


<210> SEQ ID NO 13
<211> LENGTH: 151
<212> TYPE: PRT
<213> ORGANISM: Homo sapiens

<400> SEQUENCE: 13

Gly Ser Gly Ala Ala Asp Glu Pro Gln Leu Leu His Gly Ala Gly Ile
1               5                   10                  15

Cys Lys Trp Phe Asn Val Arg Met Gly Phe Gly Phe Leu Ser Met Thr
            20                  25                  30

Ala Arg Ala Gly Val Ala Leu Asp Pro Pro Val Asp Val Phe Val His
        35                  40                  45

Gln Ser Lys Leu His Met Glu Gly Phe Arg Ser Leu Lys Glu Gly Glu
    50                  55                  60

Ala Val Glu Phe Thr Phe Lys Lys Ser Ala Lys Gly Leu Glu Ser Ile
65                  70                  75                  80

Arg Val Thr Gly Pro Gly Gly Val Phe Cys Ile Gly Ser Glu Arg Arg
                85                  90                  95

Pro Lys Gly Gly Asp Arg Cys Tyr Asn Cys Gly Gly Leu Asp His His
            100                 105                 110

Ala Lys Glu Cys Lys Leu Pro Pro Gln Pro Lys Lys Cys His Phe Cys
        115                 120                 125
```

```
Gln Ser Ile Ser His Met Val Ala Ser Cys Pro Leu Lys Ala Gln Gln
    130                 135                 140

Gly Pro Ser Ala Gln Gly Lys
145                 150


<210> SEQ ID NO 14
<211> LENGTH: 171
<212> TYPE: PRT
<213> ORGANISM: Homo sapiens

<400> SEQUENCE: 14

Gly Ser Gly Glu Glu Pro Gly Lys Leu Pro Glu Pro Ala Glu Glu Glu
1               5                   10                  15

Ser Gln Val Leu Arg Gly Thr Gly His Cys Lys Trp Phe Asn Val Arg
            20                  25                  30

Met Gly Phe Gly Phe Ile Ser Met Ile Asn Arg Glu Gly Ser Pro Leu
        35                  40                  45

Asp Ile Pro Val Asp Val Phe Val His Gln Ser Lys Leu Phe Met Glu
    50                  55                  60

Gly Phe Arg Ser Leu Lys Glu Gly Glu Pro Val Glu Phe Thr Phe Lys
65                  70                  75                  80

Lys Ser Ser Lys Gly Leu Glu Ser Ile Arg Val Thr Gly Pro Gly Gly
                85                  90                  95

Ser Pro Cys Leu Gly Ser Glu Arg Arg Pro Lys Gly Lys Thr Leu Gln
            100                 105                 110

Lys Arg Lys Pro Lys Gly Asp Arg Cys Tyr Asn Cys Gly Gly Leu Asp
        115                 120                 125

His His Ala Lys Glu Cys Ser Leu Pro Pro Gln Pro Lys Lys Cys His
    130                 135                 140

Tyr Cys Gln Ser Ile Met His Met Val Ala Asn Cys Pro His Lys Asn
145                 150                 155                 160

Val Ala Gln Pro Pro Ala Ser Ser Gln Gly Arg
                165                 170


<210> SEQ ID NO 15
<211> LENGTH: 84
<212> TYPE: PRT
<213> ORGANISM: Homo sapiens

<400> SEQUENCE: 15

Gly Ser Gly Pro Ala Glu Glu Glu Ser Gln Val Leu Arg Gly Thr Gly
1               5                   10                  15

His Cys Lys Trp Phe Asn Val Arg Met Gly Phe Gly Phe Ile Ser Met
            20                  25                  30

Ile Asn Arg Glu Gly Ser Pro Leu Asp Ile Pro Val Asp Val Phe Val
        35                  40                  45

His Gln Ser Lys Leu Phe Met Glu Gly Phe Arg Ser Leu Lys Glu Gly
    50                  55                  60

Glu Pro Val Glu Phe Thr Phe Lys Lys Ser Ser Lys Gly Leu Glu Ser
65                  70                  75                  80

Ile Arg Val Thr


<210> SEQ ID NO 16
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 16
gggcagagau uuugcccgga g 21

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gggguaguga uuuuacccug gag 23

<210> SEQ ID NO 18
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggggucuaug auaccacccc ggag 24

<210> SEQ ID NO 19
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuagggcagg gauuuugccc acaaggaggu 30

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uagaauuaca ucaagggaga u 21

<210> SEQ ID NO 21
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gugggguagu gauuuuaccc uguucaggag au 32

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
uagaguuaca cccugggagu u 21

<210> SEQ ID NO 23
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
uggggcucug cccugcuaug ggau 24

<210> SEQ ID NO 24
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24
ggucggguug ugacauugcc cgcuguggag au 32

<210> SEQ ID NO 25
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25
uuagggucau accccaucuu ggagau 26

<210> SEQ ID NO 26
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 26
ugagggucua ugauaccacc cgguacagga gau 33

<210> SEQ ID NO 27
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27
uuagggucac acccaccacu gggagau 27

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gaggaggaca cccaaggaga uc                                                  22

<210> SEQ ID NO 29
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucagggcagu gauguugccc cucggaagau                                          30

<210> SEQ ID NO 30
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gugggguagg gauauuaggc cccaauuaga agau                                     34

<210> SEQ ID NO 31
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uaagggucug ugacaccacc cucuguugga gau                                      33

<210> SEQ ID NO 32
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gguagggucu rugayayyrc ccgsuryrgg agau                                     34

<210> SEQ ID NO 33
<211> LENGTH: 29
<212> TYPE: PRT
<213> ORGANISM: Unknown
<220> FEATURE:
<223> OTHER INFORMATION: Description of Unknown: GALA peptide

<400> SEQUENCE: 33

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25

<210> SEQ ID NO 34
<211> LENGTH: 30
<212> TYPE: PRT
<213> ORGANISM: Unknown
<220> FEATURE:
<223> OTHER INFORMATION: Description of Unknown: EALA peptide

<400> SEQUENCE: 34

```
Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30
```

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

```
Ala Leu Glu Ala Leu Ala Glu Ala Leu Glu Ala Leu Ala Glu Ala
1               5                   10                  15
```

<210> SEQ ID NO 36
<211> LENGTH: 22
<212> TYPE: PRT
<213> ORGANISM: Unknown
<220> FEATURE:
<223> OTHER INFORMATION: Description of Unknown: INF-7 peptide

<400> SEQUENCE: 36

```
Gly Leu Phe Glu Ala Ile Glu Gly Phe Ile Glu Asn Gly Trp Glu Gly
1               5                   10                  15

Met Ile Trp Asp Tyr Gly
            20
```

<210> SEQ ID NO 37
<211> LENGTH: 23
<212> TYPE: PRT
<213> ORGANISM: Unknown
<220> FEATURE:
<223> OTHER INFORMATION: Description of Unknown: InfHA-2 peptide

<400> SEQUENCE: 37

```
Gly Leu Phe Gly Ala Ile Ala Gly Phe Ile Glu Asn Gly Trp Glu Gly
1               5                   10                  15

Met Ile Asp Gly Trp Tyr Gly
            20
```

<210> SEQ ID NO 38
<211> LENGTH: 48
<212> TYPE: PRT
<213> ORGANISM: Unknown
<220> FEATURE:
<223> OTHER INFORMATION: Description of Unknown: diINF-7 peptide

<400> SEQUENCE: 38

```
Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45
```

```
<210> SEQ ID NO 39
<211> LENGTH: 44
<212> TYPE: PRT
<213> ORGANISM: Unknown
<220> FEATURE:
<223> OTHER INFORMATION: Description of Unknown: diINF-3 peptide

<400> SEQUENCE: 39

Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40


<210> SEQ ID NO 40
<211> LENGTH: 35
<212> TYPE: PRT
<213> ORGANISM: Unknown
<220> FEATURE:
<223> OTHER INFORMATION: Description of Unknown: GLF peptide

<400> SEQUENCE: 40

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35


<210> SEQ ID NO 41
<211> LENGTH: 34
<212> TYPE: PRT
<213> ORGANISM: Unknown
<220> FEATURE:
<223> OTHER INFORMATION: Description of Unknown: GALA-INF3 peptide

<400> SEQUENCE: 41

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys


<210> SEQ ID NO 42
<211> LENGTH: 41
<212> TYPE: PRT
<213> ORGANISM: Unknown
<220> FEATURE:
<223> OTHER INFORMATION: Description of Unknown: INF-5 peptide
<220> FEATURE:
<221> NAME/KEY: MOD_RES
<222> LOCATION: (17)..(17)
<223> OTHER INFORMATION: Nle
<220> FEATURE:
<221> NAME/KEY: MOD_RES
<222> LOCATION: (38)..(38)
<223> OTHER INFORMATION: Nle
```

<400> SEQUENCE: 42

Gly Leu Phe Glu Ala Ile Glu Gly Phe Ile Glu Asn Gly Trp Glu Gly
1               5                   10                  15

Leu Ile Asp Gly Lys Gly Leu Phe Glu Ala Ile Glu Gly Phe Ile Glu
            20                  25                  30

Asn Gly Trp Glu Gly Leu Ile Asp Gly
        35                  40

<210> SEQ ID NO 43
<211> LENGTH: 19
<212> TYPE: PRT
<213> ORGANISM: Unknown
<220> FEATURE:
<223> OTHER INFORMATION: Description of Unknown: JTS-1 peptide

<400> SEQUENCE: 43

Leu Phe Glu Ala Leu Leu Glu Leu Leu Glu Ser Leu Trp Glu Leu Leu
1               5                   10                  15

Leu Glu Ala

<210> SEQ ID NO 44
<211> LENGTH: 20
<212> TYPE: PRT
<213> ORGANISM: Unknown
<220> FEATURE:
<223> OTHER INFORMATION: Description of Unknown: ppTG1 peptide

<400> SEQUENCE: 44

Gly Leu Phe Lys Ala Leu Leu Lys Leu Leu Lys Ser Leu Trp Lys Leu
1               5                   10                  15

Leu Leu Lys Ala
            20

<210> SEQ ID NO 45
<211> LENGTH: 20
<212> TYPE: PRT
<213> ORGANISM: Unknown
<220> FEATURE:
<223> OTHER INFORMATION: Description of Unknown: ppTG20 peptide

<400> SEQUENCE: 45

Gly Leu Phe Arg Ala Leu Leu Arg Leu Leu Arg Ser Leu Trp Arg Leu
1               5                   10                  15

Leu Leu Arg Ala
            20

<210> SEQ ID NO 46
<211> LENGTH: 30
<212> TYPE: PRT
<213> ORGANISM: Unknown
<220> FEATURE:
<223> OTHER INFORMATION: Description of Unknown: KALA peptide

<400> SEQUENCE: 46

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 47
<211> LENGTH: 22
<212> TYPE: PRT
<213> ORGANISM: Unknown

<220> FEATURE:
<223> OTHER INFORMATION: Description of Unknown: HA peptide

<400> SEQUENCE: 47

Gly Leu Phe Phe Glu Ala Ile Ala Glu Phe Ile Glu Gly Gly Trp Glu
1 5 10 15

Gly Leu Ile Glu Gly Cys
20

<210> SEQ ID NO 48
<211> LENGTH: 26
<212> TYPE: PRT
<213> ORGANISM: Unknown
<220> FEATURE:
<223> OTHER INFORMATION: Description of Unknown: Melittin peptide

<400> SEQUENCE: 48

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 49
<211> LENGTH: 16
<212> TYPE: PRT
<213> ORGANISM: Unknown
<220> FEATURE:
<223> OTHER INFORMATION: Description of Unknown: penetratin peptide

<400> SEQUENCE: 49

Arg Gln Ile Lys Ile Trp Phe Gln Asn Arg Arg Met Lys Trp Lys Lys
1 5 10 15

<210> SEQ ID NO 50
<211> LENGTH: 14
<212> TYPE: PRT
<213> ORGANISM: Human immunodeficiency virus

<400> SEQUENCE: 50

Gly Arg Lys Lys Arg Arg Gln Arg Arg Arg Pro Pro Gln Cys
1 5 10

<210> SEQ ID NO 51
<211> LENGTH: 27
<212> TYPE: PRT
<213> ORGANISM: Unknown
<220> FEATURE:
<223> OTHER INFORMATION: Description of Unknown: signal sequence based
peptide

<400> SEQUENCE: 51

Gly Ala Leu Phe Leu Gly Trp Leu Gly Ala Ala Gly Ser Thr Met Gly
1 5 10 15

Ala Trp Ser Gln Pro Lys Lys Lys Arg Lys Val
20 25

<210> SEQ ID NO 52
<211> LENGTH: 18
<212> TYPE: PRT
<213> ORGANISM: Unknown
<220> FEATURE:
<223> OTHER INFORMATION: Description of Unknown: PVEC peptide

<400> SEQUENCE: 52

Leu Leu Ile Ile Leu Arg Arg Arg Ile Arg Lys Gln Ala His Ala His
1 5 10 15

Ser Lys

<210> SEQ ID NO 53
<211> LENGTH: 26
<212> TYPE: PRT
<213> ORGANISM: Unknown
<220> FEATURE:
<223> OTHER INFORMATION: Description of Unknown: transportan peptide

<400> SEQUENCE: 53

Gly Trp Thr Leu Asn Ser Ala Gly Tyr Leu Leu Lys Ile Asn Leu Lys
1 5 10 15

Ala Leu Ala Ala Leu Ala Lys Lys Ile Leu
20 25

<210> SEQ ID NO 54
<211> LENGTH: 18
<212> TYPE: PRT
<213> ORGANISM: Unknown
<220> FEATURE:
<223> OTHER INFORMATION: Description of Unknown: amphiphilic model peptide

<400> SEQUENCE: 54

Lys Leu Ala Leu Lys Leu Ala Leu Lys Ala Leu Lys Ala Ala Leu Lys
1 5 10 15

Leu Ala

<210> SEQ ID NO 55
<211> LENGTH: 9
<212> TYPE: PRT
<213> ORGANISM: Unknown
<220> FEATURE:
<223> OTHER INFORMATION: Description of Unknown: Arg9 motif peptide

<400> SEQUENCE: 55

Arg Arg Arg Arg Arg Arg Arg Arg Arg
1 5

<210> SEQ ID NO 56
<211> LENGTH: 10
<212> TYPE: PRT
<213> ORGANISM: Unknown
<220> FEATURE:
<223> OTHER INFORMATION: Description of Unknown: Bacterial cell wall permeating peptide

<400> SEQUENCE: 56

Lys Phe Phe Lys Phe Phe Lys Phe Phe Lys
1 5 10

<210> SEQ ID NO 57
<211> LENGTH: 37
<212> TYPE: PRT
<213> ORGANISM: Unknown
<220> FEATURE:
<223> OTHER INFORMATION: Description of Unknown: LL-37 peptide

<400> SEQUENCE: 57

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 58
<211> LENGTH: 31
<212> TYPE: PRT
<213> ORGANISM: Unknown
<220> FEATURE:
<223> OTHER INFORMATION: Description of Unknown: Cecropin P1 peptide

<400> SEQUENCE: 58

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 59
<211> LENGTH: 30
<212> TYPE: PRT
<213> ORGANISM: Unknown
<220> FEATURE:
<223> OTHER INFORMATION: Description of Unknown: alpha-defensin peptide

<400> SEQUENCE: 59

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 60
<211> LENGTH: 36
<212> TYPE: PRT
<213> ORGANISM: Unknown
<220> FEATURE:
<223> OTHER INFORMATION: Description of Unknown: beta-defensin peptide

<400> SEQUENCE: 60

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 61
<211> LENGTH: 42
<212> TYPE: PRT
<213> ORGANISM: Unknown
<220> FEATURE:
<223> OTHER INFORMATION: Description of Unknown: PR-39 peptide
<220> FEATURE:
<223> OTHER INFORMATION: C-term NH2

-continued

<400> SEQUENCE: 61

Arg Arg Arg Pro Arg Pro Pro Tyr Leu Pro Arg Pro Arg Pro Pro Pro
1 5 10 15

Phe Phe Pro Pro Arg Leu Pro Pro Arg Ile Pro Pro Gly Phe Pro Pro
20 25 30

Arg Phe Pro Pro Arg Phe Pro Gly Lys Arg
35 40

<210> SEQ ID NO 62
<211> LENGTH: 13
<212> TYPE: PRT
<213> ORGANISM: Unknown
<220> FEATURE:
<223> OTHER INFORMATION: Description of Unknown: indolicidin peptide
<220> FEATURE:
<223> OTHER INFORMATION: C-term NH2

<400> SEQUENCE: 62

Ile Leu Pro Trp Lys Trp Pro Trp Trp Pro Trp Arg Arg
1 5 10

<210> SEQ ID NO 63
<211> LENGTH: 16
<212> TYPE: PRT
<213> ORGANISM: Unknown
<220> FEATURE:
<223> OTHER INFORMATION: Description of Unknown: RFGF peptide

<400> SEQUENCE: 63

Ala Ala Val Ala Leu Leu Pro Ala Val Leu Leu Ala Leu Leu Ala Pro
1 5 10 15

<210> SEQ ID NO 64
<211> LENGTH: 11
<212> TYPE: PRT
<213> ORGANISM: Unknown
<220> FEATURE:
<223> OTHER INFORMATION: Description of Unknown: RFGF analogue peptide

<400> SEQUENCE: 64

Ala Ala Leu Leu Pro Val Leu Leu Ala Ala Pro
1 5 10

<210> SEQ ID NO 65
<211> LENGTH: 12
<212> TYPE: PRT
<213> ORGANISM: Unknown
<220> FEATURE:
<223> OTHER INFORMATION: Description of Unknown: bactenecin peptide

<400> SEQUENCE: 65

Arg Lys Cys Arg Ile Val Val Ile Arg Val Cys Arg
1 5 10

<210> SEQ ID NO 66
<211> LENGTH: 3459
<212> TYPE: DNA
<213> ORGANISM: Homo sapiens

<400> SEQUENCE: 66
cctttgcctt cggacttctc cggggccagc agccgcccga ccaggggccc ggggccacgg 60
gctcagccga cgaccatggg ctccgtgtcc aaccagcagt ttgcaggtgg ctgcgccaag 120
gcggcagaag aggcgcccga ggaggcgccg gaggacgcgg cccgggcggc ggacgagcct 180

-continued

```
cagctgctgc acggtgcggg catctgtaag tggttcaacg tgcgcatggg gttcggcttc    240
ctgtccatga ccgcccgcgc cggggtcgcg ctcgaccccc cagtggatgt ctttgtgcac    300
cagagtaagc tgcacatgga agggttccgg agcttgaagg agggtgaggc agtggagttc    360
acctttaaga agtcagccaa gggtctggaa tccatccgtg tcaccggacc tggtggagta    420
ttctgtattg ggagtgagag gcggccaaaa ggaaagagca tgcagaagcg cagatcaaaa    480
ggagacaggt gctacaactg tggaggtcta gatcatcatg ccaaggaatg caagctgcca    540
ccccagccca agaagtgcca cttctgccag agcatcagcc atatggtagc ctcatgtccg    600
ctgaaggccc agcagggccc tagtgcacag ggaaagccaa cctactttcg agaggaagaa    660
gaagaaatcc acagccctac cctgctcccg gaggcacaga attgagccac aatgggtggg    720
ggctattctt ttgctatcag gaagttttga ggagcaggca gagtggagaa agtgggaata    780
gggtgcattg gggctagttg gcactgccat gtatctcagg cttgggttca caccatcacc    840
ctttcttccc tctaggtggg gggaaagggt gagtcaaagg aactccaacc atgctctgtc    900
caaatgcaag tgagggttct gggggcaacc aggagggggg aatcacccta caacctgcat    960
attttgagtc tccatcccca gaatttccag cttttgaaag tggcctggat agggaagttg   1020
ttttcctttt aaagaaggat atataataat tcccatgcca gagtgaaatg attaagtata   1080
agaccagatt catggagcca agccactaca ttctgtggaa ggagatctct caggagtaag   1140
cattgttttt ttttcacatc ttgtatcctc atacccactt ttgggatagg gtgctggcag   1200
ctgtcccaag caatgggtaa tgatgatggc aaaaagggtg tttgggggaa cagctgcaga   1260
cctgctgctc tatgctcacc cccgccccat tctgggccaa tgtgatttta tttatttgct   1320
cccttggata ctgcaccttg ggtcccactt tctccaggat gccaactgca ctagctgtgt   1380
gcgaatgacg tatcttgtgc attttaactt tttttcctta atataaatat tctggttttg   1440
tatttttgta tattttaatc taaggccctc atttcctgca ctgtgttctc aggtacatga   1500
gcaatctcag ggatagccag cagcagctcc aggtctgcgc agcaggaatt actttttgtt   1560
gtttttgcca ccgtggagag caactatttg gagtgcacag cctattgaac tacctcattt   1620
ttgccaataa gagctggctt ttctgccata gtgtcctctt gaaaccccct ctgccttgaa   1680
aatgttttat gggagactag gttttaactg ggtggcccca tgacttgatt gccttctact   1740
ggaagattgg gaattagtct aaacaggaaa tggtggtaca cagaggctag gagaggctgg   1800
gcccggtgaa aaggccagag agcaagccaa gattaggtga gggttgtcta atcctatggc   1860
acaggacgtg ctttacatct ccagatctgt tcttcaccag attaggttag gcctaccatg   1920
tgccacaggg tgtgtgtgtg tttgtaaaac tagagttgct aaggataagt ttaaagacca   1980
atacccctgt acttaatcct gtgctgtcga gggatggata tatgaagtaa ggtgagatcc   2040
ttaacctttc aaaattttcg ggttccaggg agacacacaa gcgagggttt tgtggtgcct   2100
ggagcctgtg tcctgccctg ctacagtagt gattaatagt gtcatggtag ctaaaggaga   2160
aaaagggggt ttcgtttaca cgctgtgaga tcaccgcaaa cctaccttac tgtgttgaaa   2220
cgggacaaat gcaatagaac gcattgggtg gtgtgtgtct gatcctgggt tcttgtctcc   2280
cctaaatgct gcccccccaag ttactgtatt tgtctgggct ttgtaggact tcactacgtt   2340
gattgctagg tggcctagtt tgtgtaaata taatgtattg gtctttctcc gtgttctttg   2400
ggggttttgt ttacaaactt ctttttgtat tgagagaaaa atagccaaag catctttgac   2460
agaaggttct gcaccaggca aaaagatctg aaacattagt ttgggggcc ctcttcttaa   2520
agggggggatc ttgaaccatc ctttcttttg tattcccctt cccctattac ctattagacc   2580
```

-continued

```
agatcttctg tcctaaaaac ttgtcttcta ccctgccctc ttttctgttc acccccaaaa   2640

gaaaacttac acacccacac acatacacat ttcatgcttg gagtgtctcc acaactctta   2700

aatgatgtat gcaaaaatac tgaagctagg aaaaccctcc gtcccttgtt cccaacctcc   2760

taagtcaaga ccattaccat ttctttcttt cttttttttt tttttttaa agtggagtct   2820

cgctgtgtca cccaggcaga ggttgcagtg agctgagatc gcaccactgc actccagcct   2880

ggttacagag cgagactctg tctcaaacaa aacaaaacaa aacaaaaaca cactactgta   2940

ttttggatgg atcaaacctc cttaatttta atttctaatc ctaaagtaaa gagatgcaat   3000

tgggggcctt ccatgtagaa agtggggtca ggaggccaag aaagggaata tgaatgtata   3060

tccaagtcac tcaggaactt ttatgcaggt gctagaaact ttatgtcaaa gtggccacaa   3120

gattgtttaa taggagacga acgaatgtaa ctccatgttt actgctaaaa accaaagctt   3180

tgtgtaaaat cttgaattta tggggcggga gggtaggaaa gcctgtacct gtctgttttt   3240

ttcctgatcc ttttccctca ttcctgaact gcaggagact gagccccttt gggctttggt   3300

gaccccatca ctggggtgtg tttatttgat ggttgatttt gctgtactgg gtacttcctt   3360

tcccattttc taatcatttt ttaacacaag ctgactcttc ccttcccttc tcctttccct   3420

gggaaaatac aatgaataaa taaagactta ttggtacgc                          3459
```

<210> SEQ ID NO 67
<211> LENGTH: 4014
<212> TYPE: DNA
<213> ORGANISM: Homo sapiens

<400> SEQUENCE: 67

```
gtgcggggga agatgtagca gcttcttctc cgaaccaacc ctttgccttc ggacttctcc     60

ggggccagca gccgcccgac caggggcccg gggccacggg ctcagccgac gaccatgggc    120

tccgtgtcca accagcagtt tgcaggtggc tgcgccaagg cggcagaaga ggcgcccgag    180

gaggcgccgg aggacgcggc ccgggcggcg gacgagcctc agctgctgca cggtgcgggc    240

atctgtaagt ggttcaacgt gcgcatgggg ttcggcttcc tgtccatgac cgcccgcgcc    300

ggggtcgcgc tcgaccccc agtggatgtc tttgtgcacc agagtaagct gcacatggaa    360

gggttccgga gcttgaagga gggtgaggca gtggagttca cctttaagaa gtcagccaag    420

ggtctggaat ccatccgtgt caccggacct ggtggagtat tctgtattgg gagtgagagg    480

cggccaaaag gaaagagcat gcagaagcgc agatcaaaag gagacaggtg ctacaactgt    540

ggaggtctag atcatcatgc caaggaatgc aagctgccac cccagcccaa gaagtgccac    600

ttctgccaga gcatcagcca tatggtagcc tcatgtccgc tgaaggccca gcagggccct    660

agtgcacagg gaaagccaac ctactttcga gaggaagaag aagaaatcca cagccctacc    720

ctgctcccgg aggcacagaa ttgagccaca atgggtgggg gctattcttt tgctatcagg    780

aagttttgag gagcaggcag agtggagaaa gtgggaatag ggtgcattgg ggctagttgg    840

cactgccatg tatctcaggc ttgggttcac accatcaccc tttcttccct ctaggtgggg    900

ggaaagggtg agtcaaagga actccaacca tgctctgtcc aaatgcaagt gagggttctg    960

ggggcaacca ggaggggga atcaccctac aacctgcata ctttgagtct ccatccccag   1020

aatttccagc ttttgaaagt ggcctggata gggaagttgt tttcctttta aagaaggata   1080

tataataatt cccatgccag agtgaaatga ttaagtataa gaccagattc atggagccaa   1140

gccactacat tctgtggaag gagatctctc aggagtaagc attgtttttt tttcacatct   1200

tgtatcctca tacccacttt tgggataggg tgctggcagc tgtcccaagc aatgggtaat   1260
```

-continued gatgatggca aaaagggtgt ttgggggaac agctgcagac ctgctgctct atgctcaccc 1320
ccgccccatt ctgggccaat gtgattttat ttatttgctc ccttggatac tgcaccttgg 1380
gtcccacttt ctccaggatg ccaactgcac tagctgtgtg cgaatgacgt atcttgtgca 1440
ttttaacttt ttttccttaa tataaatatt ctggttttgt atttttgtat attttaatct 1500
aaggccctca tttcctgcac tgtgttctca ggtacatgag caatctcagg gatagccagc 1560
agcagctcca ggtctgcgca gcaggaatta ctttttgttg tttttgccac cgtggagagc 1620
aactatttgg agtgcacagc ctattgaact acctcatttt tgccaataag agctggcttt 1680
tctgccatag tgtcctcttg aaacccccctc tgccttgaaa atgttttatg ggagactagg 1740
ttttaactgg gtggccccat gacttgattg ccttctactg gaagattggg aattagtcta 1800
aacaggaaat ggtggtacac agaggctagg agaggctggg cccggtgaaa aggccagaga 1860
gcaagccaag attaggtgag ggttgtctaa tcctatggca caggacgtgc tttacatctc 1920
cagatctgtt cttcaccaga ttaggttagg cctaccatgt gccacagggt gtgtgtgtgt 1980
ttgtaaaact agagttgcta aggataagtt taaagaccaa taccccctgta cttaatcctg 2040
tgctgtcgag ggatggatat atgaagtaag gtgagatcct taacctttca aaattttcgg 2100
gttccaggga gacacacaag cgagggtttt gtggtgcctg gagcctgtgt cctgccctgc 2160
tacagtagtg attaatagtg tcatggtagc taaaggagaa aaagggggtt tcgtttacac 2220
gctgtgagat caccgcaaac ctaccttact gtgttgaaac gggacaaatg caatagaacg 2280
cattgggtgg tgtgtgtctg atcctgggtt cttgtctccc ctaaatgctg ccccccaagt 2340
tactgtattt gtctgggctt tgtaggactt cactacgttg attgctaggt ggcctagttt 2400
gtgtaaatat aatgtattgg tctttctccg tgttctttgg gggttttgtt tacaaacttc 2460
tttttgtatt gagagaaaaa tagccaaagc atctttgaca gaaggttctg caccaggcaa 2520
aaagatctga aacattagtt tggggggccc tcttcttaaa gtggggatct tgaaccatcc 2580
tttcttttgt attccccttc ccctattacc tattagacca gatcttctgt cctaaaaact 2640
tgtcttctac cctgccctct tttctgttca cccccaaaag aaaacttaca cacccacaca 2700
catacacatt tcatgcttgg agtgtctcca caactcttaa atgatgtatg caaaaatact 2760
gaagctagga aaaccctcca tcccttgttc ccaacctcct aagtcaagac cattaccatt 2820
tctttctttc tttttttttt ttttttaaaa tggagtctca ctgtgtcacc caggctggag 2880
tgcagtggca tgatcggctc actgcagcct ctgcctcttg ggttcaagtg attctcctgc 2940
ctcagcctcc tgagtagctg ggatttcagg cacccgccac actcagctaa tttttgtatt 3000
tttagtagag acggggtttc accatgttgt ccaggctggt ctggaactcc tgacctcagg 3060
tgatctgccc accttggctt cccaaagtgc tgggattaca ggcatgagcc accatgctgg 3120
gccaaccatt tcttggtgta ttcatgccaa acacttaaga cactgctgta gcccaggcgc 3180
ggtggctcac acctgtaatc ccagcacttt ggaaggctga ggcgggcgga tcacaaggtc 3240
acgagttcaa aactatcctg gccaacacag tgaaaccccg tctctactaa aatacaaaaa 3300
aattagccgg gtgtggtggt gcatgccttt agtcctagct attcaggagg ctgaggcagg 3360
ggaatcgctt gaacccgaga ggcagaggtt gcagtgagct gagatcgcac cactgcactc 3420
cagcctggtt acagagcaag actctgtctc aaacaaaaca aaacaaaaca aaaacacact 3480
actgtatttt ggatggatca aacctcctta attttaattt ctaatcctaa agtaaagaga 3540
tgcaattggg ggccttccat gtagaaagtg gggtcaggag gccaagaaag ggaatatgaa 3600
tgtatatcca agtcactcag gaacttttat gcaggtgcta gaaactttat gtcaaagtgg 3660

-continued ccacaagatt gtttaatagg agacgaacga atgtaactcc atgtttactg ctaaaaacca 3720
aagctttgtg taaaatcttg aatttatggg gcgggagggt aggaaagcct gtacctgtct 3780
gtttttttcc tgatcctttt ccctcattcc tgaactgcag gagactgagc ccctttgggc 3840
tttggtgacc ccatcactgg ggtgtgttta tttgatggtt gattttgctg tactgggtac 3900
ttcctttccc attttctaat catttttttaa cacaagctga ctcttccctt cccttctcct 3960
ttccctggga aaatacaatg aataaataaa gacttattgg tacgcaaact gtca 4014

<210> SEQ ID NO 68
<211> LENGTH: 209
<212> TYPE: PRT
<213> ORGANISM: Homo sapiens

<400> SEQUENCE: 68

Met Gly Ser Val Ser Asn Gln Gln Phe Ala Gly Gly Cys Ala Lys Ala
1 5 10 15

Ala Glu Glu Ala Pro Glu Glu Ala Pro Glu Asp Ala Ala Arg Ala Ala
20 25 30

Asp Glu Pro Gln Leu Leu His Gly Ala Gly Ile Cys Lys Trp Phe Asn
35 40 45

Val Arg Met Gly Phe Gly Phe Leu Ser Met Thr Ala Arg Ala Gly Val
50 55 60

Ala Leu Asp Pro Pro Val Asp Val Phe Val His Gln Ser Lys Leu His
65 70 75 80

Met Glu Gly Phe Arg Ser Leu Lys Glu Gly Glu Ala Val Glu Phe Thr
85 90 95

Phe Lys Lys Ser Ala Lys Gly Leu Glu Ser Ile Arg Val Thr Gly Pro
100 105 110

Gly Gly Val Phe Cys Ile Gly Ser Glu Arg Arg Pro Lys Gly Lys Ser
115 120 125

Met Gln Lys Arg Arg Ser Lys Gly Asp Arg Cys Tyr Asn Cys Gly Gly
130 135 140

Leu Asp His His Ala Lys Glu Cys Lys Leu Pro Pro Gln Pro Lys Lys
145 150 155 160

Cys His Phe Cys Gln Ser Ile Ser His Met Val Ala Ser Cys Pro Leu
165 170 175

Lys Ala Gln Gln Gly Pro Ser Ala Gln Gly Lys Pro Thr Tyr Phe Arg
180 185 190

Glu Glu Glu Glu Glu Ile His Ser Pro Thr Leu Leu Pro Glu Ala Gln
195 200 205

Asn

<210> SEQ ID NO 69
<211> LENGTH: 250
<212> TYPE: PRT
<213> ORGANISM: Homo sapiens

<400> SEQUENCE: 69

Met Ala Glu Gly Gly Ala Ser Lys Gly Gly Gly Glu Glu Pro Gly Lys
1 5 10 15

Leu Pro Glu Pro Ala Glu Glu Glu Ser Gln Val Leu Arg Gly Thr Gly
20 25 30

His Cys Lys Trp Phe Asn Val Arg Met Gly Phe Gly Phe Ile Ser Met
35 40 45

```
Ile Asn Arg Glu Gly Ser Pro Leu Asp Ile Pro Val Asp Val Phe Val
    50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Ser Lys Gly Leu Glu Ser
                85                  90                  95

Ile Arg Val Thr Gly Pro Gly Gly Ser Pro Cys Leu Gly Ser Glu Arg
            100                 105                 110

Arg Pro Lys Gly Lys Thr Leu Gln Lys Arg Lys Pro Lys Gly Asp Arg
        115                 120                 125

Cys Tyr Asn Cys Gly Gly Leu Asp His His Ala Lys Glu Cys Ser Leu
    130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Pro Ala Ser Ser
                165                 170                 175

Gln Gly Arg Gln Glu Ala Glu Ser Gln Pro Cys Thr Ser Thr Leu Pro
            180                 185                 190

Arg Glu Val Gly Gly Gly His Gly Cys Thr Ser Pro Pro Phe Pro Gln
        195                 200                 205

Glu Ala Arg Ala Glu Ile Ser Glu Arg Ser Gly Arg Ser Pro Gln Glu
    210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250


<210> SEQ ID NO 70
<211> LENGTH: 180
<212> TYPE: PRT
<213> ORGANISM: Homo sapiens

<400> SEQUENCE: 70

Met Glu Gly Phe Arg Ser Leu Lys Glu Gly Glu Pro Val Glu Phe Thr
1               5                   10                  15

Phe Lys Lys Ser Ser Lys Gly Leu Glu Ser Ile Arg Val Thr Gly Pro
            20                  25                  30

Gly Gly Ser Pro Cys Leu Gly Ser Glu Arg Arg Pro Lys Gly Lys Thr
        35                  40                  45

Leu Gln Lys Arg Lys Pro Lys Gly Asp Arg Cys Tyr Asn Cys Gly Gly
    50                  55                  60

Leu Asp His His Ala Lys Glu Cys Ser Leu Pro Pro Gln Pro Lys Lys
65                  70                  75                  80

Cys His Tyr Cys Gln Ser Ile Met His Met Val Ala Asn Cys Pro His
                85                  90                  95

Lys Asn Val Ala Gln Pro Pro Ala Ser Ser Gln Gly Arg Gln Glu Ala
            100                 105                 110

Glu Ser Gln Pro Cys Thr Ser Thr Leu Pro Arg Glu Val Gly Gly Gly
        115                 120                 125

His Gly Cys Thr Ser Pro Pro Phe Pro Gln Glu Ala Arg Ala Glu Ile
    130                 135                 140

Ser Glu Arg Ser Gly Arg Ser Pro Gln Glu Ala Ser Ser Thr Lys Ser
145                 150                 155                 160
```

Ser Ile Ala Pro Glu Glu Gln Ser Lys Lys Gly Pro Ser Val Gln Lys
165 170 175

Arg Lys Lys Thr
180

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 71

His His His His His His
1 5

<210> SEQ ID NO 72
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
uuagggcaga gauuuugccc acaaggaguu 30

<210> SEQ ID NO 73
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
gggcagagau uuugccc 17

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
guuuuagggc agagauuuug ccc 23

<210> SEQ ID NO 75
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
uuagggcaga gauuuugccc acaauu 26

<210> SEQ ID NO 76
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuagggcaga gauuuugccc ggaguu 26

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gggcagagau uuugcccaca aggag 25

<210> SEQ ID NO 78
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuaacaagga guu 13

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gggcagagau uuugcccgga guu 23

<210> SEQ ID NO 80
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uuagggcaga gauuuugccc acaaggag 28

<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gauuuugccc ggagau 16

<210> SEQ ID NO 82
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
agagauuuug gag 13

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ggagaugggc agagau 16

<210> SEQ ID NO 84
<211> LENGTH: 28
<212> TYPE: PRT
<213> ORGANISM: Mus musculus

<400> SEQUENCE: 84

Val Phe Cys Ile Gly Ser Glu Arg Arg Pro Lys Gly Lys Asn Met Gln
1               5                   10                  15

Lys Arg Arg Ser Lys Gly Asp Arg Cys Tyr Asn Cys
            20                  25

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Phe Cys Ile Gly Ser Glu Arg Arg Pro Lys Gly Lys Arg Arg Ser
1               5                   10                  15

Lys Gly Asp Arg Cys Tyr Asn Cys
            20

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Phe Cys Ile Gly Ser Glu Arg Arg Pro Lys Gly Gly Asp Arg Cys
1               5                   10                  15

Tyr Asn Cys

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Phe Cys Ile Gly Ser Gly Asp Arg Cys Tyr Asn Cys
1 5 10

<210> SEQ ID NO 88
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
uuagggucac acccaccacu gggagauaa 29

<210> SEQ ID NO 89
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
uagaguuaca ucaagggaga uaa 23

<210> SEQ ID NO 90
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 90
ucagggcagu gauguugccc cuccgaagau aa 32

<210> SEQ ID NO 91
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
uagaguuaca cccugggagu uaa 23

<210> SEQ ID NO 92
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 92
uugggcucug ccccgcucug cgguaa 26

<210> SEQ ID NO 93
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
uuagggcaga gauuuugccc acaaggaguu aa                                    32

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gaggaagaca cccgaggaga uca                                              23

<210> SEQ ID NO 95
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gugggguagu gauuuuaccc uguuuaggag auaa                                  34

<210> SEQ ID NO 96
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uuagggucau accccaucuu ggagauaa                                         28

<210> SEQ ID NO 97
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugagggucua ugauaccacc cgguacagga gauaa                                 35

<210> SEQ ID NO 98
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ggucggguug ugacauugcc cgcuguggag auaa                                  34

<210> SEQ ID NO 99
<211> LENGTH: 19
<212> TYPE: RNA
<213> ORGANISM: Aedes aegypti

<400> SEQUENCE: 99
gugacugauu aaauaucug                                                   19

<210> SEQ ID NO 100
<211> LENGTH: 21
<212> TYPE: RNA
<213> ORGANISM: Caenorhabditis briggasae

<400> SEQUENCE: 100
uagaauauua cucucgguga a 21

<210> SEQ ID NO 101
<211> LENGTH: 21
<212> TYPE: RNA
<213> ORGANISM: Caenorhabditis elegans

<400> SEQUENCE: 101
uggaauauua ccaccgguga a 21

<210> SEQ ID NO 102
<211> LENGTH: 18
<212> TYPE: RNA
<213> ORGANISM: Culex quinquefasciatus

<400> SEQUENCE: 102
uuaaaaauuc aauaucua 18

<210> SEQ ID NO 103
<211> LENGTH: 20
<212> TYPE: RNA
<213> ORGANISM: Caenorhabditis remanei

<400> SEQUENCE: 103
uagaaucuua ccuuggugaa 20

<210> SEQ ID NO 104
<211> LENGTH: 16
<212> TYPE: RNA
<213> ORGANISM: Drosophila melanogaster

<400> SEQUENCE: 104
guaauuacac aucaua 16

<210> SEQ ID NO 105
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
gugggguagu gauuuuaccc uguuuaggag au 32

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106
uagaguuaca ucaagggaga u 21

<210> SEQ ID NO 107
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 107
ucagggcagu gauguugccc cuccgaagau 30

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 108
gaggaagaca cccgaggaga u 21

<210> SEQ ID NO 109
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 109
gugcuguugg ucggguugug acauugcccg cuguggagau 40

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 110
ugauaccacc cgguacagga g 21

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gln Gly Pro Ser Ser Gln Gly Lys
1 5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Lys Asn Met Gln Lys Arg Arg Ser Lys
1 5

<210> SEQ ID NO 113
<211> LENGTH: 146
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 113

```
Asp Glu Pro Gln Leu Leu His Gly Ala Gly Ile Cys Lys Trp Phe Asn
1               5                   10                  15

Val Arg Met Gly Phe Gly Phe Leu Ser Met Thr Ala Arg Ala Gly Val
            20                  25                  30

Ala Leu Asp Pro Pro Val Asp Val Phe Val His Gln Ser Lys Leu His
        35                  40                  45

Met Glu Gly Phe Arg Ser Leu Lys Glu Gly Glu Ala Val Glu Phe Thr
    50                  55                  60

Phe Lys Lys Ser Ala Lys Gly Leu Glu Ser Ile Arg Val Thr Gly Pro
65                  70                  75                  80

Gly Gly Val Phe Cys Ile Gly Ser Glu Arg Arg Pro Lys Gly Gly Asp
                85                  90                  95

Arg Cys Tyr Asn Cys Gly Gly Leu Asp His His Ala Lys Glu Cys Lys
            100                 105                 110

Leu Pro Pro Gln Pro Lys Lys Cys His Phe Cys Gln Ser Ile Asn His
        115                 120                 125

Met Val Ala Ser Cys Pro Leu Lys Ala Gln Gln Gly Pro Ser Ser Gln
    130                 135                 140

Gly Lys
145
```

<210> SEQ ID NO 114
<211> LENGTH: 91
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 114

```
Gln Leu Leu His Gly Ala Gly Ile Cys Lys Trp Phe Asn Val Arg Met
1               5                   10                  15

Gly Phe Gly Phe Leu Ser Met Thr Ala Arg Ala Gly Val Ala Leu Asp
            20                  25                  30

Pro Pro Val Asp Val Phe Val His Gln Ser Lys Leu His Met Glu Gly
        35                  40                  45

Phe Arg Ser Leu Lys Glu Gly Glu Ala Val Glu Phe Thr Phe Lys Lys
    50                  55                  60

Ser Ala Lys Gly Leu Glu Ser Ile Arg Val Thr Gly Pro Gly Gly Val
65                  70                  75                  80

Phe Cys Ile Gly Ser Glu Arg Arg Pro Lys Gly
                85                  90
```

<210> SEQ ID NO 115
<211> LENGTH: 44
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 115

Gly Asp Arg Cys Tyr Asn Cys Gly Gly Leu Asp His His Ala Lys Glu
1               5                   10                  15

Cys Lys Leu Pro Pro Gln Pro Lys Lys Cys His Phe Cys Gln Ser Ile
            20                  25                  30

Asn His Met Val Ala Ser Cys Pro Leu Lys Ala Gln
        35                  40

<210> SEQ ID NO 116
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Glu Pro Gln Leu Leu His Gly Ala Gly Ile Cys Lys Trp Phe Asn Val
1               5                   10                  15

Arg Met Gly Phe Gly Phe Leu Ser Met Thr Ala Arg Ala Gly Val Ala
            20                  25                  30

Leu Asp Pro Pro Val Asp Val Phe Val His Gln Ser Lys Leu His Met
        35                  40                  45

Glu Gly Phe Arg Ser Leu Lys Glu Gly Glu Ala Val Glu Phe Thr Phe
    50                  55                  60

Lys Lys Ser Ala Lys Gly Leu Glu Ser Ile Arg Val Thr Gly Pro Gly
65                  70                  75                  80

Gly Val Phe Cys Ile Gly Ser Glu Arg Arg Pro Lys Gly
                85                  90

<210> SEQ ID NO 117
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Pro Gln Leu Leu His Gly Ala Gly Ile Cys Lys Trp Phe Asn Val Arg
1               5                   10                  15

Met Gly Phe Gly Phe Leu Ser Met Thr Ala Arg Ala Gly Val Ala Leu
            20                  25                  30

Asp Pro Pro Val Asp Val Phe Val His Gln Ser Lys Leu His Met Glu
        35                  40                  45

Gly Phe Arg Ser Leu Lys Glu Gly Glu Ala Val Glu Phe Thr Phe Lys
    50                  55                  60

Lys Ser Ala Lys Gly Leu Glu Ser Ile Arg Val Thr Gly Pro Gly Gly
65                  70                  75                  80

Val Phe Cys Ile Gly Ser Glu Arg Arg Pro Lys Gly
                85                  90

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 118

gggcagggau uuugcccgga g                                              21


<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Arg Pro Lys Gly Gly
1               5


<210> SEQ ID NO 120
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Pro Gln Leu Leu His Gly Ala Gly Ile Cys Lys Trp Phe Asn Val Arg
1               5                   10                  15

Met Gly Phe Gly Phe Leu Ser Met Thr Ala Arg Ala Gly Val Ala Leu
            20                  25                  30

Asp Pro Pro Val Asp Val Phe Val His Gln Ser Lys Leu His Met Glu
        35                  40                  45

Gly Phe Arg Ser Leu Lys Glu Gly Glu Ala Val Glu Phe Thr Phe Lys
    50                  55                  60

Lys Ser Ala Lys Gly Leu Glu Ser Ile Arg Val Thr Gly Pro Gly Gly
65                  70                  75                  80

Val Phe Cys Ile Gly Ser Glu
                85


<210> SEQ ID NO 121
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Arg Cys Tyr Asn Cys Gly Gly Leu Asp His His Ala Lys Glu Cys
1               5                   10                  15

Lys Leu Pro Pro Gln Pro Lys Lys Cys His Phe Cys Gln Ser Ile Asn
            20                  25                  30

His Met Val Ala Ser Cys Pro Leu Lys Ala Gln
        35                  40
```